(12) United States Patent
Vanderby et al.

(10) Patent No.: US 7,928,059 B2
(45) Date of Patent: Apr. 19, 2011

(54) USE OF NEUROPEPTIDES FOR TRAUMATIC CARTILAGE INJURY

(75) Inventors: Ray Vanderby, Madison, WI (US); Kelley W. Grorud, Janesville, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 769 days.

(21) Appl. No.: 11/431,347

(22) Filed: May 10, 2006

(65) Prior Publication Data

US 2006/0247156 A1    Nov. 2, 2006

Related U.S. Application Data

(63) Continuation-in-part of application No. 11/063,627, filed on Feb. 23, 2005, now Pat. No. 7,776,815.

(60) Provisional application No. 60/547,193, filed on Feb. 24, 2004, provisional application No. 60/679,560, filed on May 10, 2005.

(51) Int. Cl.
| | |
|---|---|
| *A61K 38/00* | (2006.01) |
| *A61K 35/30* | (2006.01) |
| *A61K 35/32* | (2006.01) |
| *A61K 35/12* | (2006.01) |
| *C07K 14/00* | (2006.01) |

(52) U.S. Cl. ............ 514/2; 530/350; 530/839; 530/840; 424/548; 424/570; 424/520

(58) Field of Classification Search ........................ None
See application file for complete search history.

(56) References Cited

U.S. PATENT DOCUMENTS

| | | |
|---|---|---|
| 5,242,902 A | 9/1993 | Murphy et al. |
| 5,616,562 A | 4/1997 | Murphy et al. |
| 6,696,238 B2 | 2/2004 | Murphy et al. |

OTHER PUBLICATIONS

Elefteriou. Cell. Mol. Life Sci. 2005. 62: 2339-2349.*
Delgado et al. Nat. Med. 2001. 7: 563-568.*
Niissalo et al. Ann. N.Y. Acad. Sci. 2002. 966: 384-399.*
McDougall et al. Can. J. Physiol. Pharmacol. 2000. 78: 535-540.*
A data retrieved from the website of www.arhroscopy.com/sp12001.htm based on a Google search on "joint".*
Ackermann P.W., Ahmed M., Kreicbergs A. (2002) Early nerve regeneration after Achilles tendon rupture-a prerequisite for healing? A study on the rat. *J Orthop Res* 20:849-856.
Ackermann P.W., Li J., Lundeberg T., Kreicbergs A. (2003) Neuronal plasticity in relation to nociception and healing of rat achilles tendon. *Journal of Orthopaedic Research* 21:432-441.

Carter R.B. (1991) Topical capsiacin in the treatment of cutaneous disorders. *Drug Development and Research* 22:109-123.
Dray A. (1992) Neuropharmacological mechanisms of capsaicin and related substances. *Biochemical Pharmacology* 44:611-615.
Dunnick C.A., Gibran N.S., Heimbach D.M. (1996) Substance P has a role in neurogenic mediation of human burn wound healing. *Journal of Burn Care & Rehabilitation* 17:390-396.
Field J., Atkins R.M. (1993) Effect of guanethidine on the natural history of post-traumatic algodystrophy. *Annals of the Rheumatic Diseases* 52:467-469.
Gado K., Emery P. (1996) Intra-articular guanethidine injection for resistant shoulder pain: a preliminary double blind study of a novel approach. *Annals of the Rheumatic Diseases* 55:199-201.
Jessell T.M., Iversen L.L., Cuello A.C. (1978) Capsaicin-induced depletion of substance P from primary sensory neurones. *Brain Research* 152:183-188.
Kirschenbaum H.L., Rosenberg J.M. (1984) What to look out for with guanethidine and reserpine. *RN* 47:31-33.
Promotion NCfCDPaH (2000) The prevention and treatment of complications of diabetes mellitus: A guide for primary care prationers. In: (Program CD, ed).
Santoni G., Perfumi M., Bressan A.M., Piccoli M. (1996) Capsaicin-induced inhibition of mitogen and interleukin-2-stimulated T cell proliferation: its reversal by in vivo substance P administration. *Journal of Neuroimmunology* 68:131-138.
Schaffer M., Beiter T., Becker H.D., Hunt T.K. (1998) Neuropeptides: Mediators of inflammation and tissue repair? *Archives of Surgery* 133:1107-1116.
Stroke NIoNDa (2001a) Guillain-Barre syndrome fact sheet. In.
Stroke NIoNDa (2001b) Pain—Hope through research.
Stroke NIoNDa (2001c) Reflex sympathetic dystrophy/complex regional pain syndrome.
Stroke NIoNDa (2001d) NINDS Diabetic Neuropathy Information Page.
Surh Y.J., Lee S.S. (1996) Capsaicin in hot chili pepper: carcinogen, co-carcinogen or anticarcinogen? *Food & Chemical Toxicology* 34:313-316.
Wahren L.K., Gordh T, Jr., Torebjork E. (1995) Effects of regional intravenous guanethidine in patients with neuralgia in the hand; a follow-up study over a decade. *Pain* 62:379-385.

\* cited by examiner

*Primary Examiner* — Jeffrey Stucker
*Assistant Examiner* — Chang-Yu Wang
(74) *Attorney, Agent, or Firm* — Joseph T. Leone, Esq.; DeWitt Ross & Stevens S.C.

(57) ABSTRACT

Disclosed are a method and a corresponding pharmaceutical composition for treating damaged cartilage and subchondral bone. Neurogenic compounds in general and neuropeptides in particular have been found to be highly effective in stimulated repair of cartilage and bone damaged due to traumatic injury, ligament disease, and disuse. Preferred active ingredients for use in the method and corresponding pharmaceutical composition include calcitonin gene-related peptide (CGRP), cholecystokinin (CCK), dynorphin, enkephalin, galanin, neuropeptide Y (NPY), neurotensin, somatostatin, substance P (SP), thyrotropin-releasing hormone (TRH), vasoactive intestinal peptide (VIP).

4 Claims, 26 Drawing Sheets

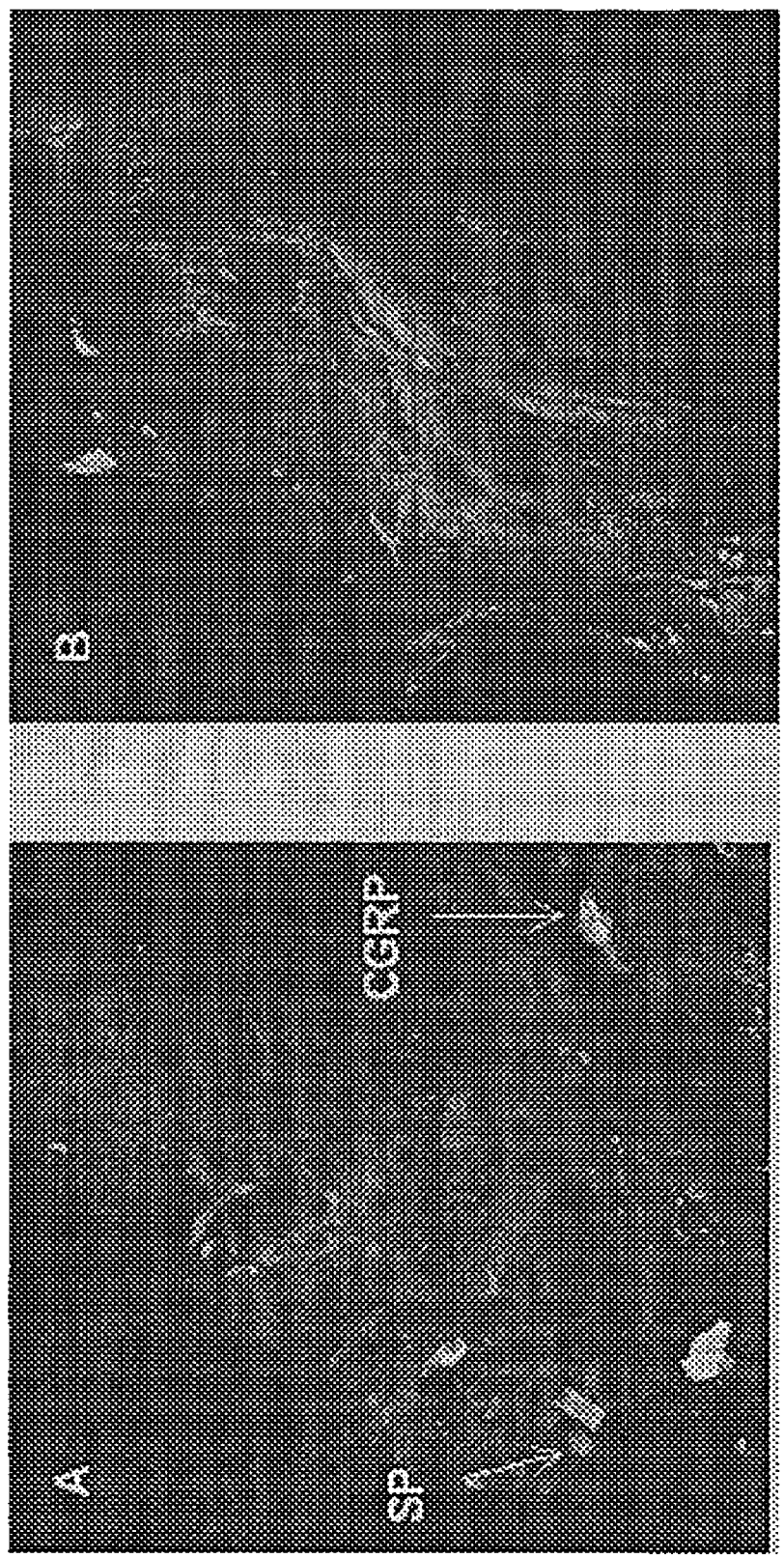

USE OF NEUROPEPTIDES FOR TRAUMATIC CARTILAGE INJURY

CROSS-REFERENCE TO RELATED APPLICATION

This application is a continuation-in-part of application Ser. No. 11/063,627, filed Feb. 23, 2005, now U.S. Pat. No. 7,776,815 which claims priority to provisional application Ser. No. 60/547,193, filed Feb. 24, 2004; this application also claims priority to provisional application Ser. No. 60/679,560, filed May 10, 2005. The contents of all three of these prior applications are incorporated herein.

FEDERAL FUNDING

This invention was made with United States government support awarded by the following agency: NSF 9907977. The United States has certain rights in this invention.

REFERENCES AND INCORPORATION BY REFERENCE

Complete bibliographic citations for the references cited herein are contained in a section titled "References," immediately preceding the claims. All of the documents listed in the "References" section and in the text are incorporated herein.

FIELD OF THE INVENTION

The invention is generally directed to a method of treating connective tissue disease with or without peripheral neuropathies, including acute and chronic joint disease, as well as a method of preventing connective tissue disorders. The invention is specifically directed to a method of treating damaged or ruptured ligaments or tendons, degenerative cartilage disease, traumatic cartilage injury and subchondral bony defects in mammals.

BACKGROUND OF THE INVENTION

"Connective tissue" is defined as tissue of mesodermal origin, for example collagen fibroblasts and fatty cells. Connective tissue supports organs, fills the spaces between organs, and forms tendons, ligaments, and cartilage. As used herein, the term "connective tissue" generally refers to any type of biological tissue with an extensive extracellular matrix.

"Connective tissue diseases" are a collection of disorders and ailments, which comprise connective tissue. Connective tissue diseases can result from, as well as give rise to, a variety of neuropathies. Such neuropathies include diabetic and non-diabetic neuropathies, including complex regional pain syndrome, femoral nerve palsy, and Guillain-Barre syndrome. Connective tissue diseases may be segregated into more discrete pathologies arising from chronic disorders such as degenerative joint disease and acute osteochondral defects, or acute manifestations such as ruptured tendons and ligaments, and torn cartilage, resulting from trauma. These disorders have many pathologic events in common and all result in pain, inflammation, and instability of the affected joint. In many cases, connective tissue diseases can lead to progressive degeneration of the joint or associated organ with increasing discomfort and difficulty of use. Moreover, peripheral neuropathies commonly associated with diabetes frequently manifest themselves as joint disease, poor tissue healing, and/or a compromised immune response.

While the etiology of the various diseases that manifest themselves as connective tissue disease are complex, similar patho-physiologic responses may play a major role in the progression of connective tissue disease and ligament degeneration. One disease with major complications resulting in tissue and joint damage is diabetes. Diabetic pathologies include defects in connective tissue, such as poor wound healing and diminished bone formation and growth. In these tissues, the major protein component is collagen and studies have shown that, in diabetic rats, collagen production was significantly reduced after induction of diabetes (Spanheimer, 1988).

While the causes of various diabetic neuropathies are not completely clear, it is thought that increased blood glucose levels over time result in damage to the blood vessels, connective tissue, nerves and other organs. Further, it is unclear whether a single diabetic pathology promotes the pathological condition of another tissue, or whether each separate pathological condition independently results from increased blood glucose levels. In short, a variety of disorders are associated with diabetes, and the presentation of each particular disorder often differs widely from individual to individual. Because the organs and tissues affected are often quite different from patient to patient, treating diabetic complications is a highly individualized undertaking.

Peripheral nerve disorders are prevalent and can be debilitating, especially among diabetic populations. This is particularly evident in the connective tissues of joints, including tendons, ligaments and cartilage, due to their constant use and visible loss of function. In general, damaged nerves have limited potential for regeneration, and healing in joints following nerve damage is slow and often results in permanent joint damage. At present, many joint disorders are managed through surgical or drug treatments that inhibit painful stimuli from the damaged joint. Despite the prevalence of nerve disorders, little work has been done to elucidate how damage to nervous tissue leads to structural damage to various connective tissues.

Conventional treatments to manage pain resulting from peripheral neuropathies include surgical intervention, chemical intervention and analgesics. Conventional treatments include ligating or transecting the sympathetic nerves to the brachial or femoral plexus. Conventional treatment also includes chemical sympathectomy: chemically blocking sympathetic nerve transduction using guanethidine. In addition, drugs such as capsaicin can be used to block sensory stimuli both topically and internally. In severe instances of femoral pain, femoral nerve transection is an option of last resort.

Recently it has been discovered that classical modes of neuronal stimulation via neuro-transmitters such as epinephrine, nor-epinephrine and acetylcholine are supplemented by the action of other neurogenic compounds. These neurogenic compounds include neuroactive peptides and peptide neurotransmitters. Many of these compounds were originally isolated from the gut and thought to modulate digestion. However, continuing research suggests that these neurogenic compounds are produced throughout the nervous system and have complex effects.

Among the known neuroactive peptides (NPs) are somatostatin, calcitonin gene-related peptide (CGRP), vasoactive intestinal peptide (VIP), Substance P (SP), enkephalin, neuropeptide Y (NPY), neurotensin, thyrotropin-releasing hormone (TRH), cholecystokinin (CCK), galanin and dynorphin, to name a few. (See, generally, "The Biochemical Basis of Neuropharmacology," Cooper, Bloom and Roth, 8th ed., Oxford University Press, New York, 2003, pp. 321-356 and the references cited therein).

Ligaments are a class of connective tissue that are composed primarily of collagen and are located in joints where their primary role is to connect bones to other bones, thereby maintaining the integrity of the joint. Ligament injuries occur frequently in all age groups at all activity levels and may result from acute trauma or underlying disease states.

Healing potential varies widely among ligaments. The anterior cruciate ligament (ACL) has very little healing potential, while the medial cruciate ligament (MCL) has a greater healing potential (although certainly not ideal). Even in ligaments that heal reasonably well (e.g., the MCL), mechanical, biochemical, and morphological alterations continue to persist at least two years post-injury. See, for example, Frank et al. (1995) J. Ortho. Res. 13:157-165. The scar tissue associated with ligament healing is mechanically inferior and compositionally abnormal as compared to uninjured tissue. Healing after ligament injury can then result in ligament laxity, joint instability, prolonged pain, and abnormal joint motion. In Achilles tendon, Ackermann et al. (Ackermann et al., 2002) suggest that nerve regeneration is a prerequisite for healing based in part upon the abundance of neuropeptide Y (NPY) and calcitonin gene-related peptide (CGRP) in the healing tissue. More recently, the Ackerman et al. group discovered that levels of substance P (SP) and CGRP change over the course of tendon healing and remodeling (Ackermann et al., 2003).

Compelling indirect evidence supports the concept that peripheral nerves and peripheral neuropeptides are essential to maintain joint tissues. For example, patients who suffer spinal cord injury, head trauma, or severe burns that damage nerves are more susceptible to heterotopic bone formation or ankylosis of proximal joints. The detailed molecular mechanisms behind this abnormal bone formation are unknown. Proper functioning of the peripheral nervous system, however, appears essential to maintaining healthy joint tissues.

At the cellular level, healing involves cell detachment and re-attachment around the injury site, cell migration, and cell proliferation. Cell migration and proliferation are crucial for healing, and there is mounting evidence that local neuropeptides from the peripheral nervous system (PNS) play an essential role in orchestrating these inflammatory responses (Schaffer et al., 1998).

Peripheral neuropathy is a class of disorders in which tissue damage results from destruction of or damage to peripheral nerves. Peripheral neuropathy includes nerve injury, compression, ischemia, and disease (Association, 2000; Promotion, 2000). Symptoms of peripheral neuropathy vary depending on the types of nerves that are damaged. Damage to sensory nerves can result in dysesthesia (perception of abnormal sensations), while damage to sympathetic nerves can result in wide spread organ problems due to alterations in blood flow (Association, 2000).

One prevalent form of peripheral neuropathy results as a complication of diabetes. Diabetic neuropathy affects approximately 60-70% of diabetics and can degenerate into Charcot joints, which are characterized by joint effusion, fractures, ligament laxity, subluxation, and/or joint dislocation (Association, 2000). Another peripheral neuropathy is femoral mononeuropathy, which results from injury, compression, or surgical transection of the femoral nerve. Femoral mononeuropathy leads to knee "buckling", ligament laxity, decreased patellar reflexes, and medial leg numbness (Sekul, 2001). Other conditions that lead to neuropathy include Complex Regional Pain Syndrome/Reflex Sympathetic Dystrophy Syndrome (CRPS/RSDS), Charcot-Marie-Tooth disease, Guillain-Barre syndrome, rheumatoid arthritis, and neuropathy secondary to ischemia or specific drugs (Stroke, 2001a, b; Stroke, 2001c; Stroke, 2001d).

Release of neuropeptides following injury is generally associated with pain at the site of injury. Thus, chemical inhibitors of sensory and sympathetic nerves are conventionally used to provide pain management in cases of tendonitis, osteoarthritis, and rheumatoid arthritis. As noted earlier, surgical techniques are also used to inhibit nerves to manage pain and hyperhydrosis in extreme cases.

Chemical inhibition of sympathetic nerves can be accomplished with guanethidine, an anti-hypertensive agent that acts in postganglionic sympathetic nerve endings by blocking the release of norepinephrine from nerve terminals (Kirschenbaum and Rosenberg, 1984). Guanethidine has been used as an anti-hypertensive drug for more than 40 years due to the fact that it blocks the sympathetic PNS in two ways: 1) it causes a release of norepinephrine from nerve endings; and 2) it blocks the normal release of catecholamines resulting from nerve stimulation. Guanethidine is conventionally used in the treatment of certain joint disorders, including reflex sympathetic dystrophy (Sudeck's atrophy) (Field and Atkins, 1993), neuralgia of the hands (Wahren et al., 1995), and shoulder pain caused by rheumatoid arthritis, rotator cuff tendonitis, and osteoarthritis (Gado and Emery, 1996).

Analogously, chemical inhibition of sensory nerves can be achieved through administration of capsaicin, an analgesic that causes the release of SP from afferent nerve fibers. Capsaicin is one of the main constituents of hot, red chili peppers. Capsaicin inhibits type C cutaneous sensory fibers (Dray, 1992) and administration of capsaicin releases substance P (Jessell et al., 1978) from these fibers. Substance P depletion by capsaicin has been shown to be detrimental to wound healing (Dunnick et al., 1996; Dwyer et al., 2003). A decrease in immune cells (CD4+ and CD8+ cells) in whole blood has been shown to result from administering capsaicin (Santoni et al., 1996) to rats, which may account for poor healing of tissues following administration of capsaicin. Capsaicin, like guanethidine, has been conventionally used to treat joint disorders, including: neuralgia (Carter, 1991), surgical neuropathic pain, rheumatoid arthritis, osteoarthritis, and temporomandibular joint pain (Surh and Lee, 1996).

While techniques of inhibiting sensory information resulting from peripheral neuropathies affords relief from pain, these techniques do not treat the underlying cause of the pain, and in many instances may further potentiate the connective tissue degeneration that is the source of, or results from, pain induction.

SUMMARY OF THE INVENTION

The present invention provides methods of arresting connective tissue degeneration and provides a means of inducing increased healing of connective tissue, especially ligaments, cartilage and subchondral bone.

Thus, a first embodiment of the invention is directed to a method of treating degenerative cartilage disease and/or traumatic cartilage injury with or without subchondral bone damage in a subject in need thereof. The method comprises administering to the subject an amount of a neurogenic compound, the amount of the compound being effective to stimulate repair of the diseased and/or injured cartilage and/or the subchondral bone.

It is preferred that the administered neurogenic compound be a neuropeptide. From among the neuropeptides, the preferred neuropeptides are calcitonin gene-related peptide (CGRP), cholecystokinin (CCK), dynorphin, enkephalin, galanin, neuropeptide Y (NPY), neurotensin, somatostatin, substance P (SP), thyrotropin-releasing hormone (TRH), vasoactive intestinal peptide (VIP), and combinations thereof. The neurogenic compound can be administered neat, but is it much preferred that the compound is administered in combination with a pharmaceutically suitable carrier.

A second embodiment of the invention is a method of improving the functional properties of damaged or diseased cartilage. The method of the second embodiment comprises administering to a subject having damaged cartilage a cartilage functional property-improving and/or resistance to degradation-improving amount of a neuropeptide.

Similarly, a third embodiment of the invention is directed to a method of treating degenerative cartilage disease. The method comprises administering to the subject a cartilage functional property-improving and/or resistance to degradation-improving amount of a neuropeptide.

Similarly, a fourth embodiment of the invention is directed to a method of treating osteochondral defects. The method comprises administering to subject an amount of neuropepide(s) to facilitate repair of both subchondral bone and articular cartilage.

The invention also encompasses a pharmaceutical composition for healing damaged cartilage and osteochondral defects. The pharmaceutical composition comprises a cartilage repair-effective amount of a neurogenic compound in combination with a pharmaceutically suitable carrier. In the preferred embodiment of the composition, the neurogenic compound is a neuropeptide. It is most preferred that from among the neuropeptides, a peptide selected from the group consisting of calcitonin gene-related peptide (CGRP), cholecystokinin (CCK), dynorphin, enkephalin, galanin, neuropeptide Y (NPY), neurotensin, somatostatin, substance P (SP), thyrotropin-releasing hormone (TRH), vasoactive intestinal peptide (VIP), and combinations thereof, is contained within the pharmaceutical composition.

The methods and compositions disclosed herein are significant and beneficial for several reasons. First, cartilage healing and grafting is performed without considering the potential role of NPs. The present invention demonstrates that NPs can be beneficial to cartilage-healing and subchondral bone healing. As clearly demonstrated by the Examples contained herein, administering NPs to damaged or diseased cartilage tissue can promote or hasten a healing process. NPs in ligaments yield tissue that is as strong, if not stronger, than intact, undamaged ligaments (see Example 8). Thus, the invention has a distinct utility to promote ligament, tendon, cartilage, and bone healing. The invention is also useful to increase the functionality of intact cartilage as a low-friction, load-bearing surface, an outcome that will surely be of interest to athletes and sports doctors alike.

The invention is also useful to speed the healing of subchondral bone injuries and defects. Healing of these types of bony injuries, as well as the healing of the cartilage that overlays the bony injury itself are key to returning the affected joint to complete, pre-injury condition.

Further still, numerous prior art studies take a tissue engineering approach to regenerate connective tissues, but fail to consider the impact of peripheral nerves and NPs on the regeneration of connective tissues in general and cartilage in particular. In the present invention, tissue engineering procedures can be supplemented with pharmaceutical compositions containing neurogenic compounds both to hasten the time to complete recovery, as well as the "completeness" of the recovery itself. In short, the invention provides methods and pharmaceutical compositions to promote healing in damaged or grafted connective tissues, promotes the effects of neurogenic agents on healing tissues, and provides a means to increase the mechanical functionality and integrity of connective tissues, even in the absence of neural regeneration or stimulation.

BRIEF DESCRIPTION OF THE FIGURES

FIG. 13A presents ligament stress; FIG. 13B presents ligament strain; and FIG. 13C presents ligament modulus.

FIGS. 14A and 14B are photomicrographs showing the disappearance of SP and CGRP from Group 1 and Group 3 ligaments after capsaicin treatment. FIG. 14A: control tissue containing nerve fibers that labeled positively for SP and CGRP. FIG. 14B: capsaicin-treated MCLs devoid of SP- and CGRP-positive nerve fibers.

FIG. 15A: after 10 days, capsaicin-treated (intact) MCLs showed significantly lower concentrations of SP and CGRP. FIG. 15B: after two weeks of healing, MCLs treated with capsaicin also had reduced concentrations of SP and CGRP as compared to controls.

FIG. 20A is a representative untreated cartilage showing fibrosis both within the cartilage defect and in the underlying bone. FIG. 20B is a representative cartilage treated with substance P which displays greatly improved healing of both the cartilage and subchondral bone. FIG. 20C is uninjured cartilage and bone for comparison.

FIG. 21 depicts in histogram form the raw data presented in Table 2.

FIG. 23 depicts in histogram form the raw data presented in Table 3.

DETAILED DESCRIPTION

Figure 1:
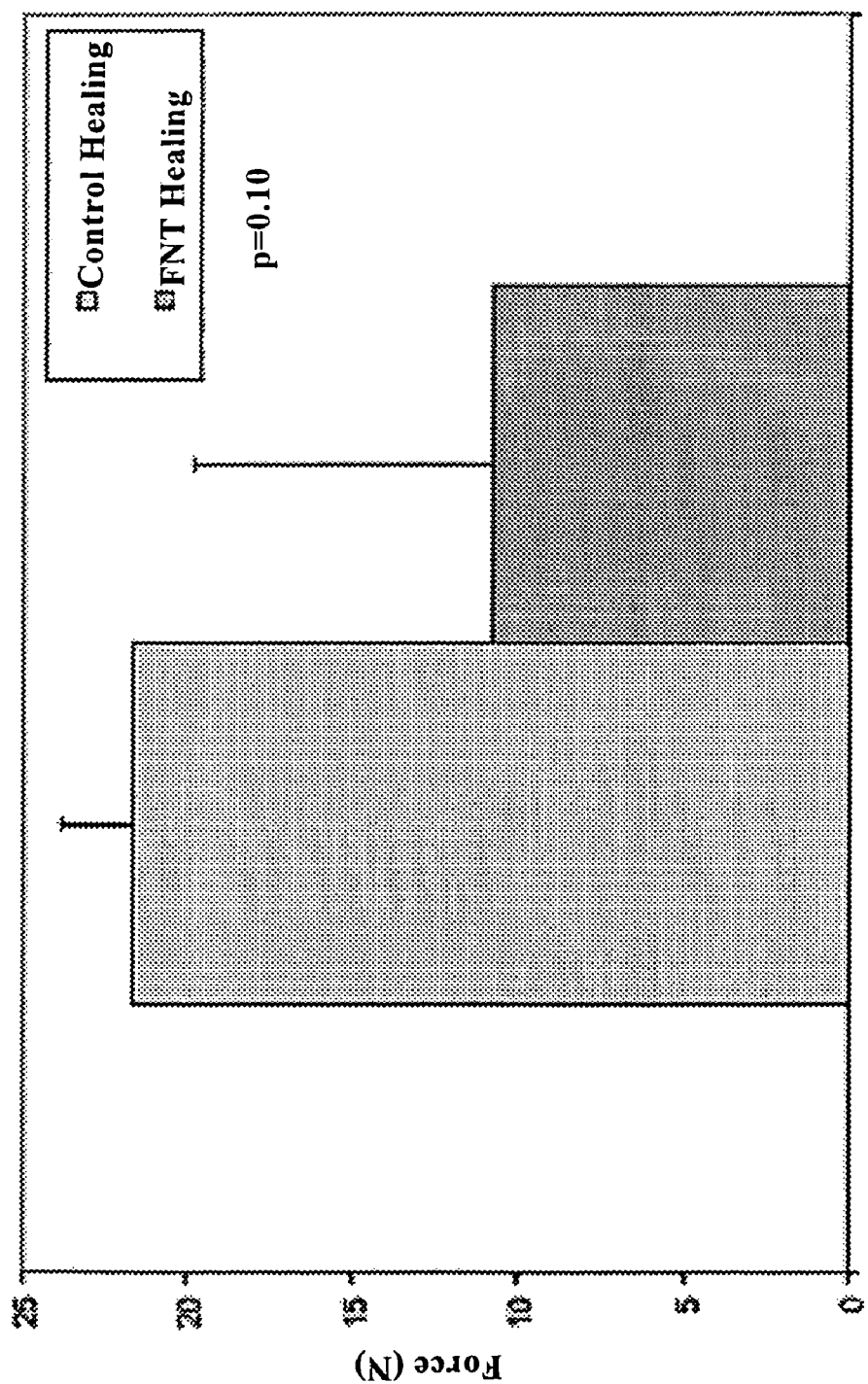
FIG. 1 is a graph depicting the ultimate stress experienced by rat MCL tissue after femoral nerve transection as compared to controls (see Example 1).

The present invention is directed to a method for treating connective tissue disease and promoting healing of connective tissues damaged from trauma and/or acute or chronic neuropathies. As described herein, connective tissue disease may be any of a number or associated disorders resulting in increased breakdown or decreased healing of primarily collagenous tissues, and may include aspects of typical peripheral neuropathies associated with diseases such as diabetes.

Damaged nerves have limited potential for regeneration. Tissue healing following peripheral nerve damage is slow and can result in permanent joint damage. Certain joint disorders are managed conventionally through surgical or drug treatments that inhibit nerve responses. Typically such treatments comprise surgical or chemical sympathectomy. While sympathectomy or other nerve-inhibiting treatments are effective in relieving pain, the potentially detrimental effects of these treatments on soft tissues has been largely unexplored until now.

For example, in conventional ligament reconstruction, denervated tissue is used as the graft. As detailed herein, the denervation of the graft hinders the healing and remodeling of the grafted area (which likely has an adverse effect on the joint proprioception). In addition, PNS disorders are prevalent and can be debilitating, yet little has been done to relate neurogenic changes to structural damage in joint tissue. Further, surgical interventions generally require rest or disuse of the affected joint. Disuse degeneration resulting from prolonged rest or disuse of damaged joints is known to be significant.

Therefore, investigations utilizing the cruciate ligaments in rats were used to examine the effect of innervation and the presence of neurogenic factors on the biomechanical properties and healing potential of those ligaments. It was also used to examine the effect of NP treatment on graft healing and on graft or soft tissue to bone healing. The results obtained indicate that peripheral autonomic and sensory nerves are extremely important for the homeostatic maintenance and healing of ligaments. While it is understood that peripheral nerves directly control the blood supply in ligament, and blood flow regulates cell metabolism, delivery of growth factors, and removal of waste products, little has been done to explore the role played by neurogenic compounds in connective tissue healing, graft tissue healing, and soft tissue to bone healing.

Thus, the invention provides methods and pharmaceutical compositions to improve the strength, healing, and functionality of connective tissue in general and ligaments, tendons, cartilage and subchondral bone in particular by administering to the connective tissue in question an amount of a neurogenic compound, preferably a neuropeptide.

The present invention encompasses pharmaceutical compositions for treating damaged ligaments, tendons, cartilage and subchondral bone, for improving healing of these tissues, for improving the strength of these tissues, and the like. The pharmaceutical compositions comprise an amount of neurogenic compound, preferably one or more neuropeptides, or pharmaceutically suitable salts thereof, in an amount effective, for example, to stimulate repair of diseased or damaged cartilage. In the preferred formulations, the neurogenic compound (or a salt thereof) is admixed with a pharmaceutically suitable carrier, such as a sterile saline solution that is isotonic with the blood of the recipient.

As used herein, the term "pharmaceutically suitable salt" refers to any acid or base addition salt whose counter-ions are non-toxic to the patient in pharmaceutical doses of the salts (i.e., so that the beneficial ligament-healing effects inherent in the free base or free acid are not vitiated by side effects ascribable to the counter-ions). A host of pharmaceutically suitable salts are well known in the art. For example, for basic active ingredients, all acid addition salts are useful as sources of the free base form even if the particular salt, per se, is desired only as an intermediate product as, for example, when the salt is formed only for purposes of purification, and identification, or when it is used as intermediate in preparing a pharmaceutically-suitable salt by ion exchange procedures.

Pharmaceutically suitable salts include, without limitation, those derived from mineral acids and organic acids, explicitly including hydrohalides, e.g., hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyl-tartrates, methane-sulphonates, ethanesulphonates, benzene-sulphonates, p-toluenesulphonates, cyclohexylsulphamates, quinates, and the like.

Base addition salts include those derived from alkali or alkaline earth metal bases or conventional organic bases, such as triethylamine, pyridine, piperidine, morpholine, N-methylmorpholine, and the like.

Pharmaceutical formulations of the present invention comprise an active compound(s), i.e., a neurogenic compound(s), a neuropeptide, etc., or salt thereof, together with a pharmaceutically-acceptable carrier therefor and optionally other therapeutically-active ingredients. The carrier must be pharmaceutically-acceptable in the sense of being compatible with the other ingredients of the formulation and not deleterious to the recipient thereof.

The pharmaceutical formulations encompassed by the present invention include those suitable for oral, topical, rectal or parenteral (including subcutaneous, intramuscular, intra-joint, and intravenous) administration. Preferred are those suitable for subcutaneous, intramuscular, and intra-joint administration.

The formulations may conveniently be presented in unit dosage form and may be prepared by any of the methods well known in the art of pharmacy. All such methods include the step of bringing the active neurogenic compound into association with a carrier which constitutes one or more accessory ingredients. In general, the formulations are prepared by uniformly and intimately bringing the active compound into association with a liquid carrier (or a finely divided solid carrier) and then, if necessary, shaping the product into desired unit dosage form.

Formulations of the present invention suitable for oral administration may be presented as discrete units such as capsules, cachets, tablets, boluses or lozenges, each containing a predetermined amount of the active neurogenic compound; as a powder or granules; or in liquid form, e.g., as a suspension, solution, syrup, elixir, emulsion, dispersion, and the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulations suitable for parenteral administration conveniently comprise a sterile preparation of the active compound in, for example, a polyethylene glycol 200 solution, a propylene glycol solution, or a simple saline solution (all of which are preferably isotonic with the blood of the recipient).

Useful formulations also comprise concentrated solutions or solids containing one or more active neurogenic compounds, which upon dilution with an appropriate solvent yields a solution suitable for parenteral administration.

Preparations for topical or local applications, comprise aerosol sprays, lotions, gels, ointments, etc. and pharmaceutically-acceptable vehicles therefore, such as lower aliphatic alcohols, polyglycerols, esters of fatty acids, oils and fats, silicones, and other conventional topical carriers.

In topical formulations, the active neurogenic compounds are preferably utilized at concentrations of from about 0.1% to about 5.0% percent by total weight of the topical formulation.

In addition to the aforementioned ingredients, the formulations of this invention may further include one or more optional accessory ingredient(s) utilized in the art of pharmaceutical formulations, e.g., diluents, buffers, binders, surface active agents, thickeners, lubricants, suspending agents, preservatives (including antioxidants) and the like.

The amount of the neurogenic compound required to be effective for the indicated activity will, of course, vary with the individual mammal being treated and is ultimately at the discretion of the medical or veterinary practitioner, as noted above. As a general proposition, neurogenic compounds exert their pharmacological effects at exceedingly low concentrations. Thus, a suitable effective dose is in the range of about 1 pg to about 10 μg per day, preferably in the range of about 10 pg to about 500 pg per day, and more preferably about 10 pg to about 100 pg per day. The total daily dose may be given as a single dose, multiple doses, e.g., two to six times per day, in a timed release formulation or by intravenous infusion for a selected duration (see the Examples). Dosages above or below the range cited above are within the scope of the present invention and may be administered to the individual patient if desired and necessary.

EXAMPLES

The following Examples are included to provide a more complete and thorough description of the invention disclosed and claimed herein. The Examples do not limit the scope of the invention in any fashion.

Example 1

Femoral Nerve Transection Impairs Healing in a Rat MCL Model

As noted earlier, ligament healing is a complex problem that is influenced by inflammatory responses, extracellular matrix remodeling, and chemical mediators. The role of neurogenic factors in general, and neuropeptides in particular, in ligament healing remains undefined. The purpose of this Example was to investigate the role of sensory nerves on MCL healing in a neuropathic rat model.

Surgical Procedure: Thirteen female Wistar rats (278 g to 315 g) were divided into two groups: femoral nerve transection (FNT) or sham control. All rats were anesthetized with isofluorane (isofluorane 0.5-3%). Anesthesia was initiated in an induction chamber and maintained with a facemask. Skin covering the anterior inguinal region was shaved and prepared for surgery. A skin incision approximately 15 mm long was made and the fascia distal to the inguinal was incised. The femoral artery, vein, and nerve were exposed and the femoral nerve was isolated and transected (with removal of a 5 mm segment of the nerve) using 3-0 dexon suture. The fascia and skin were closed in two layers with 3-0 continuous dexon suture. Immediately following FNT, rats from each group (n=4 FNT; n=3 controls) underwent a complete surgical rupture of the MCL to one knee. The contra-lateral knee underwent sham surgery. Two weeks post-knee surgery, rats were sacrificed using an overdose of pentobarbitone (150 mg/kg).

Mechanical Testing: All rats with ruptured MCLs underwent mechanical testing (n=4 FNT; n=3 control) of the healing MCLs. Briefly, animal hind limbs from all groups (n=4 FNT and n=3 control) were disarticulated at the hip joint and stored at −80° C. until testing. Immediately following death, rats were stored at −80° C. until testing. On the day of testing, rat hind limbs were thawed at room temperature. The MCL of each leg was exposed and extraneous tissue was carefully dissected from the joint. MCLs, including intact femoral and tibial bone sections (FMT complex) were excised for ex vivo testing. The ligament area was then measured optically.

The FMT complex was then mounted into a custom-designed bath and optical markers were placed on the MCL near the insertion sites. Ligaments were preloaded (0.1 N) and preconditioned (1% strain for 10 cycles). Following preconditioning, ligaments were pulled to failure at a rate of 10% per second. Tissue force and displacement were recorded and ultimate stress and failure strain were calculated. Tissue displacement was obtained using video dimensional analysis and equations (1) and (2) presented in Example 4. The mechanical properties that were examined in this study were maximum force, ultimate stress, strain at failure, elastic modulus, and area. Statistical analysis was performed using an unpaired t-test (alpha=0.05) to compare differences between the control and treatment groups.

Immunofluorescence: Rats that did not receive MCL rupture were used for immunofluorescence (n=3 FNT; n=3 control). MCLs were removed in toto and were fixed in 4% paraformaldehyde for 1 hour. Whole ligament specimens were blocked with serum and incubated overnight with primary antibody to the neuropeptides SP (1:2000 dilution), calcitonin gene-related peptide (CGRP; 1:2000 dilution), neuropeptide Y (NPY; 1:10,000 dilution) or vasoactive intestinal peptide (VIP; 1:1000 dilution). All antibodies were from Chemicon, Temecula, Calif. Tissue was incubated with a fluorescent probe-secondary antibody conjugate (AMCA or Rhodamine; Chemicon, Temecula, Calif.) and specimens were examined using a confocal microscope (MRC 600, Bio-Rad). Images were viewed in the plane of focus, and scanned through the tissue depth (z-plane) so that three-dimensional reconstructions could be made by stacking the sequentially scanned images. Images were then viewed with a computer and saved digitally.

Radioimmunoassay (RIA): MCLs used in the mechanical testing protocol were also used for quantification of neuropeptide concentrations via RIA. MCLs were homogenized using a mortar and pestle. Homogenate was used to complete a standard SP, CGRP, NPY, and VIP RIA protocol (Phoenix Pharmaceuticals, Belmont, Calif.). Briefly, samples were mixed with an antibody specific to one of the neuropeptides, then incubated with a $^{125}$I-traced peptide. Measurements of the gamma radioactivity of each sample were determined using a gamma counter. Standards for each neuropeptide were included in the kit. The MCL neuropeptide concentration was determined from a standards curve.

Tissue Histomorphology: Immediately following death, three MCLs from each group were exposed and dissected in toto from the tibial and femoral insertions. Ligaments were immediately fixed in formalin fixative for three days at room temperature. Specimens were embedded in paraffin, sectioned (6 μm), mounted on slides, and stained with hematoxylin and eosin (H&E).

Figure 2:
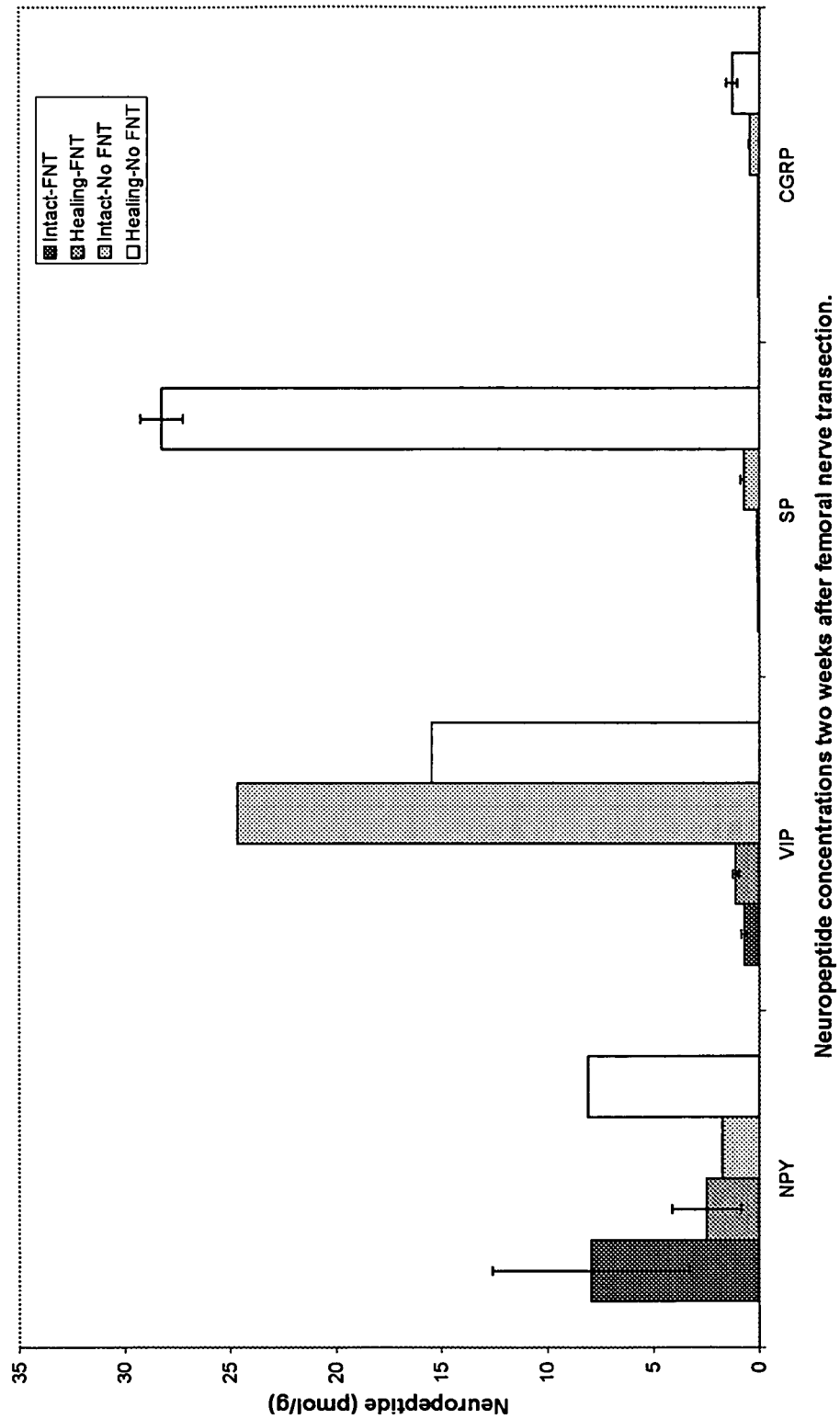
FIG. 2 is a graph depicting neuropeptide concentrations (NPY, VIP, SP, and CGRP) in rat MCL tissue following femoral nerve transection as compared to controls (see Example 1).

Results: Within minutes of surgical intervention, all rats recovered and had normal movement and behavior (grooming, feeding, etc.). There were no differences in sacrifice weights between control and FNT groups. Mechanical testing showed FNT MCLs had lower failure force (10.8±9.0 vs. 21.6±2.2 N; p=0.10; Student's t-test) and ultimate stress (7.6±6.3 vs. 14.3±2.7 MPa; p=0.10; Student's t-test) following two weeks of healing as compared to healing controls. No differences were seen between the MCL area or failure strain. From immunofluorescent data (FIG. 1) and RIA data (FIG. 2), neuropeptides associated with sensory nerves, SP and CGRP, were reduced in FNT MCLs. Little change was seen in NPY, however VIP was also reduced.

Immunofluorescent labeling of neuropeptides revealed a disappearance of SP and CGRP from femoral nerve transected ligaments. Similarly, there was a reduction of VIP and NPY from surgical sympathectomized MCLs. RIA data confirmed these results. Data for each group is shown in Table 1.

TABLE 1

RIA Data for Intact and Healing Neuropathic MCLs.

| | VIP (pmol/g) | NPY (pmol/g) | SP (pmol/g) | CGRP (pmol/g) |
|---|---|---|---|---|
| SS Healing | 0.04 ± 0.001*+ | 0.16 ± 0.037*+ | 30.01 ± 0.148 | 1.04 ± 0.039 |
| SS Intact | 0.03 ± 0.001+ | 0.083 ± 0.06+ | 14.36 ± 10.51 | .962 ± 0.112+ |
| FNT Healing | 1.11 ± 0.135*+ | 2.43 ± 1.60* | 0.10 ± 0.015*+ | 0.04 ± 0.01*+ |
| FNT Intact | 0.708 ± 0.14+ | 7.94 ± 4.61+ | 0.9 ± 0+ | 0.04 ± 0.01+ |
| Normal Healing | 15.5 ± 0.015 | 7.84 ± 0.12 | 28.19 ± 1.00 | 1.30 ± 0.250 |
| Normal Intact | 24.7 ± 0.016 | 1.72 ± 0.011 | 0.70 ± 0..152 | .045 ± 0.043 |

+ Data significantly different from intact MCL.
*Data significantly different from healing MCL.

Figure 19A:
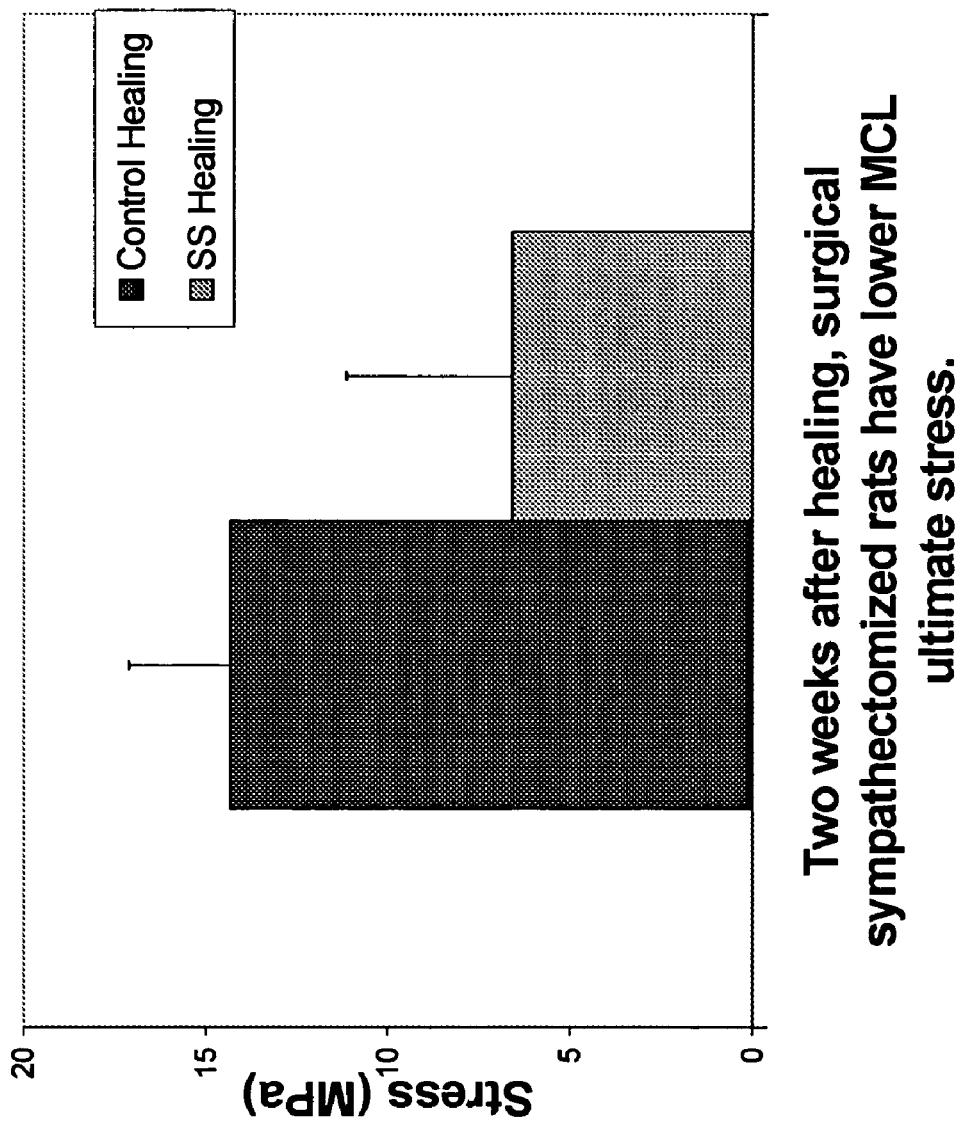
FIGS. 19A and 19B are graphs depicting the failure force of sympathectomized MCLs (FIG. 19A) and the failure force of femoral nerve transected MCLs (FIG. 19B). The graphs show that peripheral neuropathy decreases the failure force of healing MCLs.
Figure 19B:
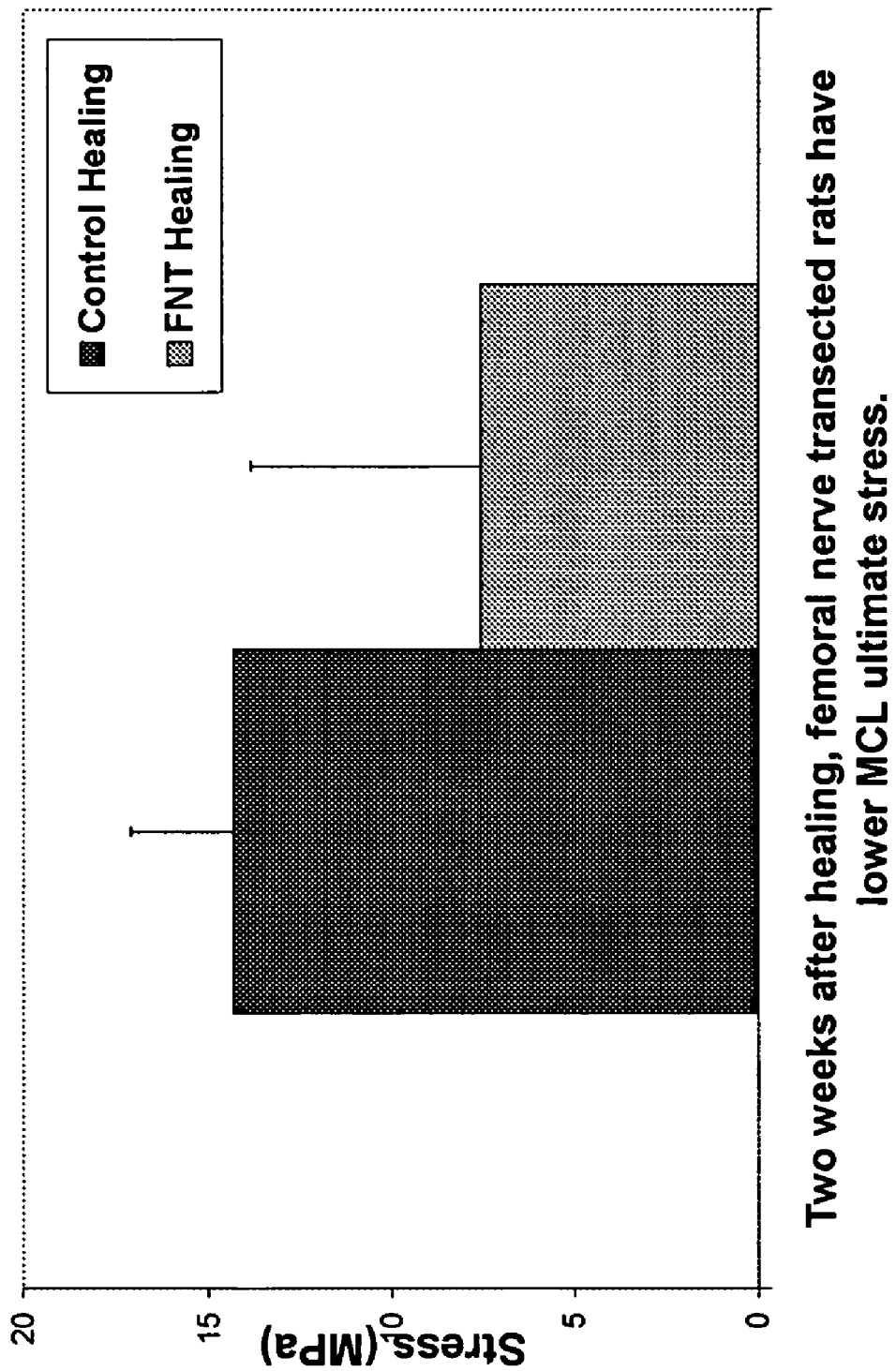

MCL Mechanics: There were no changes in failure force, ultimate stress, failure strain, area, and elastic modulus in intact neuropathic MCLs (SS or FNT) when compared to intact controls. These data suggest that nerve damage alone has little effect on intact ligamentous structures. In healing MCLs, the failure force was significantly reduced in both neuropathic groups. Surgical sympathectomized healing MCLs had significantly lower failure force compared to normally innervated healing MCLs (21.6±2.2 N vs. 9.6±6.7 N; p=0.04; see FIG. 19A). In femoral nerve transected healing MCLs, the failure force was also reduced, but this result was not statistically significant (21.6±2.2 N vs. 10.8±9.0 N; p=0.10; see 19B).

The changes observed in ultimate stresses followed the same trend. Surgical sympathectomized healing MCLs had significantly lower ultimate stress compared to normally innervated healing MCLs (14.3±2.7 MPa vs. 6.6±4.5 MPa; p=0.039). In femoral nerve transected healing MCLs, the ultimate stress was also reduce, but this result was not statistically significant (14.3±2.7 MPa vs. 7.6±6.3 N; p=0.10). No significant changes were seen in any other mechanical properties investigated. Hence, after only 2 weeks of healing, surgical neuropathy had a little effect on homeostasis of intact MCLs, but had a significant impact on MCL healing. Histomorphology: H&E staining revealed that healing MCLs from all groups are hypercellular and have highly disorganized extracellular matrix through the injury site following two weeks of healing.

This Example shows that: 1) sensory nerves influence MCL healing; 2) ligament strength is significantly decreased in animals subjected to FNT; and 3) the concentration of the neuropeptides SP, CGRP, and VIP are significantly reduced in the ligaments of an animal model (rats) subjected to FNT. Taken as a whole, these data clearly suggest that neuropeptides play a key role in ligament healing and ligament strength.

Example 2

Surgical Sympathectomy Impairs Healing in a Rat MCL Model

The purpose of this Example was to investigate the role of sympathetic nerves on MCL healing in another rat model.

Surgical Procedure: Thirteen female Wistar rats (306 g to 339 g) were divided into two groups: surgical sympathectomy (SS) or sham control. All rats were anesthetized with isofluorane as described in Example 1. A transperitoneal approach was used. The lower abdomen was shaved and prepared for surgery. A skin incision approximately 25 mm long was made. Fascia and abdominal muscle were incised. Abdominal organs were displaced. With the aid of a dissecting microscope, fascia surrounding the deep muscle tissue was separated (with minimal disruption to the muscle tissue) to expose the post-ganglionic sympathetic nerves. The L1-4 nerves were isolated and transected (with removal of a 5 mm segment of the nerves) in the surgical sympathectomy group only. In both groups, the deep muscle tissue was returned to its initial position and abdominal organs were replaced. Abdominal muscles and skin were closed in two layers with a 3-0 or 4-0 continuous dexon suture. Rats from each group (n=4 SS; n=3 controls) then underwent a complete surgical rupture of the MCL to one knee. The contra-lateral knee underwent sham surgery. All rats showed normal recovery, ambulation, grooming, and feeding following these procedures. Two weeks post-surgery, rats were sacrificed using an overdose of pentobarbitone (150 mg/kg).

Mechanical Testing: All rats with ruptured MCLs underwent mechanical testing (n=4 SS; n=3 control) of the healing MCLs as follows. Briefly, animal hind limbs from all groups (n=4 FNT and n=3 control) were disarticulated at the hip joint and stored at −80° C. until testing.

Immediately following death, rats were stored at −80° C. until testing. On the day of testing, rat hind limbs were thawed at room temperature. The MCL of each leg was exposed and extraneous tissue was carefully dissected from the joint. MCLs, including intact femoral and tibial bone sections (FMT complex) were excised for ex vivo testing. The ligament area was then measured optically.

The FMT complex was then mounted into a custom-designed bath and optical markers were placed on the MCL near the insertion sites. Ligaments were preloaded (0.1 N) and preconditioned (1% strain for 10 cycles). Following preconditioning, ligaments were pulled to failure at a rate of 10% per second as described in Example 1. Tissue force and displacement were recorded and ultimate stress and failure strain were calculated. Tissue displacement was obtained using video dimensional analysis and equations (1) and (2) presented in Example 4. The mechanical properties that were examined in this study were maximum force, ultimate stress, strain at failure, elastic modulus, and area. Statistical analysis was performed using an unpaired t-test (alpha=0.05) to compare differences between the control and treatment groups. Tissue force and displacement were recorded and ultimate stress and failure strain were calculated.

Immunofluorescence: Rats that did not receive MCL rupture were used for immunofluorescence (n=3 SS; n=3 control), which was conducted in the same fashion as described in Example 1.

Radioimmunoassay (RIA): MCLs used in the mechanical testing protocol were also used for quantification of neuropeptide concentrations via RIA using the same protocol as described in Example 1. Briefly, MCLs were homogenized using a mortar and pestle. Homogenate was used to complete a standard SP, CGRP, NPY, and VIP RIA protocol (Phoenix Pharmaceuticals, Belmont, Calif.). Briefly, samples were mixed with an antibody specific to one of the neuropeptides, then incubated with a $^{125}$I-traced peptide. Measurements of the gamma radioactivity of each sample were determined using a gamma counter. Standards for each neuropeptide were included in the kit. The MCL neuropeptide concentration was determined from a standards curve.

Figure 3:
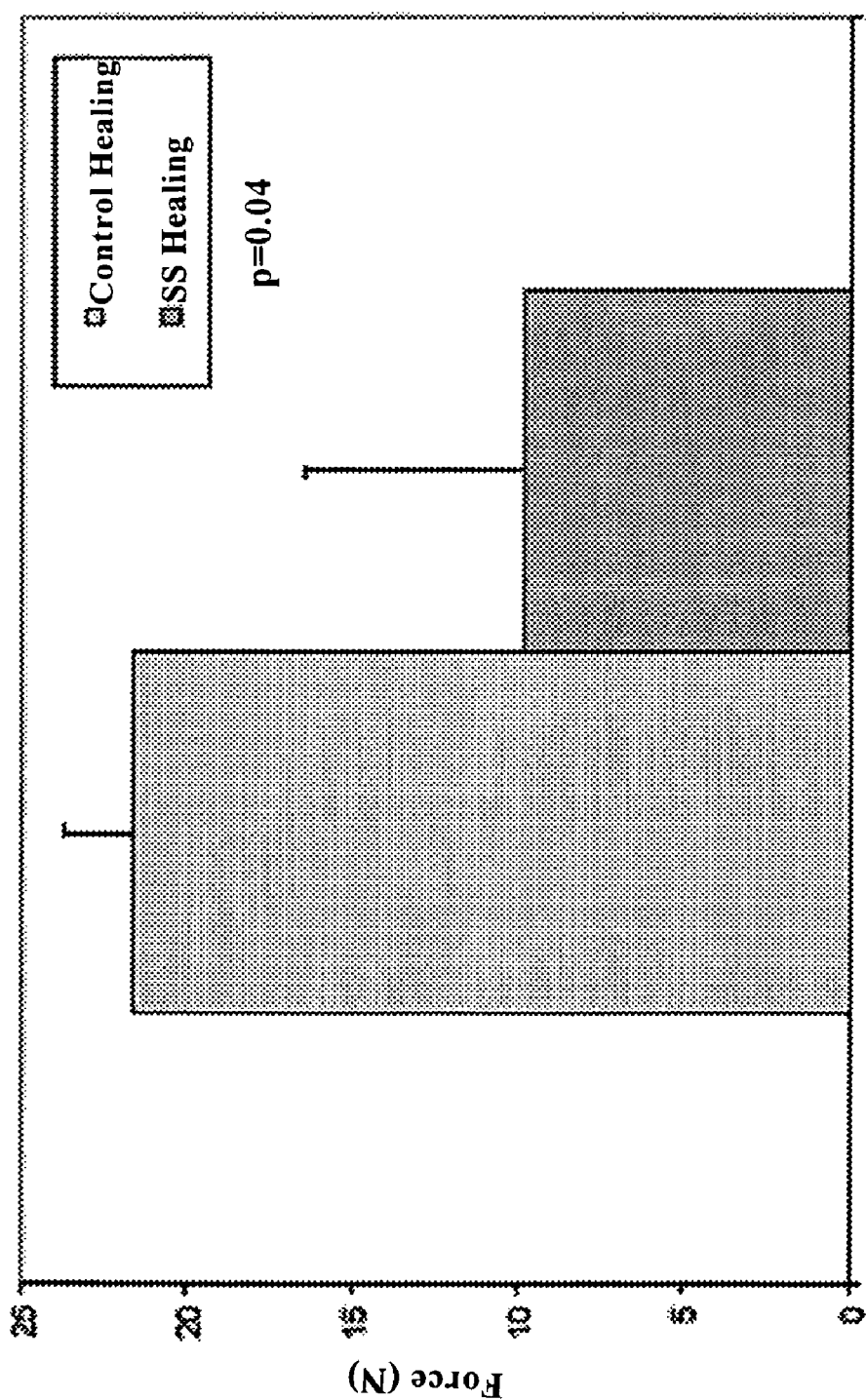
FIG. 3 is a graph depicting the ultimate stress experienced by rat MCL tissue after surgical sympathectomy as compared to controls (see Example 2).
Figure 4:
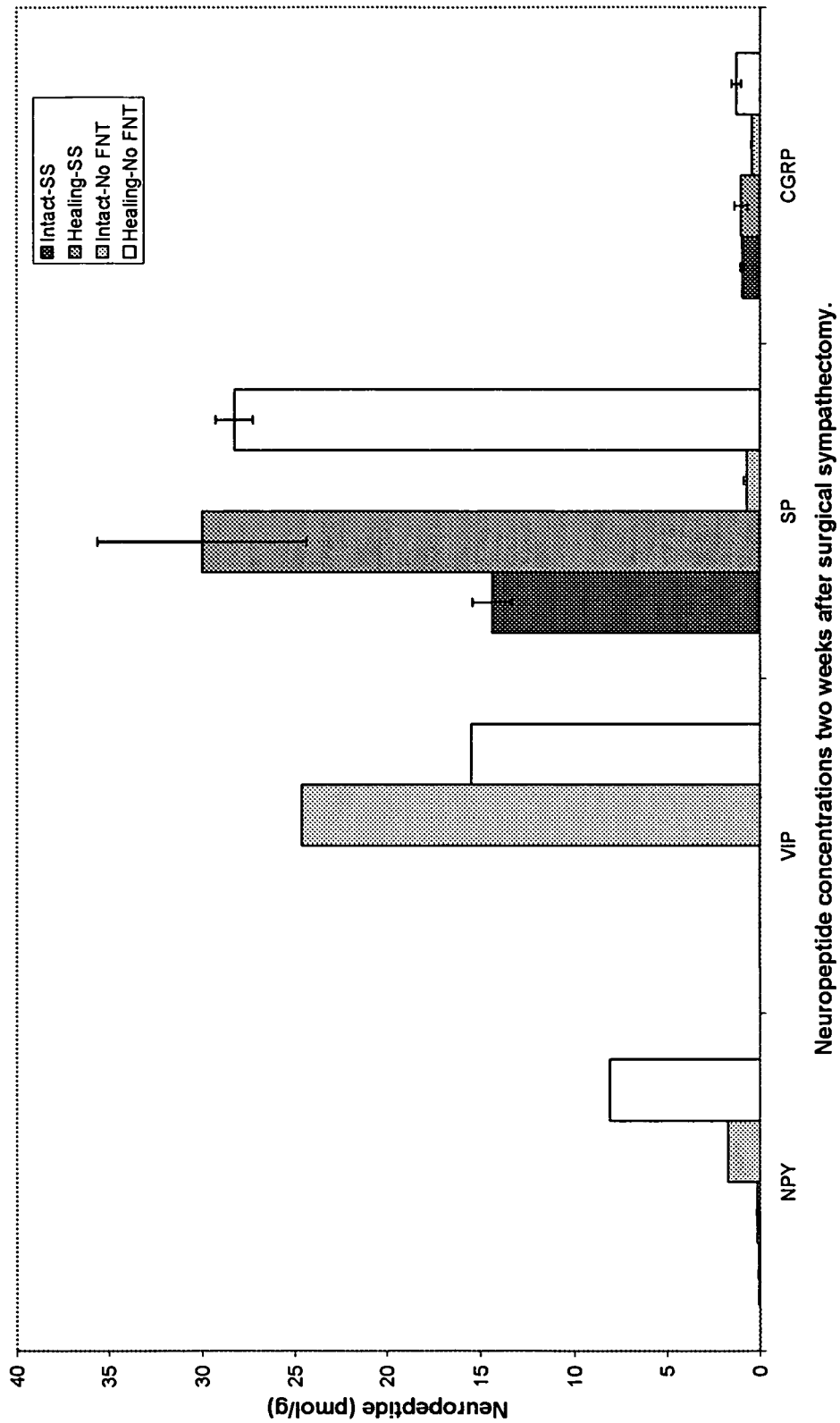
FIG. 4 is a graph depicting neuropeptide concentrations (NPY, VIP, SP, and CGRP) in rat MCL tissue following surgical sympathectomy as compared to controls (see Example 2).

Results: Within minutes of surgical intervention, all rats recovered and had normal movement and behavior (grooming, feeding, etc.). There were no differences in sacrifice weights between control and SS groups. Mechanical testing showed SS MCLs had lower failure force (21.6±2.1 vs. 9.8±6.7 N; p=0.040; Student's t-test) and ultimate stress (14.3±2.7 vs. 6.6±4.5 MPa; p=0.039; Student's t-test) following two weeks of healing when compared to healing controls. No differences were seen between the MCL area or failure strain. From immunofluorescence data (FIG. 3) and RIA data (FIG. 4), neuropeptides associated with sympathetic nerves, NPY and VIP, were reduced in SS MCLs. No changes were seen in SP or CGRP concentrations.

To the inventors' knowledge, this Example is the first to show that sympathetic innervation plays a role in ligament healing. The Example clearly indicates that concentrations of the neuropeptides NPY and VIP are reduced in the ligaments of rats subjected to SS. Moreover, the rats subjected to SS had significantly lower failure force values and ultimate stress values as compared to controls. In short, this Example shows that decreased levels of the neurogenic compounds NPY and VIP are detrimental to ligament healing and overall ligament strength.

Example 3

Local Delivery of Neuropeptides

Local delivery of NPs and NP inhibitors is important to identify the specific roles of individual NPs on healing tissues. An animal model for the local delivery of NPs has been developed and is presented in this Example. Briefly, NP infused mini-osmotic pumps were implanted subcutaneously into the back of rats. A small catheter running from the pump to an intramuscular space above the MCL was secured to the rat.

Figure 5:
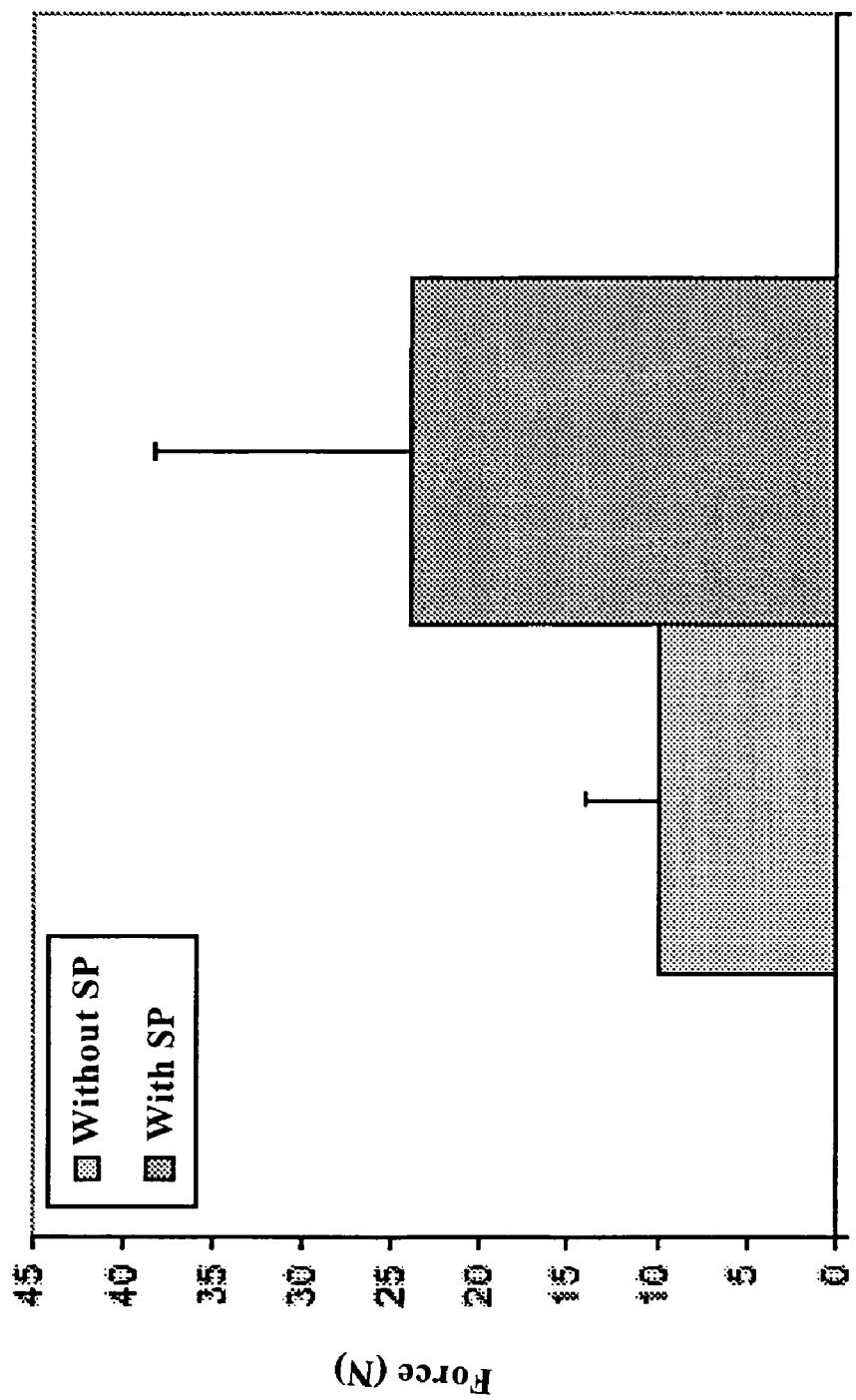
FIG. 5 is a graph depicting the failure force tolerated by healing rat MCL in the presence and absence of supplemental SP, two weeks post-rupture (see Example 3).

To test whether sensory NPs improve healing in femoral nerve transection (FNT) ruptured MCLs, three female Wistar rats (199 g to 203 g) were given SP locally to the MCL. Substance P (103 pg/µl) was infused into a miniosmotic pump and was delivered to a ruptured MCL of a FNT rat (see surgical procedure in Example 1 above). Within minutes of surgical intervention, all rats recovered and had normal movement and behavior (grooming, feeding, etc.). Mechanical testing showed SP-supplemented FNT MCLs had a much greater failure force (74.3 vs. 23.4 N; p=0.001; Student's t-test) and ultimate stress (72.33 vs. 20.9 MPa; p=0.03; Student's t-test) following two weeks of healing when compared to healing without SP. The results are presented graphically in FIG. 5

Figure 6:
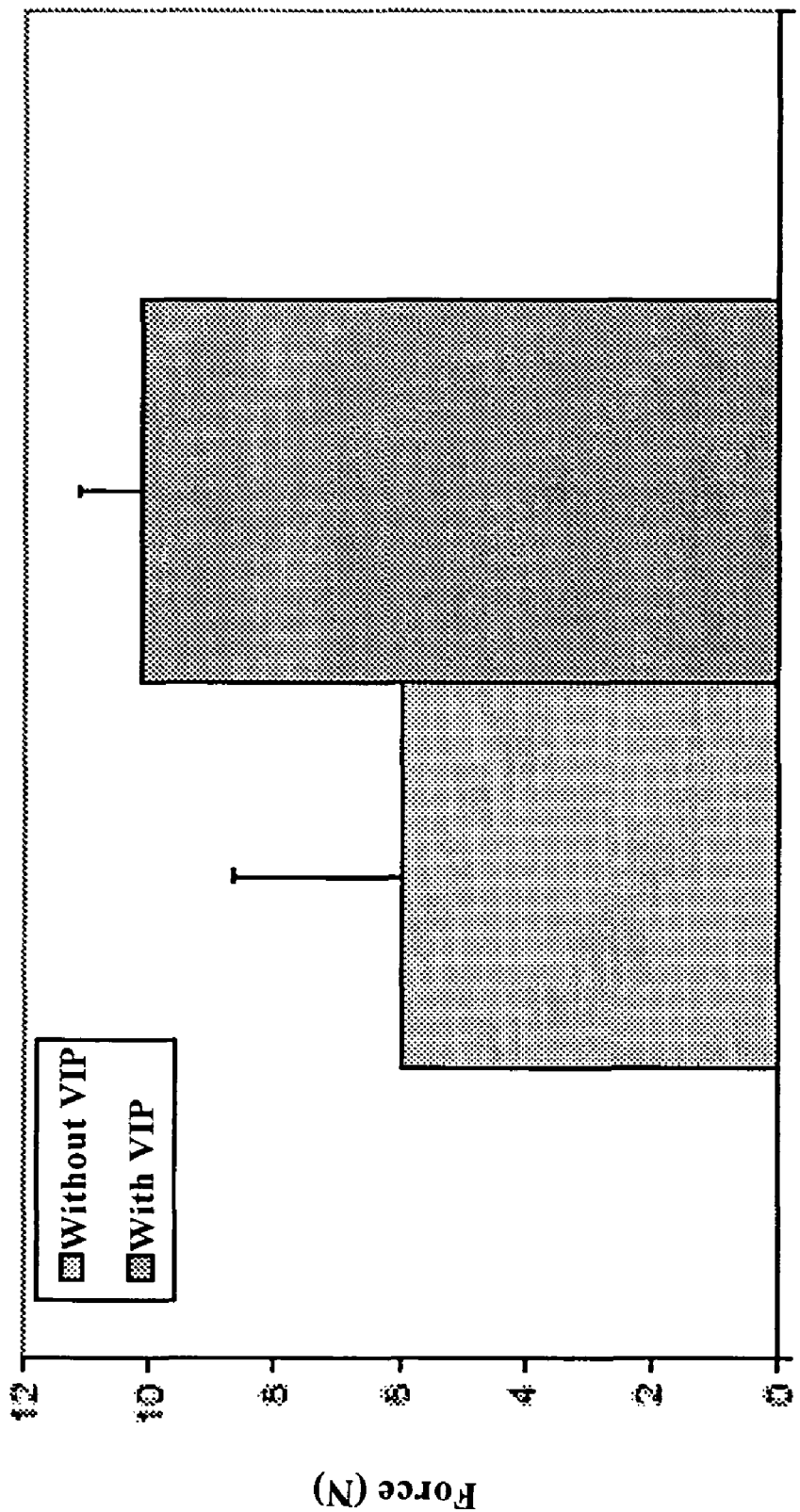
FIG. 6 is a graph depicting the failure force tolerated by healing rat MCL in the presence and absence of supplemental VIP, two weeks post-rupture (see Example 3).

To test whether autonomic NPs improve healing in SS-ruptured MCLs, three female Wistar rats (193 g to 204 g) were given VIP locally to the MCL. Vasoactive intestinal peptide (75 pg/µl) was infused into a mini-osmotic pump and was delivered to a ruptured MCL of a surgical sympathectomy (SS) rat (see surgical procedure above). Within minutes of surgical intervention, all rats recovered and had normal movement and behavior (grooming, feeding, etc.). Mechanical testing showed VIP-supplemented SS MCLs had a much greater failure force (44.23 vs. 19.37 N; p=0.005; Student's t-test) and ultimate stress (29.63 vs. 10.12 MPa; p=0.07; Student's t-test) following two weeks of healing when compared to healing without VIP. The results are presented graphically in FIG. 6.

Figure 7:
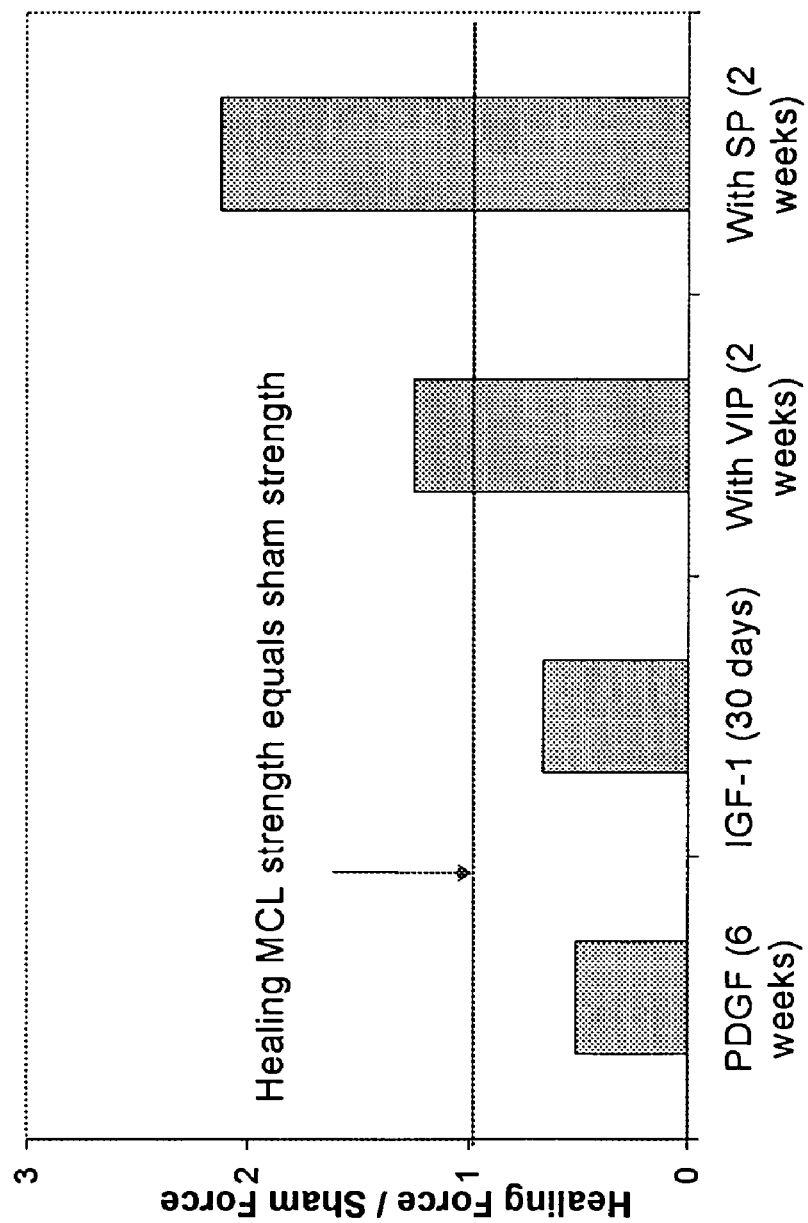
FIG. 7 is a graph depicting the failure force tolerated by healing rat MCL in the presence of various growth factors (PDGF and IGF-1) as compared to in the presence of neurogenic compounds (VIP and SP) (see Example 3)

The effects of these neuropeptides are dramatic when compared to the results of MCL healing supplemented with growth factors. Woo et al. showed that platelet-derived growth factor (PDGF)-supplemented MCLs healed to 50% of intact ligament strength after 6 weeks of healing. Provenzano et al. have shown better healing (66% the strength of intact ligament) following 30 days of insulin-like growth factor-1 delivery. In this Example, SP and VIP improved healing MCL strength to levels greater than the strength of uninjured MCLs after only 2 weeks of healing. See FIG. 7 for a graphic presentation of the results.

This Example is highly significant in that it demonstrates that neurogenic compounds can be used to improve the healing of ligament tissue.

Example 4

Effects of Guanethidine on Ligaments

This Example was conducted to determine the effect of guanethidine treatment on ligaments. Briefly, thirty female Wistar rats (207.4±13 g) were divided into two groups: 1) guanethidine-treated; and 2) saline control. For all groups, anesthesia (isofluorane 0.5-3%) was initiated in an induction chamber and maintained with a facemask. Into the treated group (n=15 animals), guanethidine (40 mg/kg/day) was infused via a subcutaneously implanted mini-osmotic pump (Alza Corp.). Into the control group (n=15 animals), a similar volume of sterile saline was infused via the same method. Both groups were survived for 10 days following implantation of the pump at which time the animals were euthanized with intraperitoneal injection of pentobarbitone. Throughout the study only one ligament per animal was used for a particular experimental test protocol (described below).

To test the effectiveness of guanethidine on sympathetic blockade, plasma concentrations of norepinephrine (NE; a major sympathetic neurotransmitter) were measured in each rat. Blood samples from each rat were taken, immediately preceding sacrifice. Plasma was separated from whole blood samples by centrifugation. Norepinephrine was then measured for each rat using a NE enzyme linked immunosorbent assay (ELISA) kit (IBL-Hamburg Inc.). Analysis was performed following the manufacturer's instructions. Briefly, ELISA plates coated in primary antibody were used for the analysis. Norepinephrine standards or plasma samples from each rat were added to the wells of the plates and allowed to incubate at room temperature for two hours. Plates were washed, and an enzyme conjugate was applied for 90 minutes. Following a second wash, Amplification Reagent was added to the wells and the absorbance values were determined for each well. The norepinephrine concentration of each sample was determined from a standards curve. Statistical analysis was performed using an unpaired t-test (alpha=0.05) to compare differences between the control and treatment groups.

Neuropeptide Radioimmunoassay: Four MCLs were used for quantification of neuropeptide concentrations via radioimmunoassay (RIA). MCLs were homogenized using a mortar and pestle. Homogenate was used to complete standard SP, CGRP, NPY, and VIP RIA protocols (Phoenix Pharmaceuticals, Belmont, Calif.). Briefly, samples were mixed with an antibody specific to one of the neuropeptides, and then incubated with a $^{125}$I-traced peptide. The radioactivity of each sample was measured using a gamma counter. Standards for each neuropeptide were included in the kit and MCL neuropeptide concentration was determined from a standards curve. Statistical analysis was performed using ANOVA (alpha=0.05) to compare differences between the treatment groups Immunofluorescent Evaluation of Neuropeptides: Immediately following death, eight MCLs (from 4 treated, 4 control rats) were exposed and dissected in toto from the tibial and femoral insertions. Ligaments were immediately fixed in 4% formalin for 24 hours. Ligaments were washed in PBST (PBS plus 1.0% Tween 20) between incubations. Ligaments were either co-incubated in a rabbit anti-rat primary antibody for NPY (1:10000 dilution) and VIP (1:1000 dilution), or SP (1:2000 dilution) and CGRP (1:2000 dilution) (all antibodies Chemicon, Temecula, Calif.). Each ligament was then incubated in two goat anti-rabbit fluoresently tagged (1:50 dilution of AMCA or Rhodamine; Chemicon, Temecula, Calif.) secondary antibodies. Confocal microscopy was used to examine the sections for fluorescent labeling. Ligaments were viewed in sagittal planes of focus, and scans were made through the ligament thickness. Three-dimensional reconstructions were made from individual confocal images by stacking the sequentially scanned images. Images were then viewed with a computer and saved digitally.

Plasma concentrations of norepinephrine (an indicator of sympathetic nerve function), as measured by enzyme-linked immunoassay (ELISA), were significantly lower in the treated group than in control animals (0.1717 ng/ml vs. 6.272 ng/ml; p=0.04), indicating significant inhibition of the sympathetic nervous system in the treated group. Immunofluorescent labeling of NPs and RIA data (performed as described in the previous Examples) revealed a disappearance of VIP and a decrease in NPY from ligament tissue after guanethidine treatment. This result indicates impairment to the autonomic neuropeptides.

Organ Culture: In order to assess the effect of guanethidine directly on extracellular matrix integrity, organ culture using the MCL was employed. Bilateral MCLs (n=6) including intact femoral and tibial segments were aseptically harvested from untreated rats. The left knee was used as a control tissue while the right knee was cultured with guanethidine.

During and after harvest, tissues were rinsed in sterile phosphate buffered saline (PBS) containing penicillin (100 U/mL), streptomycin (100 µg/mL), and fungizone (0.25 µg/mL). Bone blocks were trimmed in order to minimize the amount of bone marrow, which may alter the culture environment. Tissues were then cultured in Dulbecco's Modified Eagle's Medium (DMEM) supplemented with 10% fetal bovine serum, nonessential amino acids (0.1 mM), L-gutamine (4 mM), penicillin (100 U/mL), streptomycin (100 µg/mL), and fungizone (0.25 µg/mL). Guanethidine or sterile PBS was added to media for the treated and control tissues, respectively. The concentration of guanethidine in media was selected to be the same as the concentration of guanethidine present in the blood during treatment using normative rat data for blood volume (5 mL blood/100 g body weight). Guanethidine was prepared and dissolved in sterile PBS and added to the media, controls received equal volumes of sterile PBS. The cultures were maintained in an incubator at 37° C. and 5% $CO_2$. Media were changed every 48 hours at which time tissues were rinsed with sterile PBS to reduce drug carryover into the fresh media containing the treatment drug or equivalent volume of carrier. Organ culture was maintained for 10 days after which time the MCLs were tested mechanically in the same manner as the in vivo treatment group (described below).

Mechanical Testing: Immediately after death, animal hindlimbs for biomechanical testing (n=8 control, n=8 treated MCLs) were disarticulated at the hip joint and stored at −80°

C. until testing. Storage by freezing does not significantly affect the biomechanical properties of ligament. On the day of testing, hindlimbs were thawed at room temperature and tissue harvest and testing were performed using methods similar to those previously published, e.g. in Provenzano, P. P., et al., "Subfailure damage in ligament: a structural and cellular evaluation." *Journal of Applied Physiology*, 2002. 92(1): p. 362-71; Dwyer, K. W., et al., "Blockade of the sympathetic nervous system degrades ligament in a rat MCL model." *J Appl Physiol*, 2004. 96: p. 711-718). Each MCL was exposed by carefully dissecting extraneous tissue. The MCLs including intact femoral and tibial bone sections were excised for ex vivo testing with care taken not to disturb the ligament insertion sites. Tissues were kept hydrated in Hank's physiologic solution during testing. Ligament thickness and width was measured optically, and MCL area was estimated with elliptical geometry. Each femur-MCL-tibia (FMT) complex was then placed in a custom-designed tissue bath system. The system is straightforward and comprises a strain gauge mated to a small bath chamber into which was placed the Hank's solution. For strain measurements, optical markers were placed onto the ligament tissue near the insertion sites. A small preload of 0.1N was applied to the ligaments in order to obtain a uniform starting point. The ligaments were then preconditioned to 1% strain for 10 cycles. After preconditioning, ligaments were pulled to failure at a rate of ~10% strain per second.

Tissue displacement was obtained using video dimensional analysis. The initial ligament length (Lo) was taken to be the length at preload. The change in distance between optical markers was calculated by analyzing the change in coordinate center of each marker from stored digital frames using a custom macro for Image-brand software. Image-brand software is a public domain image processing and analysis program for the Macintosh. It was developed at the Research Services Branch of the of the National Institute of Mental Health (NIMH), Bethesda, Md., part of the U.S. National Institutes of Health. A free PC version of Image, called Scion Image for Windows, is available from Scion Corporation (Frederick, Md.). Engineering strain was measured from displacement data as the change in length between stretched length and initial length (Lo), divided by the initial length:

$$\varepsilon = \frac{L - L_0}{L_0} \quad (1)$$

Force was measured and displayed on the video screen in synchrony with the displacement. Engineering stress was calculated as the force divided by the initial area:

$$\sigma = \frac{F}{A_0} \quad (2)$$

Stress-strain curves were created and fit with the microstructural model presented by Hurschler and co-workers (Hurschler, C., B. Loitz-Ramage, and R. Vanderby, Jr., "A structurally based stress-stretch relationship for tendon and ligament." *Journal of Biomechanical Engineering*, 1997. 119 (4): p. 392-9. Elastic moduli were obtained from this model.

The mechanical properties that were examined in this study were maximum force, ultimate stress, strain at failure, elastic modulus, and area. Statistical analysis was performed using an unpaired t-test (alpha=0.05) to compare differences between the control and treatment groups.

Comparison of Wet and Dry Weights: Ligament hydration was evaluated by comparing hydrated and dehydrated weights. For conformity, ligaments were hydrated for two hours in PBS, excess PBS was removed, and the tissues were then weighed immediately. Ligaments were weighed on a digital balance (Mettler-Toledo; Columbus, Ohio) to an accuracy of 0.00001 g. Each tissue was then dehydrated on glass coverslips at 60° C. for 24 hours and weighed a second time. The difference between wet and dry weights, normalized to the dry weight, was compared and group means were evaluated statistically using an unpaired t-test (alpha=0.05).

Evaluation of MCL Vascularity: To investigate tissue vascularity, the femoral arteries of six rats (3 treated, 3 controls) were cannulated. The proximal artery was tied off using a 4.0 nylon suture. Into the artery, 4 µm red fluorescent microspheres ($2 \times 10^7$ spheres suspended in 5% albumin solution) were injected as a 3 ml bolus. Five minutes following injection, the rats were sacrificed. Ligaments were harvested and fixed overnight in 4% formalin. Tissue was imaged with confocal microscopy to detect the presence of fluorescent microspheres. Ligaments were viewed in sagittal planes of focus, and scans were made through the ligament thickness. Stacking the sequentially scanned images created three-dimensional reconstructions. Images were then viewed with a computer and saved digitally.

Tissue Histomorphology and Protease Production: Immediately following death, eight MCLs (from 8 treated, 8 control rats) were exposed and dissected in toto from the tibial and femoral insertions. Ligaments were immediately fixed in Zamboni's fixative for three days at 4° C., and then stored overnight in a solution of 30% sucrose and fixative. Specimens were flash frozen, sectioned (6 µm), and mounted on slides. Immunohistochemical labels were applied using a diaminobenaldehyde (DAB) immunohistology kit for rodent tissue (Innogenex; San Ramon, Calif.). Slides were labeled for MMP-13 (collagenase 3), MMP-1, and cathepsin K following the manufactures instructions. Histological evaluation of tartrateresistant acid phosphatase (TRAP) was performed following previously published methods. Briefly, slides were incubated for two hours in equal parts of two buffer solutions: naphthol AS-BI phosphate buffer and hexazonium pararosaniline. Slides were evaluated using light microscopy.

Protease mRNA expression: Primer sets for cathepsin K, rat collagenase (MMP-13), TRAP, and glyceraldehyde-3-phosphate-dehydrogenase (GAPDH) have been developed and tested for specificity in our laboratory. The primer sets were either derived from previously published reports (rat collagenase Knittel, T., et al., "Expression patterns of matrix metalloproteinases and their inhibitors in parenchymal and non-parenchymal cells of rat liver: regulation by TNF-alpha and TGF-beta1." *Journal of Hepatology*, 1999. 30 (1): p. 48-60; Wells, G. M., et al., "Quantitation of matrixmetalloproteinases in cultured rat astrocytes using the polymerase chain reaction with a multi-competitor cDNA standard." *GLIA*, 1996. 18(4): p. 332-40 or designed from sequences available from GenBank (GAPDH, cathepsin K, and TRAP: Genbank Accession numbers are AF106860, AF010306, and M761 10, respectively) using the PrimerSelect module of the Lasergene 5.01 software (DNAStar, Madison, Wis.). Primer sequences are MMP-13: forward: 5'-AAA GAA CAT GGT GAC TTC TAC C-3' (SEQ. ID. NO: 1), reverse: 5'-ACT GGA TTC CTT GAA CGT C-3' (SEQ. ID. NO: 2), length 283 bp; Cathepsin K: forward: 5'-TGC GAC CGT GAT AAT GTG AAC C-3' (SEQ. ID. NO: 3), reverse: 5'-ATG GGC TGG CTG GCT TGA ATC-3' (SEQ. ID. NO: 4), length 205 bp; TRAP: forward: 5'-CGC CAG AAC CGT GCA GAT TAT G-3' (SEQ. ID. NO: 5), reverse: 5'-AAG ATG GCC ACG GTG ATG TTC G-3' (SEQ. ID. NO: 6), length 297 bp; GAPDH: forward: 5'-GAC TGT GGA TGG CCC CTC TG-3' (SEQ. ID. NO: 7), reverse: 5'-CGC CTG CTT CAC CAC CTT CT-3' (SEQ. ID. NO: 8); length 239 bp.

For total RNA isolation, the tissues (n=4 control, n=4 treated) were rinsed, after sterile harvesting, in DNase-, RNase-, and Protease-Free phosphate buffered saline to remove blood or other contaminants from the tissue, and placed in RNAlater solution (Ambion, Austin, Tex.). Tissues were pooled to ensure adequate measurable RNA yield. RNA isolation was performed using methods similar to that utilized by Reno and co-workers, which combines the TRIzol™ method with the column fractionalization steps of the RNeasy™ Total RNA kit (Qiagen Inc., Valencia, Calif.). Methods primarily followed the manufacturer's instructions for the respective steps. For tissue homogenization, MCLs were frozen with liquid nitrogen, placed in a liquid nitrogen cooled Braun Mikro-Dismembrator Vessel (B. Braun Biotech International, Allentown, Pa.) and reduced to powder. Following total RNA isolation, yield and purity of RNA were quantified by spectrophotometric measurement at 260, 280, and 325 nm (UltraSpec 3000 Spectrophotometer, Pharmacia Biotech, Cambridge UK). RNA was reverse transcribed into cDNA (20 μl total volume) by combining a mixture of 5 μl total RNA, 1 μl oligo(dT)$_{15}$ (250 ng/μl), and 5 μl RNase free water, with 9 μl of First Strand Synthesis buffer (Life Technologies) containing 40 units of RNase inhibitor (Ambion), 500 μM dNTP mix, 10 mM DTT, and 200 units of Superscript II reverse transcriptase.

Quantitative-PCR standards for the genes indicated above were prepared from purified PCR products of the target sequences. From spectrophotometric quantitation of the PCR products, the number of copies per μl of each standard was calculated, and ten-fold serial dilutions (ranging from $1\times10^9$ to 10 copies/μl) were prepared. The house-keeping gene GAPDH was used as internal control. Real-time QPCR was performed using a BIO-RAD iCycler iQ Real-time PCR system (BIO-RAD, Hercules, Calif.). All reactions were carried out in a total volume of 20 μl containing 1× Platinum Quantitative PCR Supermix (Life Technologies), 10 nM Fluorescein, 200 nM forward primer, 200 nM reverse primer, 0.25× Sybr Green, 5 μl template, and 3.95 μl DEPC-treated H$_2$O. PCR cycling consisted of initial denaturation at 95° C. for 3 minutes and up to 50 cycles of 95° C. denaturation for 15 sec.; 55 or 60° C. annealing (depending on template) for 30 sec.; 72° C. extension for 30 sec. During each cycle optical data were collected during the annealing and extension steps. Each gene was run in triplicate. The copy numbers of the respective cDNAs in the samples were determined relative to the standard curves. The cDNA copy number numbers of the target gene was normalized to the copy number of GAPDH.

Results:

Surgical Outcomes: All guanethidine treated rats developed ptosis (an indication of sympathetic inhibition) by the second day of treatment, and ptosis persisted throughout the ten-day period. No other gross changes were observed in vivo. No abnormalities in movement, body weight, or behavior were observed in either the treated or control groups. Upon tissue harvest, no morphological differences were macroscopically observed between control and treated MCL tissue.

Figure 11:
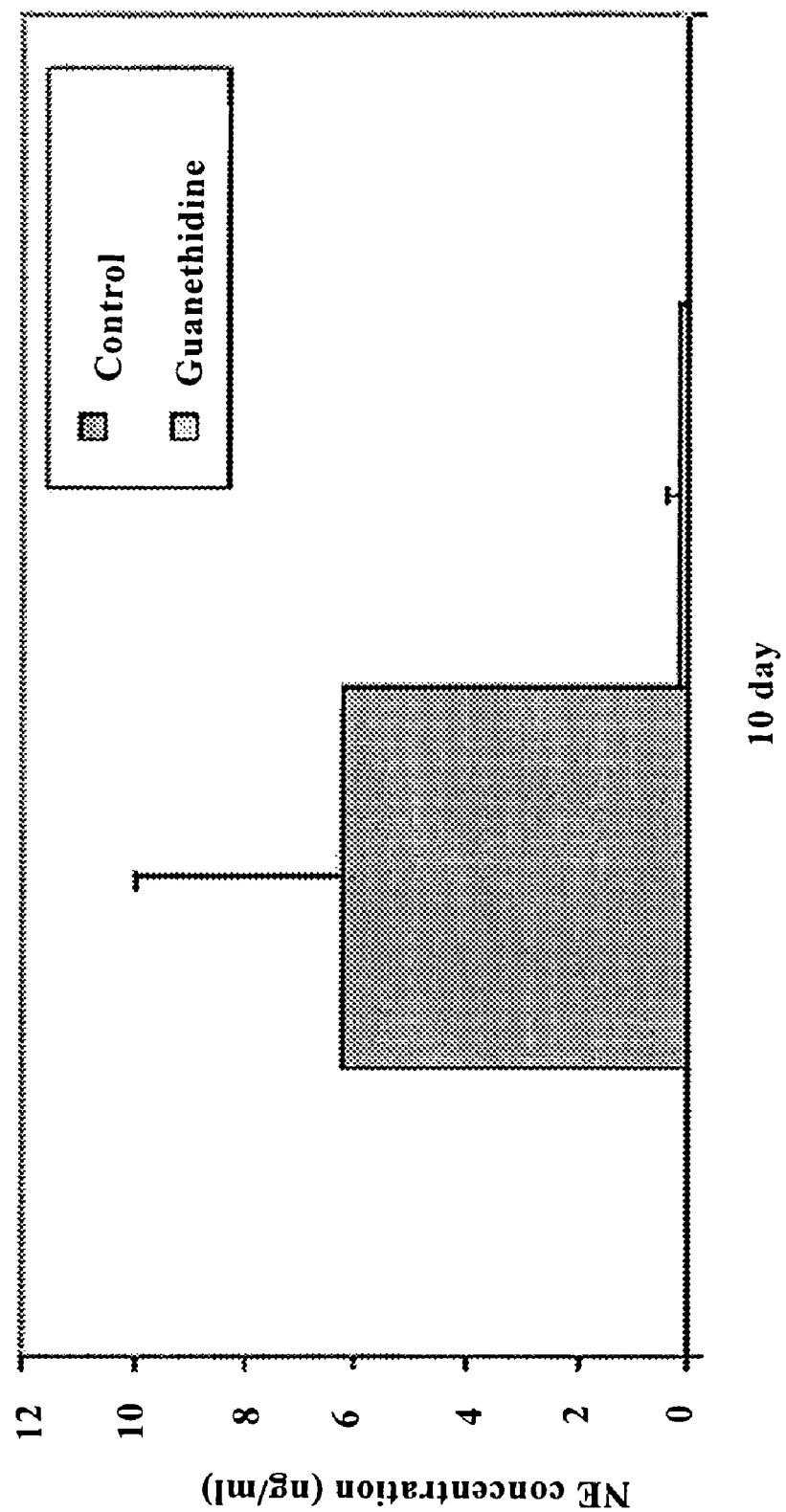
FIG. 11 is a graph depicting plasma concentrations of norepinephrine in a treated group versus control animals. Plasma concentrations of norepinephrine in the treated group were significantly lower than those in the control animals. See Example 4.
Figure 12:
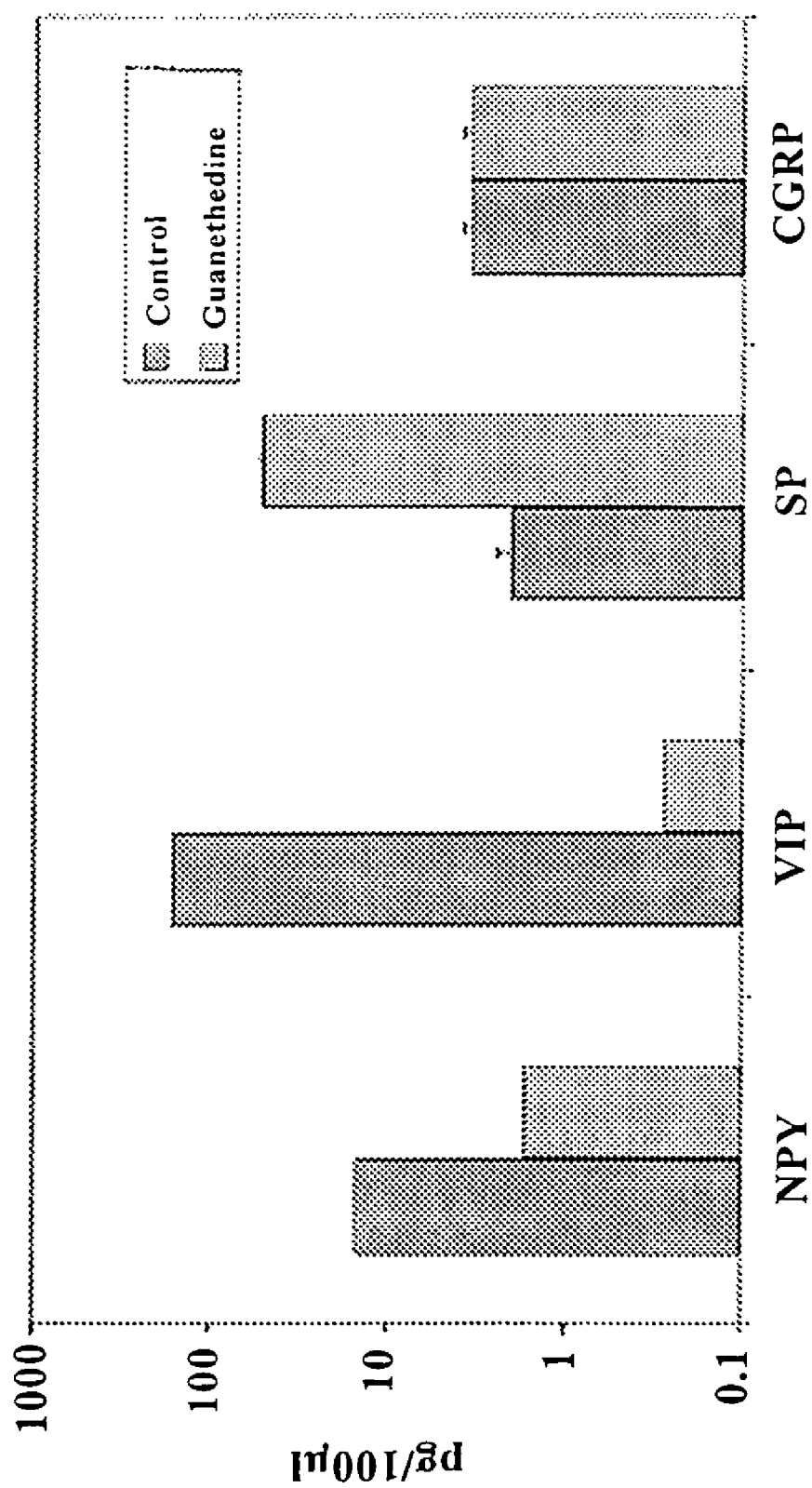
FIG. 12 is a graph depicting neuropeptide concentration in rat MCLs in control and guanethidine-treated rats after 10 days of treatment.

Neurotransmitter and Neuropeptide Concentrations: Plasma concentrations of norepinephrine in the treated group were significantly lower than those in control animals (0.1717±0.2 ng/ml vs. 6.272±3.7 ng/ml; p=0.04; FIG. 11), indicating significant inhibition of the sympathetic nervous system. Immunofluorescent labeling of neuropeptides revealed a disappearance of VIP from ligament tissue after guanethidine treatment, while NPY, SP, and CGRP remained unchanged, indicating an impairment to sympathetic and parasympathetic neuropeptides but not NPs from sensory nerves. RIA data confirmed the absence of VIP from guanethidine treated MCLs when compared to controls (0.042±0.005 pmol/g vs. 24.66±0.0015 pmol/g; p<0.001; see FIG. 12) and showed greatly decreased concentrations of NPY in treated MCLs (0.198±0.014 pmol/g vs. 1.76±0.001 pmol/g; p<0.001; FIG. 12). SP concentrations were also increased in guanethidine treated MCls (18.56±9.18 pmol/g vs. 0.729±0.148 pmol/g; p=0.03; FIG. 12). CGRP concentration remained unchanged (0.44±0.21 pmol/g vs. 0.20±0.045 pmol/g μl; FIG. 12).

Figure 13A:
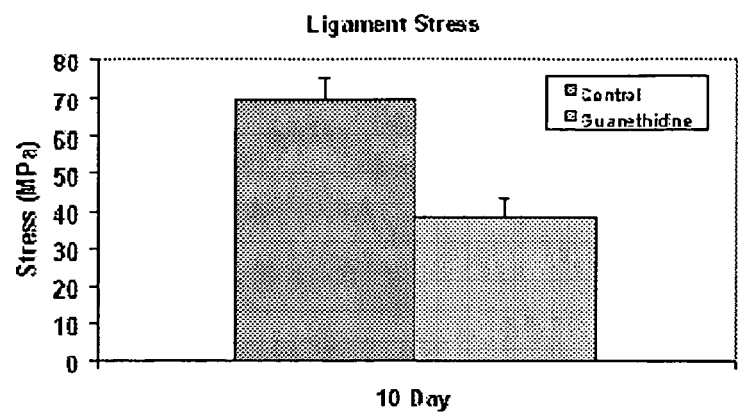
FIGS. 13A, 13B, and 13C are graphs depicting the mechanical properties of rat MCLs following 10 days of treatment with guanethidine versus controls.
Figure 13B:
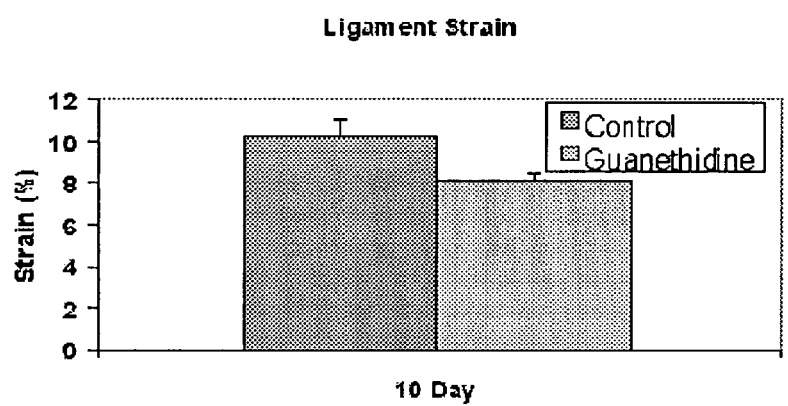
Figure 13C:
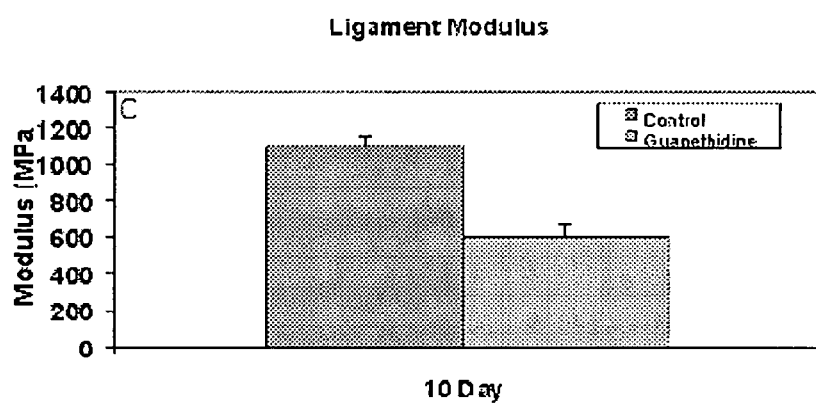

MCL Mechanics and Tissue Hydration: Results from organ culture experiments performed in order to examine the direct effect of guanethidine on ECM structural integrity revealed no changes in ultimate stress, area, or force. Ultimate stress values were nearly identical between contralateral ligaments (71.01±19.20 MPa (control) vs. 70.29±19.15 MPa (guanethidine); p=0.96). The ultimate stress in guanethidine treated animals was significantly decreased (70±5.2 MPa vs. 38±4.9 MPa; p=0.0006), as was the strain at failure (10.2±0.69% vs. 8.1±0.4%; p=0.031), and the elastic modulus (1090±60 MPa vs. 598±77 MPa; p=0.0003) when compared to MCLs from saline receiving control animals. See FIGS. 13A, 13B, and 13C, respectively. A significant increase in MCL area was also present in treated tissues (0.41±0.03 mm$^2$ vs. 0.32±0.03 mm2; p=0.04). The mean ultimate tensile force was not significantly decreased in treated tissues (p=0.76). The increase in area is due (at least in part) to an increase in fluid content in the ligament, as supported by a statistically significant increase in the wet weight (5.1±0.7 g vs. 6.8±0.7 g; p=0.042).

MCL Vascularity: Analysis of tissue vascularity using fluorescent microspheres, qualitatively revealed guanethidine treatment increased vascularity compared to control animals. Substantial and consistent differences in microsphere deposition were easily detectable between treated and control animals.

Proteolytic Enzymes: The MCLs from the guanethidine treated animals labeled positively for cathepsin K, and TRAP. Cathepsin K labels were observed near the peripheral portions of the ECM and within the ligament matrix. TRAP staining was seen throughout the ligament with heaviest staining seen in the ligament matrix. No ligaments (except the positive control slides) had positive staining for MMP-1 or MMP-13 (results not shown). Real-time QPCR produced consistent results and showed increases in cathepsin K, MMP-13, and TRAP. Increases in the expression of cathepsin K (58.04±8.08 vs. 31.97±9.40 copies/1000 copies GAPDH), and MMP-13 (6.91±2.98 vs. 0.271±0.04 copies/1000 copies GAPDH), and were seen in the treated tissues as compared to control tissues. In the both untreated and treated tissues the overall expression of TRAP was very small.

Analysis of blood flow using fluorescent microspheres revealed that guanethidine treatment increased blood flow as compared to blood flow in control animals. In addition, chemical sympathectomy with guanethidine resulted in altered mechanical properties of the ligament tissues. Ultimate stress in guanethidine-treated animals was significantly decreased (FIG. 8; p=0.0006), as was the strain at failure (FIG. 9; p=0.031), and elastic modulus (p=0.0003) as compared to MCLs from saline-treated control animals.

A significant increase in MCL area was also present in treated tissues. This increase is due (at least in part) to an increase in fluid content in the ligament, as supported by a statistically significant increase in the wet weight (p=0.042) of the treated ligaments. Immunohistochemical analysis of guanethidine-treated animals revealed that the MCLs labeled positively for cathepsin K and TRAP. Real-time QPCR showed consistent increases in cathepsin K, MMP-13, and TRAP in the treated ligaments.

Thus, after only ten days of treatment with guanethidine, normal rat MCLs were significantly degraded in mechanical and morphologic properties. These changes in mechanical properties are likely to be the result of altered neuropeptide levels, which lead to changes in blood flow, and the expression of proteolytic enzymes. In addition, this decrease in normal tissue properties provides compelling evidence to expect a substantial improvement in ligament healing upon treatment with neurogenic compounds (see, e.g., Example 3).

PNS Inhibition Degrades Intact Ligament: Results of this study support the hypothesis that inhibition of the sympathetic nervous degrades ligament. Data reveal that guanethidine does not directly affect structural integrity (via tissue culture experiments), but that chemically induced sympathectomy does. Reduced plasma concentrations of norepinephrine as well as ptosis in the treated group indicate that guanethidine was effective in blocking the sympathetic nervous system. Though histologic ligament sections only showed changes in VIP immunoreactivity, RIA data from the guanethidine treated rats showed decreases in both NPY and VIP, indicating that levels of autonomic neuropeptides were altered. Substance P concentrations were also increased in guanethidine treated MCLs indicating that blockade of efferent nerve fibers may alter concentrations of afferent neuropeptides as well. In vivo administration of guanethidine decreased ultimate stress, decreased elastic modulus, decreased strain at failure, and increased cross sectional area. The mean ultimate force decreased after ten days of in vivo guanethidine treatment, but the change was not statistically significant. The increased area is likely the result of increased tissue hydration, as exhibited by a significant increase in the MCL wet weight. Increased hydration may be due to changes in vessel permeability (as mediated by neuropeptides). Alternatively, changes in ECM components such as proteoglycans, which are known to affect tissue water content as well as stabilize collagen ECM organization, could account for the increased hydration. Strain at failure was significantly altered, implying some alterations to ECM organization and integrity.

PNS Influences MCL Physiology: Tissue vascularity was significantly higher in MCLs from guanethidine treated animals, which is consistent with previous reports. The increased vascularity was most likely the result of altered concentrations of neurotransmitters and neuropeptides. Our results in rats agree with rabbit experiments in which the authors report that altering levels of neuropeptides and norepinephrine alters MCL blood flow (Ferrell, W. R., J. J. McDougall, and R. C. Bray, "Spatial heterogeneity of the effects of calcitonin gene-related peptide (CGRP) on the microvasculature of ligaments in the rabbit knee joint." *British Journal of Pharmacology,* 1997. 121(7): p. 1397-405.). Others report that partial tears to both the MCL and ACL increase ligament blood volume, which also may be mediated by the peripheral nervous system Bray, R. C., C. A. Leonard, and P. T. Salo, "Vascular physiology and longterm healing of partial ligament tears." *J Orthop Res,* 2002. 20: p. 984-989; McDougall, J. J., W. R. Ferrell, and R. C. Bray, "Spatial variation in sympathetic influences on the vasculature of the synovium and medial collateral ligament of the rabbit knee joint." *Journal of Physiology,* 1997. 503(Pt 2): p. 435-43; McDougall, J. J., et al., "A role for calcitonin gene-related peptide in rabbit knee joint ligament healing." *Canadian Journal of Physiology & Pharmacology,* 2000. 78(7): p. 535-40.

Guanethidine treated rats increased their expression proteolytic enzymes (MMP-13 and cathepsin K) within MCL tissue. Expression of TRAP was low in control and treated MCLs. Histology confirmed the presence of cathepsin K, and showed the presence of TRAP in guanethidine treated MCLs. The presence of these enzymes may have altered the MCL mechanical properties in the treated animals. Remodeling and degradation of connective tissues depend greatly on the action of proteolytic enzymes including MMPs and cysteine proteinases (such as cathepsins). Matrix metalloproteinases have been implicated in remodeling the ECM of a number of orthopedic tissues including ligament, cartilage, and bone. Matrix metalloproteinase-13 has enzymatic specificity for type I collagen and therefore may contribute to matrix degradation Hart, D. A., et al., "Pregnancy induces complex changes in the the pattern of mRNA expression in knee ligaments of the adolescent rabbit." *Matrix Biology,* 1998. 17(1): p. 21-34; Hellio Le Graverand, M. P., et al., "Matrix metalloproteinase-13 expression in rabbit knee joint connective tissues: influence of maturation and response to injury." *Matrix Biol,* 2000. 19(5): p. 431-41; Nagase, H. and J. F. Woessner, Jr., "Matrix metalloproteinases." *J Biol Chem,* 1999. 274(31): p. 21491-4; Uusitalo, H., et al., "Expression of cathepsins B, H, K, L, and S and matrix metalloproteinases 9 and 13 during chondrocyte hypertrophy and endochondral ossification in mouse fracture callus." *Calcif Tissue Int,* 2000. 67(5): p. 382-90.

Cysteine proteases also degrade collagen as well as other ECM components. Cathepsin K plays a substantial role in bone remodeling and also has specificity for type I collagen (Yamashita, D. S. and R. A. Dodds, "Cathepsin K and the design of inhibitors of cathepsin K." *Curr Pharm Des,* 2000. 6(1): p. 1-24; Tsuji, Y., et al., "Expression of cathepsin K mRNA and protein in odontoclasts after experimental tooth movement in the mouse maxilla by in situ hybridization and immunoelectron microscopy." *Cell Tissue Res,* 2001. 303(3): p. 359-69; Saftig, P., et al., "Functions of cathepsin K in bone resorption. Lessons from cathepsin K deficient mice." *Adv Exp Med Biol,* 2000. 477: p. 293-303; Kafienah, W., et al., "Human cathepsin K cleaves native type I and II collagens at the N-terminal end of the triple helix." *Biochem J,* 1998. 331 (Pt 3): p. 727-32. Garnero, P., et al., "The collagenolytic activity of cathepsin K is unique among mammalian proteinases." *J Biol Chem,* 1998. 273(48): p. 32347-52; Domon, S., et al., "In situ hybridization for matrix metalloproteinase-1 and cathepsin K in rat root-resorbing tissue induced by tooth movement." *Arch Oral Biol,* 1999. 44(11): p. 907-15; Bossard, M. J., et al., "Proteolytic activity of human osteoclast cathepsin K. Expression, purification, activation, and substrate identification." *J Biol Chem,* 1996. 271(21): p. 12517-24.

Cathepsin K has been found in synovial fibroblasts and multinucleated giant cells, suggesting a role for the enzyme in rheumatoid arthritis and in response to calcified tendonitis in human rotator cuff tendon (Hao, Z., V. L. Kalscheur, and P. Muir, "Decalcification of bone for histology and immunohistochemistry." *Journal of Histotechnology,* 2002: p. in press; Nakase, T., et al., "Involvement of multinucleated giant cells synthesizing cathepsin K in calcified tendinitis of the rotator cuff tendons." *Rheumatology* (Oxford), 2000. 39(10): p. 1074-7). Tartrate resistant acid phosphatase, which may play a collagenolytic role in calcified tissue, is also present in canine cruciate ligaments following a rupture (Muir, P., et al., "Evaluation of tartrate-resistant acid phosphatase and cathepsin K in ruptured canine cranial cruciate ligament." *Am J Vet Res,* 2002. 63: p. 1279-1284; Halleen, J. M., et al., "Intracellular fragmentation of bone resorption products by reactive oxygen species generated by osteoclastic tartrateresistant acid phosphatase." *J Biol Chem,* 1999. 274(33): p. 22907-10).

Tartrate resistant acid phosphatase is capable of generating reactive oxygen species that can target and cleave type I collagen (Haleen, supra). Hence, the presence of TRAP and cathepsin K in guanethidine treated ligaments suggests that the collagenolytic activity of these enzymes contributes to the observed changes in mechanical behavior and morphology. The association herein between collagenolytic enzymes and the PNS suggests that neurogenic factors are important in chronic ligament and tendon problems such as disuse or overuse.

This example suggests a significant regulatory role for the sympathetic nervous system in the homeostasis of ligaments. Although guanethidine is used clinically to treat pain associated with orthopedic diseases, the effects of this drug on connective tissues have not been previously shown. This study suggests that the administration of guanethidine can be detrimental to the ligament structure. Additionally, this study strongly suggests that sympathetic peripheral nerves influence ligament homeostasis by altering MCL vascularity and levels of neuropeptides, while mediating levels of degradative enzymes. Changes of the ECM mediated by neurogenic factors have clinical relevance. Ligament and tendon grafting is common. Grafting studies primarily focus on the repair of damaged matrix but do not consider regeneration of peripheral nerves to help regulate tissue healing and remodeling. The PNS appears to have an important regulatory role in normal ligaments. Decreases in autonomic neuropeptides lead to mechanical deficits in intact MCLs, suggesting a role for peripheral neuropeptides in maintaining the functional properties of ligaments and provides novel ways to improve clinical outcomes with tissue grafts or with tissue engineered materials.

Example 5

Effects of Capsaicin on Tissue Healing

To study the effect of capsaicin on normal rat MCLs, eighteen Wistar rats (250 g to 320 g) were divided into two groups. In Group 1 (n=6), capsaicin was injected (50 mg/kg). In Group 2, control rats (n=6) were injected with an equal volume of 0.9% saline. Six additional rats were used to study the effects of capsaicin on healing MCLs. These rats were also divided into two groups. Group 3 (n=3) rats were given the same concentration of capsaicin as Group 1 rats, while Group 4 (n=3) rats were used as saline controls. After 3 days of treatment, both groups underwent a surgical rupture of one MCL. Contralateral MCLs were used as sham controls. All rats were maintained in their normal cage environment for 10 days. Then, they were sacrificed as noted above. Femur-MCL-tibia (FMT) complexes were then harvested and tested as above.

Upon harvest no morphologic differences could be seen macroscopically between control and treated rat ligaments for Groups 1 and 2. However, Group 3 (capsaicin-treated) tissue had a more gelatinous appearance as compared to Group 4 tissue. RIA data and immunofluorescence confirmed that SP and CGRP concentrations within the MCL were reduced within capsaicin treated group (see FIG. 10). As before, organ culture experiments with capsaicin-supplemented media revealed no changes in ultimate force, indicating no direct drug effect of capsaicin on ECM integrity.

Figure 8:
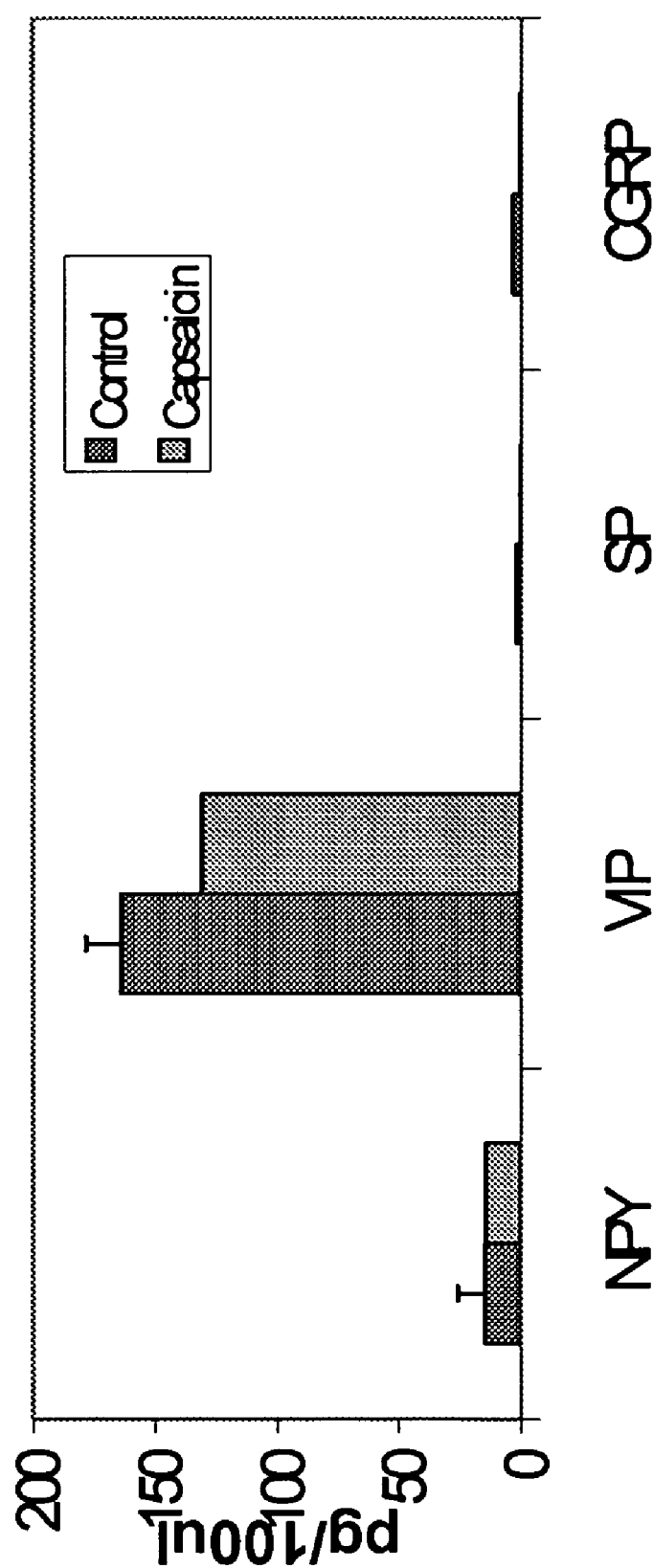
FIG. 8 is a graph depicting the concentration of NPY, VIP, SP, and CGRP in rat MCLs treated with capsaicin as compared to untreated controls (see Example 4).
Figure 9:
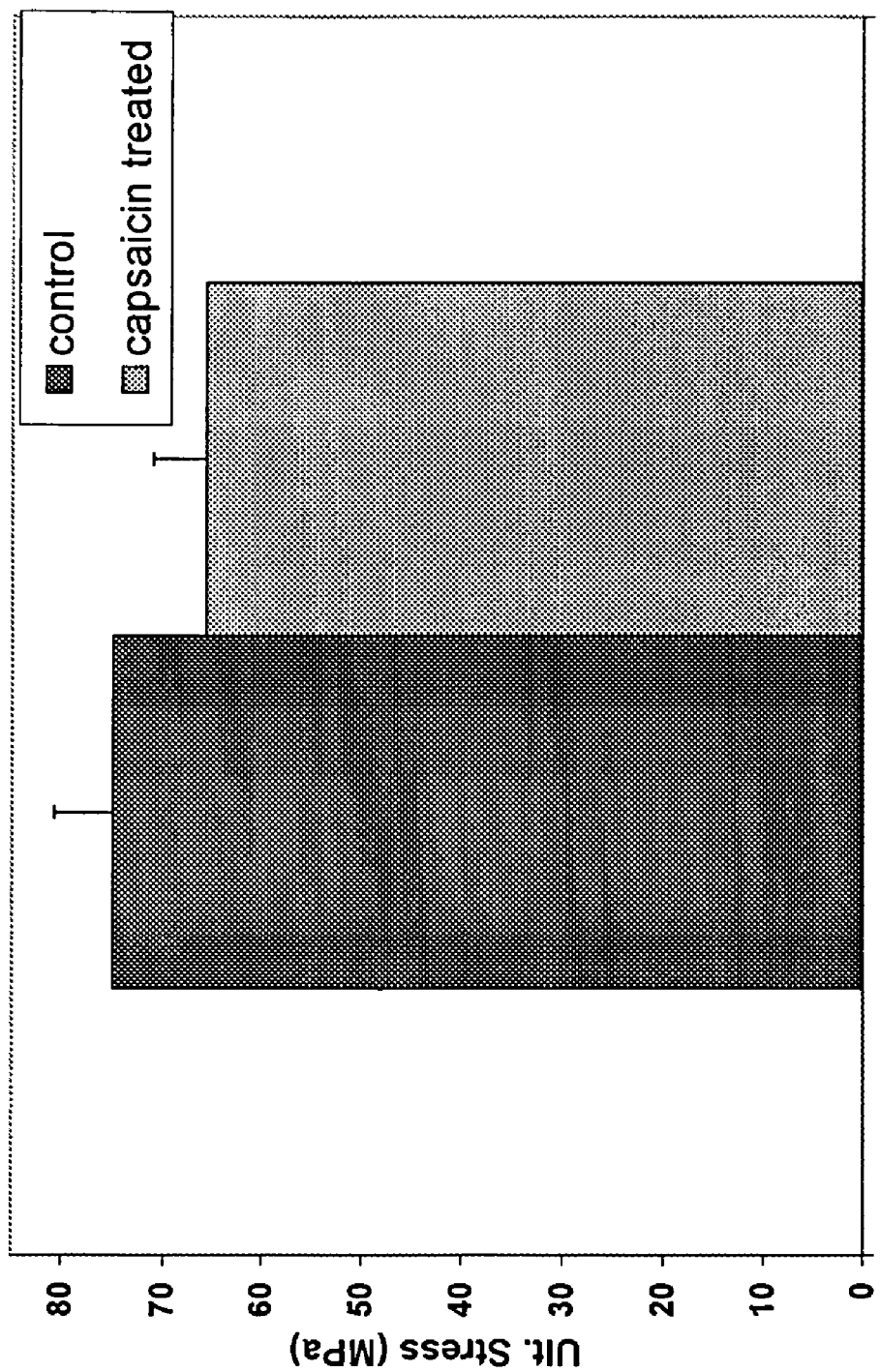
FIG. 9 is a graph depicting the ultimate stress exhibited by intact rat MCLs treated with capsaicin as compared to untreated controls (see Example 4).
Figure 10:
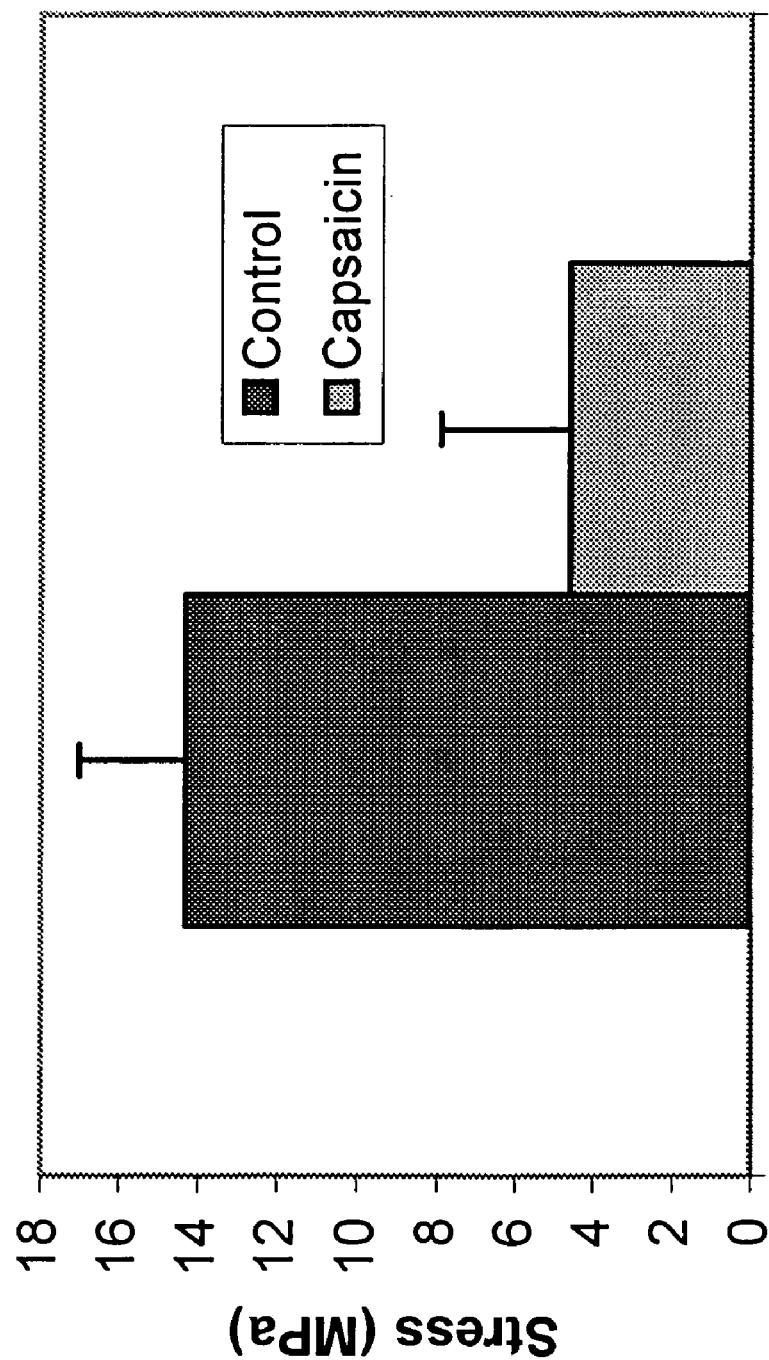
FIG. 10 is a graph depicting ultimate stress exhibited by healing rat MCLs (surgically ruptured) treated with capsaicin as compared to untreated controls (see Example 5).

After in vivo treatment, analysis of the mechanical properties revealed ultimate stress in capsaicin-treated but intact rat MCLs was substantially reduced (FIG. 8). Inhibition of the sensory nerves, also resulted in substantial changes to structural integrity of the healing ligament. In the capsaicin-treated animals, one MCL failed to heal. In the remaining capsaicin-treated animals, the ultimate stress of the ruptured ligament was significantly lower (4.6 MPa vs. 14.3 MPa; p=0.037; n=3; FIG. 10) as compared to controls. Hence, after only 10 days substantial changes in mechanical properties of capsaicin-treated intact MCLs were present. In addition, this decrease in normal tissue properties is even more significant in healing MCLs.

These data present compelling evidence that sensory neurogenic factors are essential to proper ligament healing.

In a further demonstration of the effect of capsaicin on ligament healing, thirty female Wistar rats (250 to 320 g) were divided into four groups: 1) capsaicin treatment without MCL rupture, 2) saline control without MCL rupture, 3) capsaicin treatment with MCL rupture, and 4) saline control with MCL rupture. For all groups, anesthesia (isofluorane 0.5-3%) was initiated in an induction chamber and maintained with a facemask. Into Groups 1 (n=6 animals) and Group 3 (n=9 animals), capsaicin (50 mg/kg/day; prepared by emulsification in 10% Tween 80 and 10% ethanol in sterile 0.9% saline) was injected subcutaneously on a daily basis for three consecutive days. Injections were made into a site between the scapulae. Since administration of capsaicin causes neuropeptide release and pain, the all injections were given under general anesthesia with maintenance of general anesthesia for thirty minutes after injection. Bupivicaine was also administered subcutaneously at the site of the capsaicin injection. Furthermore, to counteract any respiratory complications that could arise due to the administration of capsaicin, every animal also received an intraperitoneal injection of atropine (0.2 mg/kg), and terbutaline (0.2 mg/kg) fifteen minutes prior to capsaicin injection. Into Group 2 (n=6 animals) and Group 4 (n=9 animals), a similar volume of sterile saline was injected via the same method. All other medications were given as in the treated groups. There were no signs of infection, discomfort, or unusual behavior in the treated rats. On the third day of capsaicin or control treatment, rats in Groups 3 and 4 underwent complete rupture of one MCL. Contralateral legs were used as sham controls. Rats in Groups 1 and 2 were euthanized 10 days after the last injection of capsaicin or saline with intraperitoneal injections of pentobarbitone (150 mg/kg). Rats in Groups 3 and 4 were euthanized 14 days after the last injection of capsaicin or saline. Throughout the study only one ligament per animal was used for a particular experimental test protocol, with the exception of MCLs used for mechanical testing, which were also used for radioimmunoassay.

Neuropeptide Radioimmunoassay: Four MCLs from all groups were used for quantification of neuropeptide concentrations via RIA. MCLs were homogenized using a mortar and pestle. Homogenate was used to complete standard SP, CGRP, NPY, and VIP RIA protocols (Phoenix Pharmaceuticals, Belmont, Calif.). Briefly, samples were mixed with an antibody specific to one of the neuropeptides, and then incubated with a I-125 traced peptide. The radioactivity of each sample was measured using a gamma counter. Standards for each neuropeptide were included in the kit and MCL neuropeptide concentration was determined from a standards curve. Statistical analysis was performed using ANOVA (alpha=0.05) to compare differences between the treatment groups.

Immunofluorescent Evaluation of Neuropeptides: Immediately following death, two MCLs from Groups 1 and 2 were exposed and dissected in toto from the tibial and femoral insertions. Ligaments were immediately fixed in 4% formalin for 24 hours. Ligaments were washed in PBST (PBS plus 1.0% Tween 20) between incubations. Ligaments were either co-incubated in a primary antibody for NPY (1:10000 dilution) and VIP (1:1000 dilution), or SP (1:2000 dilution) and CGRP (1:2000 dilution; all antibodies Chemicon, Temecula, Calif.). Each ligament was then incubated in two host84 appropriately tagged (AMCA or Rhodamine; Chemicon, Temecula, Calif.) secondary antibodies. Confocal microscopy was used to examine the sections for fluorescent labeling. Ligaments were viewed in sagittal planes of focus, and scans were made through the ligament thickness. Three-dimensional reconstructions were made from individual confocal images by stacking the sequentially scanned images. Images were then viewed with a computer and saved digitally.

Organ Culture: In order to assess the effect of capsaicin directly on extracellular matrix integrity, organ culture of the MCL was employed. Bilateral MCLs (n=6 female Wistar rats; not included in the number of animals listed in the Animal Models and Surgery section) including intact femoral and tibial segments were aseptically harvested from untreated rats. The left MCL was used as a control tissue while the right MCL was cultured with capsaicin.

During and after harvest, tissues were rinsed in sterile phosphate buffered saline (PBS) containing penicillin (100 U/mL), streptomycin (100 μg/mL), and fungizone (0.25 μg/mL). Bone blocks were trimmed in order to minimize the amount of bone marrow, which may alter the culture environment. Tissues were then cultured in Dulbecco's Modified Eagle's Medium (DMEM) supplemented with 10% fetal bovine serum, nonessential amino acids (0.1 mM), L-glutamine (4 mM), penicillin (100 U/mL), streptomycin (100 μg/mL), and fungizone (0.25 μg/mL). Capsaicin or sterile PBS was added to media for the treated and control tissues, respectively. The concentration of capsaicin in media was selected to be the same as the concentration of capsaicin present in the blood during treatment (described above) using normative rat data for blood volume (5 mL blood/100 g body weight). The cultures were maintained in an incubator at 37° C. and 5% $CO_2$. Media were changed every 48 hours at which time tissues were rinsed with sterile PBS to reduce drug carryover into the fresh media containing the treatment drug or equivalent volume of carrier. Organ culture was maintained for 10 days after which time the MCLs were tested mechanically in the same manner as the in vivo treatment group.

Mechanical Testing: Mechanical testing was performed as described in the previous examples. Briefly, animal hind limbs from all groups (n=4 Group 1; n=4 Group 2; n=4 Group 3; n=4 Group 4) were disarticulated at the hip joint and stored at −80° C. until testing. On the day of testing, MCLs including intact femoral and tibial bone sections were excised for ex vivo testing. Ligament thickness and width was measured optically, and MCL area was estimated with elliptical geometry. For strain measurements, optical markers were placed onto the ligament tissue near the insertion sites. A small preload of 0.1N was applied to the ligaments in order to obtain a uniform starting point. The ligaments were then preconditioned to 1% strain for 10 cycles. After preconditioning, ligaments were pulled to failure at a rate of ~10% per second. Tissue displacement was obtained using video dimensional analysis using equations (1) and (2) infra. The mechanical properties that were examined in this study were maximum force, ultimate stress, strain at failure, elastic modulus, and area. Statistical analysis was performed using an unpaired t-test (p=0.05) to analyze differences between the control and treatment group.

Tissue Histomorphology and Protease Production: Immediately following death, six MCLs (3 from Group 2 animals, 3 from Group 4 animals) were exposed and dissected in toto from the tibial and femoral insertions. Ligaments were immediately fixed in formalin fixative for three days at room temperature. Specimens were embedded in paraffin, sectioned (6 μm), mounted on slides, and stained with hematoxylin and eosin (H&E).

Surgical Outcomes: No abnormalities in movement, body weight, or behavior were observed in either the treated or control groups following initial recovery from capsaicin injection. No morphological differences in Group 1 and 2 MCLs were observed at the time of tissue harvest. However in Group 3 and 4 animals, differences between skin wound healing and MCL healing were observed. Skin wounds and MCLs in Group 3 animals healed poorly, and large scars developed adjacent to all capsaicin treated MCLs within the quadriceps muscles. In one case, the MCL from a Group 3 rat also failed to heal (data from this animal are not included in the mechanical analysis).

Figure 15A:
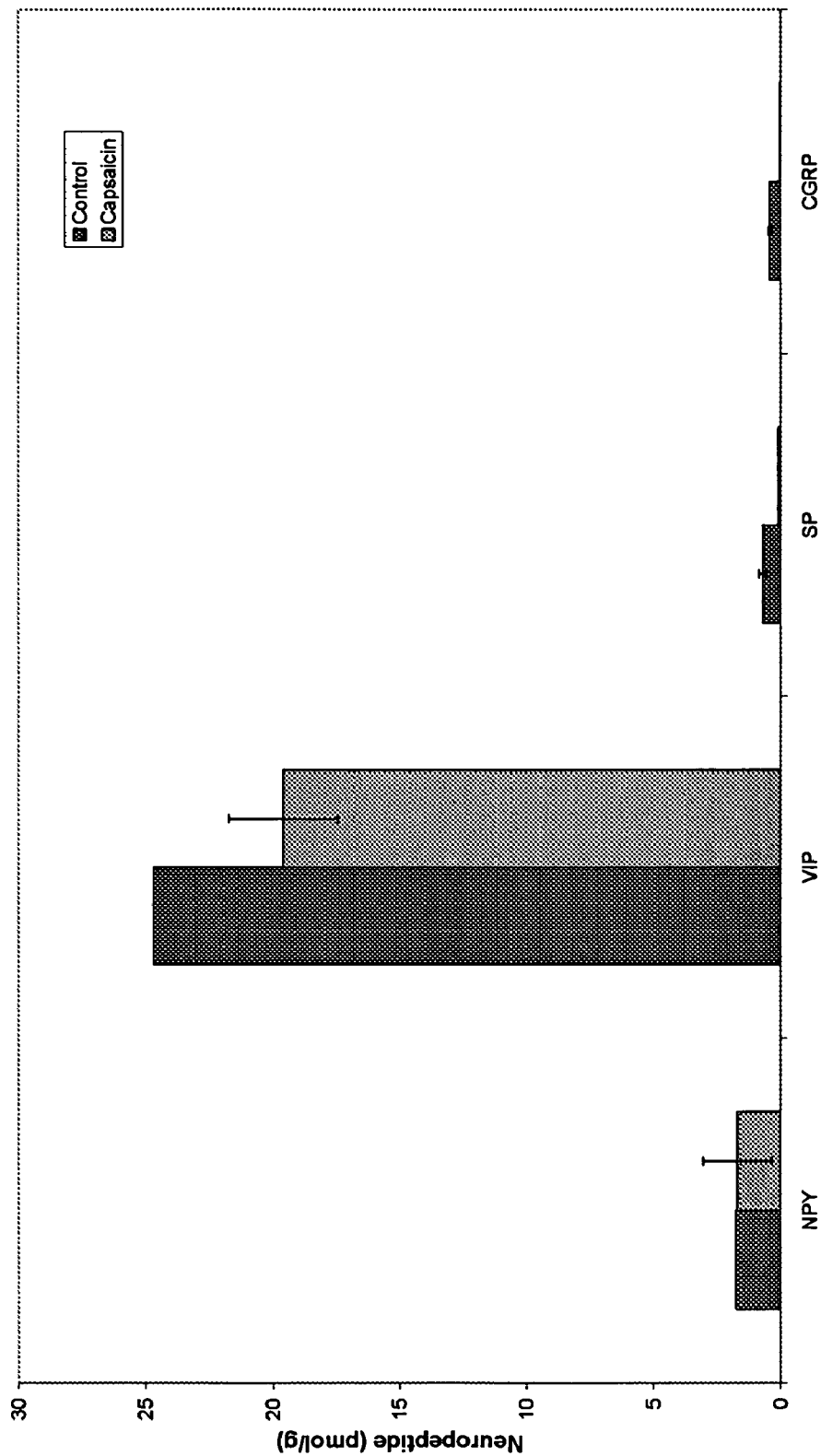
FIGS. 15A and 15B are graphs showing the concentration of SP and CGRP in MCL tissue extracts.
Figure 15B:
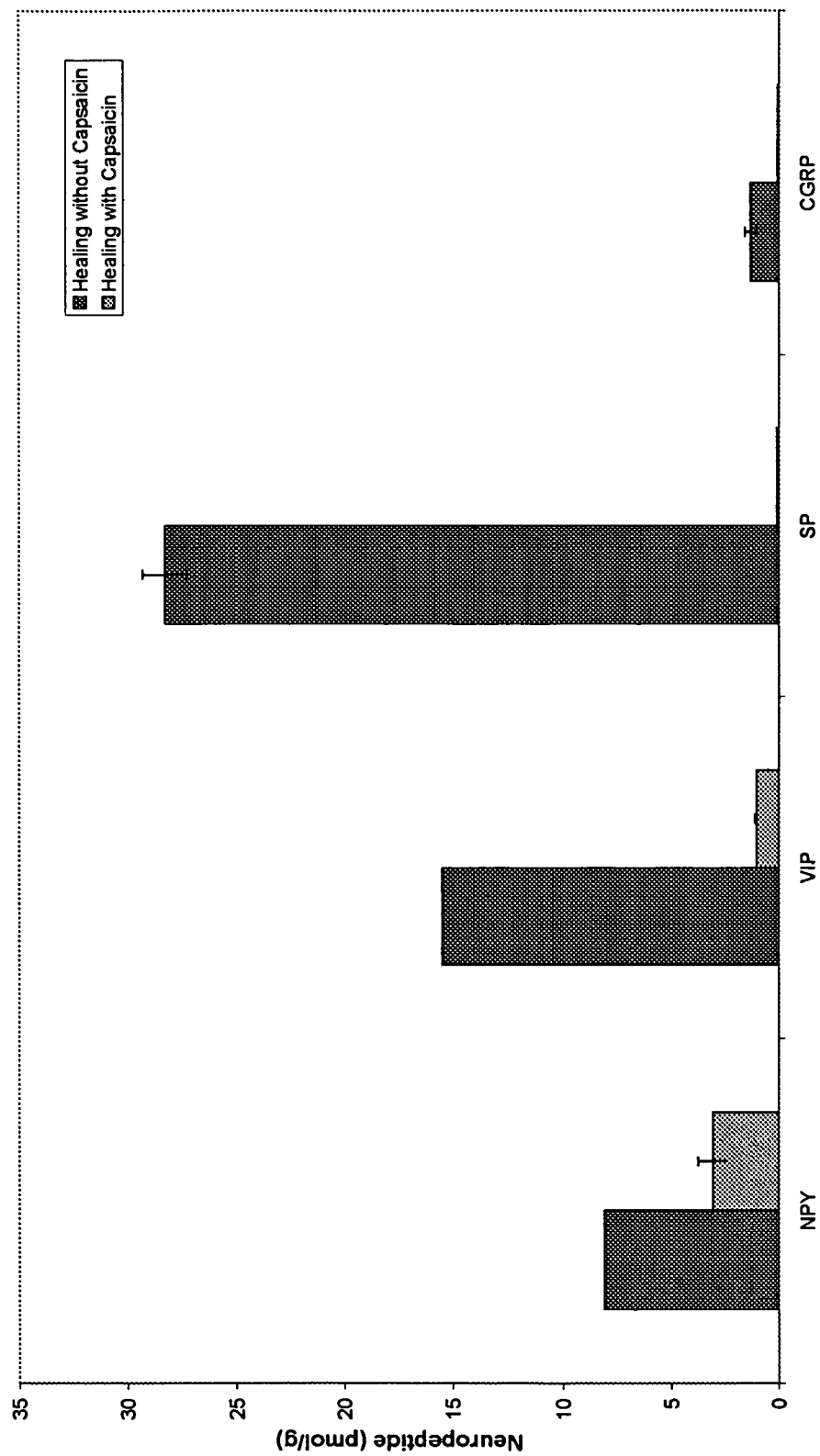

Neuropeptide Concentrations: Immunofluorescent labeling of neuropeptides revealed a disappearance of SP and CGRP from Group 1 and Group 3 ligaments after capsaicin treatment, indicating an impairment to afferent neuropeptides (see FIGS. 14A and 14B, respectively). RIA data confirmed a reduction of SP (0.10 pmol/g μl vs. 0.73 pmolg; p=0.05) and CGRP (0.04 pmol/g vs. 0.45 pmol/g; p=0.04) from Group 1 (intact, treated) MCLs when compared to Group 2 (intact, control) (FIG. 15A). No changes were seen in the concentrations of NPY or VIP in intact MCLs of capsaicin treated animals when compared to controls. Substance P and CGRP in capsaicin treated animals remained reduced during healing. Group 3 animals had significantly lower concentrations of SP (0.09 pmol/g vs. 28.27 pmol/g; p=0.01) and substantially lower CGRP concentrations (0.042 pmol/g vs. 1.01 pmol/g, p=0.09) compared to Group 4 MCLs (see FIG. 15A). In addition Group 3 MCLs had lower VIP (1.07 pmol/g vs. 15.5 pmol/g; p<0.01) and NPY (3.09 pmol/g vs. 8.09 pmol/g; p<0.01) concentrations when compared to Group 4 MCLs (see FIG. 15B).

MCL Mechanics: Results from organ culture experiments performed in order to examine the direct effect of capsaicin on ECM structural integrity revealed no changes in ultimate stress, area, or force. Ultimate stress values were not changed between contralateral ligaments (75.0±5.2 MPa (control) vs. 66.0±4.7 MPa (capsaicin); p=0.26).

Figure 16A:
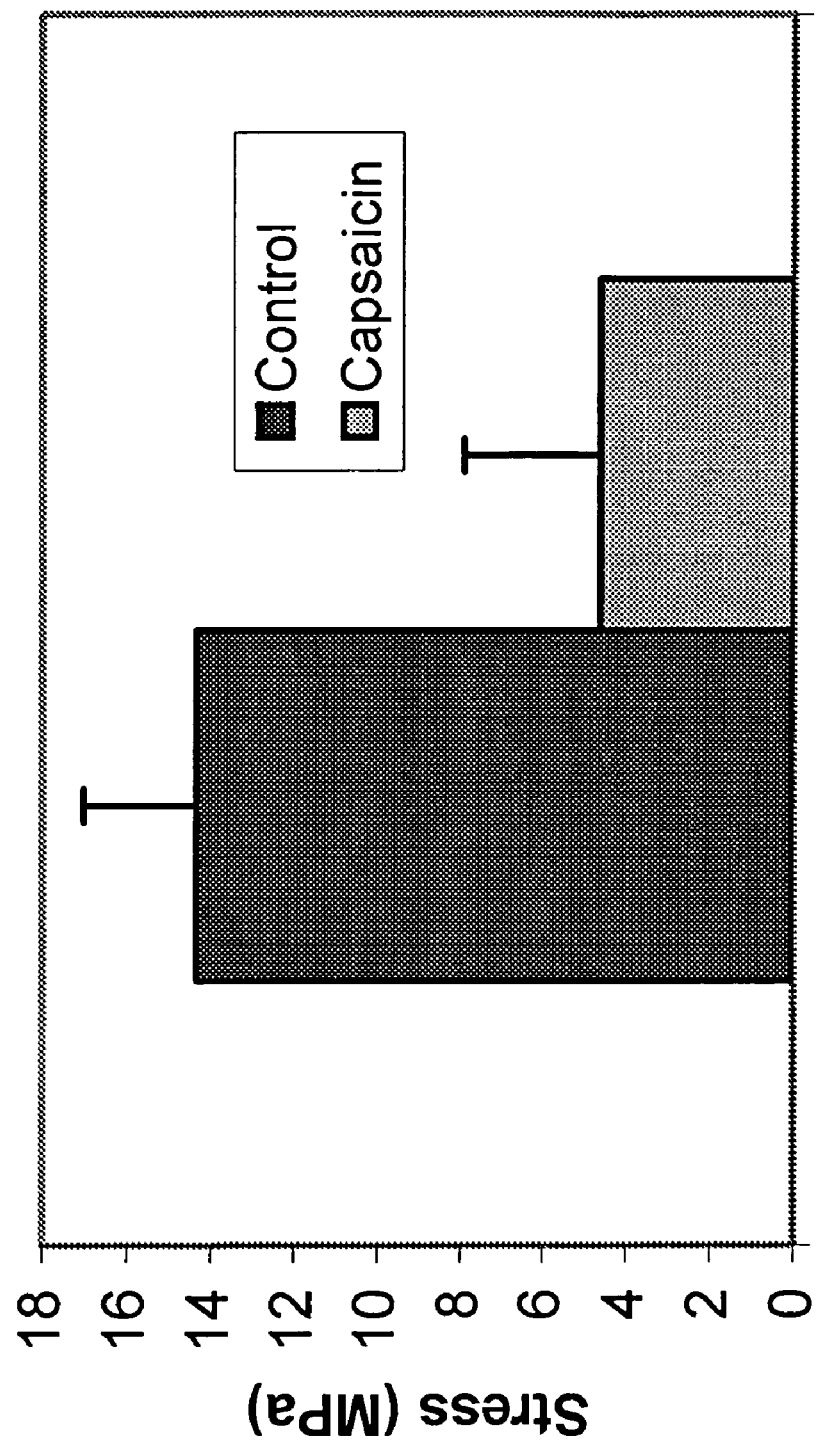
FIG. 16A is a graph showing reduced failure force of capsaicin-treated MCLs after two weeks of healing.
Figure 16B:
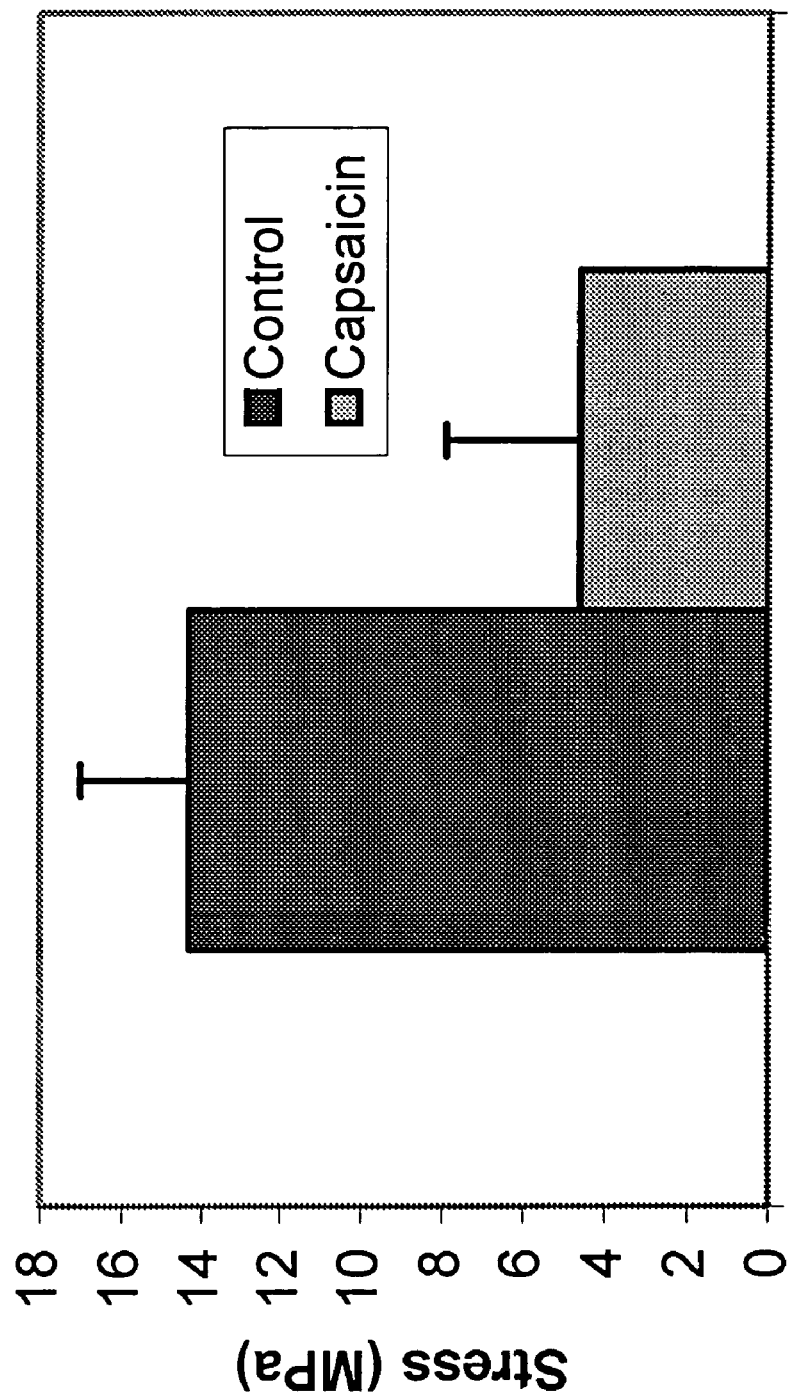
FIG. 16B is a graph showing reduced strength of capsaicin-treated MCLs after two weeks of healing.

Failure force, ultimate stress, failure strain, area, and elastic modulus in capsaicin treated animals were not significantly changed between Groups 1 and 2. These data suggest that capsaicin has little direct effect on intact ligamentous structures. In healing animals, the failure force was significantly reduced in capsaicin treated healing (4.5±2.7 N vs. 16.2±2.9 N; p=0.001; see FIG. 16A). The ultimate stress of Group 3 MCLs was also significantly lower when compared to Group 4 controls (2.7±1.9 MPa vs. 9.8±3.4 MPa; p=0.014; see FIG. 16B). No changes were seen in any other mechanical properties investigated. Hence, after only 10 days of healing, capsaicin had little effect on strength of intact MCLs, but had a significant impact on MCL healing strength.

Figure 17B:
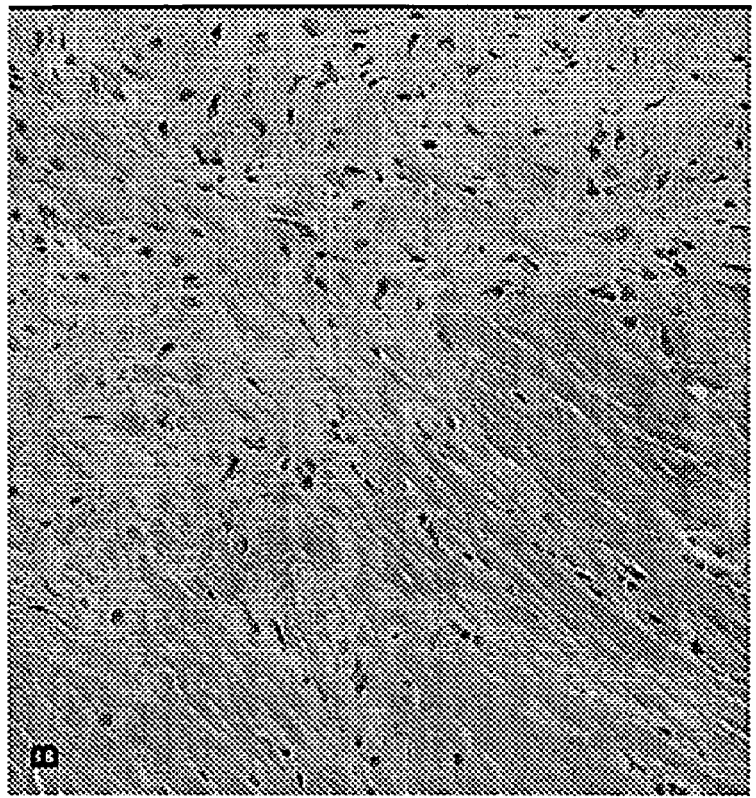
FIGS. 17A and 17B are photomicrographs of collagen matrix from control animals (FIG. 17A) and from animals treated with capsaicin (FIG. 17A). Both photos were taken after two weeks of healing.
Figure 17A:
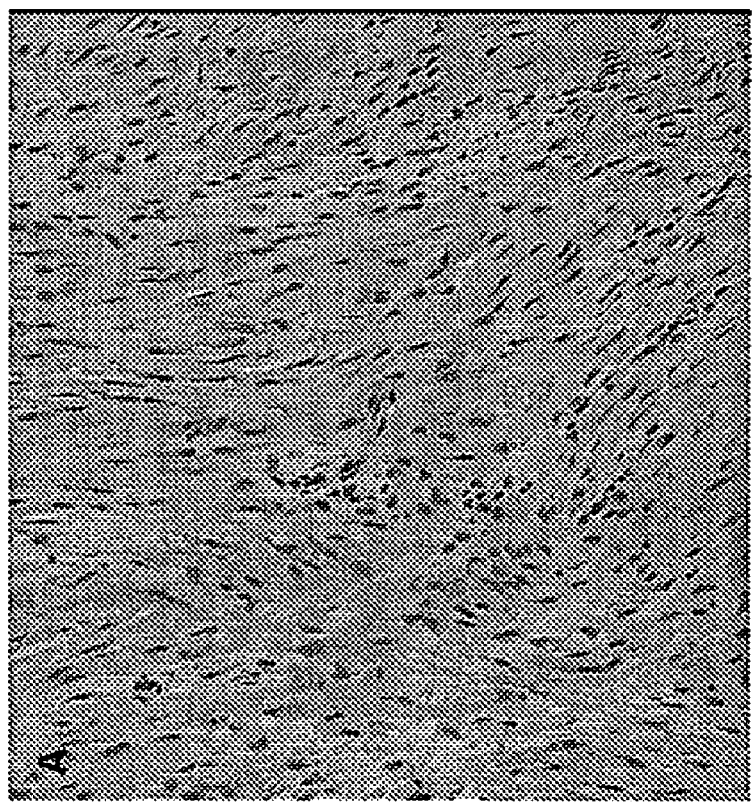

Histomorphology: H&E staining revealed that healing MCLs (Group 2) are hypercellular and have highly disorganized extracellular matrix through the injury site following two weeks of healing. Capsaicin treated (Group 4) healing MCLs were also hypercellular and disorganized. In addition, these tissues had less structure to the matrix in the healing site (i.e., crimp pattern was lost) and cells in this region seemed rounded, which is atypical of ligament fibroblasts (compare and contrast FIGS. 17A and 17B).

PNS Inhibition Degrades Healing Ligament: Results of this study show that capsaicin affects the peripheral nervous system and peripheral neuropeptides and results in detrimental effects on healing of fibrous connective tissue, such as the MCL. Ten days after capsaicin treatment, SP and CGRP were significantly decreased in MCLs. No significant decreases in mechanical properties were seen in intact MCLs following capsaicin treatment either in organ culture or in vivo. These data indicate that capsaicin did not measurably affect the integrity of the normal extracellular matrix. However, capsaicin significantly reduced the strength of healing tissues, indicating that capsaicin may alter the physiological response of tissue to injury. Furthermore, skin wounds in capsaicin treated animals also healed poorly compared to controls, indicating that the effects of capsaicin are not limited to ligamentous tissues. These data support the hypothesis that inhibition of the sensory nervous system affects ligament healing.

Neuropeptides, Capsaicin, and Wound Healing: The diminished healing observed in this study (by reduced tissue strength) may be due to the diminished levels of neuropeptides in the tissue following capsaicin administration. Ten days after capsaicin administration, SP and CGRP were both significantly reduced. Afferent neuropeptides (most notably SP) have proliferative effects on many cell types, and have been shown to play key roles in recruiting inflammatory cells to the site of injury during tissue healing. Fibroblasts, the main cellular component of ligamentous tissue, respond to SP by proliferating, which may also affect the amount of matrix (collagen) deposition and its fibroblast mediated organization. Cell culture studies show that SP (alone and in combination with a number of growth factors) can increase cell proliferation Nilsson, J., A. M. von Euler, and C. J. Dalsgaard, "Stimulation of connective tissue cell growth by substance P and substance K." *Nature*, 1985. 315 (6014): p. 61-3; McGovern, U. B., K. T. Jones, and G. R. Sharpe, "Intracellular calcium as a second messenger following growth stimulation of human keratinocytes." *British Journal of Dermatology*, 1995. 132(6): p. 892-6; Kahler, C. M., et al., "Interaction of substance P with epidermal growth factor and fibroblast growth factor in cyclooxygenase-dependent proliferation of human skin fibroblasts." *Journal of Cellular Physiology*, 1996. 166(3): p. 601-8; Haegerstrand, A., et al., "Calcitonin gene-related peptide stimulates proliferation of human endothelial cells." *Proceedings of the National Academy of Sciences of the United States of America*, 1990. 87: p. 3299-3303. In addition, animal models show that diminished levels of neuropeptides (due to capsaicin injection or diabetes) delays healing of skin wounds (Smith, P. G. and M. Liu, "Impaired cutaneous wound healing after sensory denervation in developing rats: effects on cell proliferation and apoptosis." *Cell & Tissue Research.*, 2002. 307(3): p. 281-91; Gibran, N. S., et al., "Diminished neuropeptide levels contribute to the impaired cutaneous healing response associated with diabetes mellitus." *Journal of Surgical Research.*, 2002. 108(1): p. 122-8).

This delayed healing in skin may be caused by depletion of SP, which can up-regulate epidermal growth factor (EGF) expression. When capsaicin functionally blocks the nerves that release SP, EGF expression is significantly reduced (Lai, X., et al., "Effect of substance P released from peripheral nerve ending on endogenous expression of epidermal growth factor and its receptor in wound healing." *Chinese Journal of Traumatology.*, 2002. 5(3): p. 176-9).

Furthermore, capsaicin administration or blocking of the SP receptor (NK-1) attenuates inflammatory responses in animal models (Ahluwalia, A., et al., "Impaired IL-1beta-induced neutrophil accumulation in tachykinin NK1 receptor knockout mice." *British Journal of Pharmacology*, 1998. 124 (6): p. 1013-5).

Neutrophil accumulation at a wound site can be regulated by SP, however in NK-1 receptor null mice (where SP functionally blocked), neutrophil accumulation is prevented, indicating that SP may influence an early response to injury, Ahluwalia, A., et al., supra. The work presented here supports these studies, suggesting that afferent neuropeptides can profoundly influence healing of soft tissues.

Significance: To our knowledge, this study is the first to show that capsaicin administration impedes healing in mature collagenous connective tissues. This study supports the hypothesis that inhibition of the sensory nervous system will alter the biological and mechanical properties of healing ligaments. The study also supports the concept that afferent neuropeptides play an essential role in wound healing, and that depletion of these neuropeptides (especially SP and CGRP) delays wound healing. The study also raises questions about the widespread use of capsaicin for pain management, especially in cases where tissue injury has occurred. Even though capsaicin is a proven pain management tool, the drug should be used with discretion since it will alter afferent neuropeptide concentrations. Delayed healing as the result of capsaicin administration may increase morbidity in healing tissue.

Example 6

Local Delivery of Additional Neuropeptides

Herein, we specifically test that the deficits we previously saw are in fact due to alterations in neuropeptide concentrations. We chose to locally deliver one (or a combination) of four neuropeptides to the MCL: SP, CGRP, VIP, or NPY. These neuropeptides were chosen due to their presence in the MCL, and the potential role they play in healing of soft collagenous connective tissues. This study investigated whether altered neuropeptides directly affect the healing MCL mechanical properties in vivo. Specifically, the following hypotheses were tested:

1. Local delivery of sensory neuropeptides (SP and CGRP) to neuropathic tissues alters biological and mechanical properties of healing MCLs.

2. Local delivery of sympathetic neuropeptides (NPY and VIP) to neuropathic tissues alters biological and mechanical properties of healing MCLs. To study the above hypothesis, the following specific aims were met.

(a) Determine neuropeptide induced changes in strength and stiffness.

(b) Determine neuropeptide induced changes in MCL morphology.

Experimental Design:

Animal Model and Surgery: Thirty-seven female Wistar rats (199-298 g) were divided into five groups. To each group, one of the following neuropeptide solutions was delivered to the intramuscular space above a healing MCL: SP (75 pg/100 µl); CGRP (10 pg/100); NPY (65 pg/100 µl); VIP (100 pg/100 µl); and a combination of NPY and VIP (NPY 65 pg/100 µl; VIP 100 pg/100 µl). For all groups, anesthesia (isofluorane 0.5-3%) was initiated in an induction chamber and maintained with a facemask. Rats that were designated to receive SP or CGRP underwent bilateral femoral nerve transection (see previous examples). Rats that were designated to receive NPY, VIP, or a combination of NPY and VIP underwent bilateral surgical sympathectomy. Following surgical nerve transection, each rat also underwent bilateral MCL rupture. Neuropeptides were then delivered ruptured MCLs unilaterally. Neuropeptide infused mini-osmotic pumps (Alzet Corp.) were implanted subcutaneously into the back of each rat. A small catheter running from the pump was run to an intramuscular space above the MCL and was secured. To ensure that neuropeptides are delivered directly to the MCL, rhodamine labeled SP was delivered via a catheter to the MCL (n=2 rats). Confocal microscopy of these MCLs showed that exogenous SP was delivered to the MCL.

To test whether sensory NPs improve healing in femoral nerve transaction (FNT) ruptured MCLs, seven female Wistar rats were given SP and seven rats were given CGRP locally to the MCL. Within minutes of surgical intervention, all rats recovered and had normal movement and behavior (grooming, feeding, etc.). To test whether autonomic NPs improve healing in SS ruptured MCLs, seven rats were given VIP, seven rats were given NPY, and seven rats were given a combination of VIP and NPY. Within minutes of surgical intervention, all rats recovered and had normal movement and behavior (grooming, feeding, etc.).

Mechanical Testing: Mechanical testing was performed as described in the preceding examples. Briefly, animal hind limbs from all groups (n=4 for all groups) were disarticulated at the hip joint and stored at −80° C. until testing. On the day of testing, MCLs including intact femoral and tibial bone sections were excised for ex vivo testing. Ligament thickness and width was measured optically, and MCL area was estimated with elliptical geometry. For strain measurements, optical markers were placed onto the ligament tissue near the insertion sites. A small preload of 0.1N was applied to the ligaments in order to obtain a uniform starting point. The ligaments were then preconditioned to 1% strain for 10 cycles. After preconditioning, ligaments were pulled to failure at a rate of ~10% per second. Tissue displacement was obtained using video dimensional analysis using equations (1) and (2) supra. The mechanical properties that were examined in this study were maximum force, ultimate stress, strain at failure, elastic modulus, and area. Statistical analysis was performed using paired tests to compare each treated MCL to its contralateral control (alpha=0.05).

Tissue Histomorphology: Immediately following death, MCLs from three rats from each group were exposed and dissected in toto from the tibial and femoral insertions. Ligaments were immediately fixed in formalin fixative for three days at room temperature. Specimens were embedded in paraffin, sectioned (6 μm), mounted on slides, and stained with hematoxylin and eosin (H&E).

Results:

Surgical Outcomes: No abnormalities in movement, body weight, or behavior were observed in any treated group. Upon tissue harvest, no morphological differences were macroscopically observed between control and treated MCL tissues.

Figure 18A:
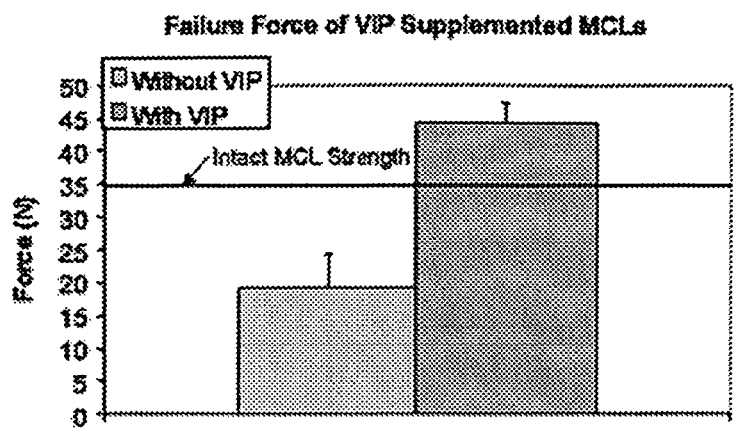
FIGS. 18A, 18B, and 18C are a series of graphs showing the failure force of MCLs treated with VIP (FIG. 18A), NPY (FIG. 18B), and SP (FIG. 18C) as compared to controls.
Figure 18B:
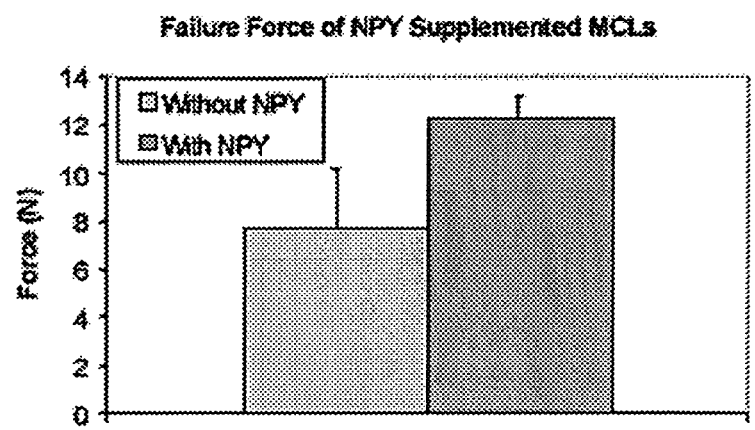
Figure 18C:
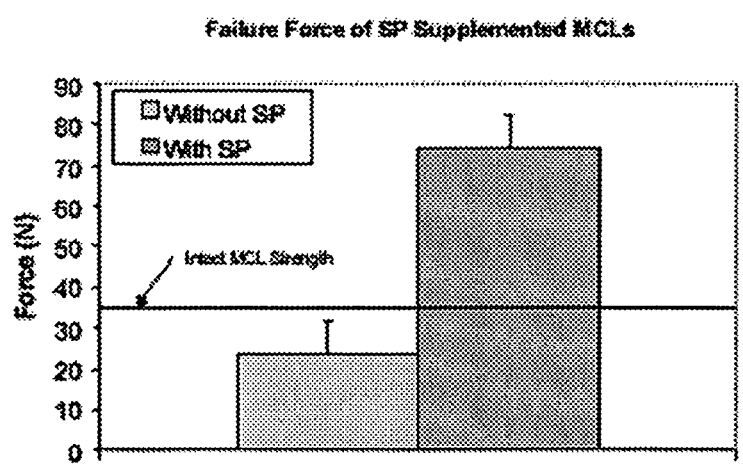

MCL Mechanics: Mechanical testing showed SP supplemented FNT MCLs had a much greater failure force (74.3±7.9 vs. 23.4±8.0 N; paired Student's t-test p=0.001; and ultimate stress (72.33±22.1 vs. 20.9±9.9 MPa; paired Student's t-test p=0.03) following two weeks of healing when compared to healing without SP. Substance P completely reversed the functional deficits that are caused by femoral nerve transaction. The mechanical strength of SP supplemented MCLs was greater than that of normally innervated, intact MCLs. No mechanical changes were seen in MCLs supplemented with CGRP. VIP supplemented SS MCLs had a much greater failure force (44.2±3.1 vs. 19.4±5.0 N; paired Student's t-test p=0.005) and ultimate stress (29.6±10.0 vs. 10.1±1.4 MPa; paired Student's t-test p=0.07) following two weeks of healing when compared to healing without VIP. See FIGS. 18A, 18B, 18C.

Like SP, VIP completely reversed the functional deficits caused by surgical sympathectomy. Vasoactive intestinal peptide supplemented MCLs had greater strength than intact, normally innervated MCLs. NPY supplemented MCLs also had a greater failure force following two weeks of healing (12.2±0.9 vs. 7.7±2.4 N; paired Student's t-test p=0.015), however the effects of VIP were greater than the effects of NPY. A combination of VIP and NPY also improved the mechanical strength of healing surgically sympathectomized MCLs.

The combination delivery group had an increase in failure force (12.36±1.22 vs. 8.69±2.16 N; paired Student's t-test p=0.10) and ultimate stress (9.60±2.47 vs. 6.50±1.92 MPa; paired Student's t-test p=0.026). This group also showed a significant reduction in the failure strain (0.067±0.011 vs. 0.081±0.017; paired Student's t-test p=0.05), which may indicate a changes in the structure or composition of the tissue.

Histomorphology: Every neuropeptide tested influenced ligament morphology. Histological analysis of SP supplemented MCLs showed cells were more aligned even in scar regions of SP treated MCLs when compared to controls. CGRP treated MCLs remained disorganized and had few spindle shaped cells in healing areas of the MCL. Histological analysis of VIP and NPY supplemented MCLs showed cells for both NPs were more aligned especially in scar regions when compared to controls (which is similar to results for SP supplemented MCLs). To our knowledge, these are the first data to show that sympathetic and sensory neuropeptides improve healing in neuropathic tissues in vivo.

Discussion

Neuropeptides Reverse Neuropathy Induced Mechanical Deficits: Data in this study clearly show that the peripheral nervous system plays an important and largely ignored role in recovering the strength of healing tissues. Surgical sympathectomy significantly reduces the healing strength of MCLs, as does sensory denervation.

Neuropeptides SP, NPY, and VIP play a substantial role in ligament healing. Delivery of VIP and SP completely reverses the effects of neuropathy on the strength of ruptured MCLs after only two weeks of healing. The level of functional recovery was so great that there appears to be a protective effect on residual ligament tissues and insertion sites. Loss of insertion strength has been identified as a long-term problem after ligament healing. In addition, NPY improves the healing response of MCLs to 70% of intact controls. VIP, NPY, and SP also alter tissue morphology by increasing cell alignment and extracellular matrix organization in the scar region. By comparison, local delivery of CGRP, which did not improve the mechanical properties of healing ligaments, produced a very disorganized matrix with fewer spindle-shaped cells throughout the healing region.

The effect of neuropeptides on neuropathic MCL healing is impressive, and to date, no other factor has had such an effect on healing in a soft tissue in vivo. The in vivo effect of neuropeptides on connective soft tissue healing has until now gone unnoticed. Although the role of neuropeptides in normally innervated tissue healing has yet to be determined, their remarkable effect on neuropathic MCLs suggest potent therapeutic applications for reducing healing morbidity in other neuropathic tissues (e.g. diabetic populations). By extrapolation, neuropeptides could serve as a therapeutic agent for other tendon and ligament injuries and for healing of graft harvest sites in ligament and tendon grafting.

In addition to potential therapeutic value, data contained herein indicate that the peripheral nervous system and its agents may play a key role in tissue grafting and tissue engineering. To date, no tissue-engineered scaffold fulfills the biomechanical requirements for in vivo loading. As increasingly sophisticated engineered tissues are developed, the role of peripheral innervation should not be ignored. Incorporation of peripheral agents into such tissues may help create pathways for blood vessel formation, and may improve inflammatory responses following implantation. Furthermore, data in this study suggest that neuropeptides play a role in organizing cells and extracellular matrix tissue. Surgical implications then emerge. The role of the peripheral nervous system should also be considered during graft procedures where the native nervous tissue is disrupted or completely removed. Grafted tissues remodel themselves in a manner similar to engineered tissues, undergoing avascular necrosis of the original cells, revascularization, cellular repopulation, and matrix remodeling. As chemotactic and proinflammatory agents, neuropeptides have the potential to influence these processes as well.

Example 7

Local Neuropeptide Delivery Improves Normal MCL Healing

Animal Model and Surgery: Forty female Wistar rats (200-250 g) were divided into five groups. To each group, one of the following neuropeptide solutions was delivered to the intramuscular space above a healing MCL: SP (75 pg/100 µl); CGRP (10 pg/100 µl); NPY (65 pg/100 µl); VIP (100 pg/100 µl); and a combination of NPY and VIP (NPY 65 pg/100 µl; VIP 100 pg/100 µl).

For all groups, anesthesia (isofluorane 0.5-3%) was initiated in an induction chamber and maintained with a facemask. All rats underwent bilateral MCL rupture. Neuropeptides were then delivered ruptured MCLs unilaterally. Neuropeptide infused mini-osmotic pumps (Alzet Corp.) were implanted subcutaneously into the back of each rat. A small catheter running from the pump was run to an intramuscular space above the MCL and was secured. Within minutes of surgical intervention, all rats recovered and had normal movement and behavior (grooming, feeding, etc.).

Mechanical Testing: Mechanical testing was performed as described in Chapter 2. Briefly, animal hind limbs from all groups (n=5 for all groups) were disarticulated at the hip joint and stored at −80° C. until testing. On the day of testing, MCLs including intact femoral and tibial bone sections were excised for ex vivo testing. Ligament thickness and width was measured optically, and MCL area was estimated with elliptical geometry. For strain measurements, optical markers were placed onto the ligament tissue near the insertion sites. A small preload of 0.1N was applied to the ligaments in order to obtain a uniform starting point. The ligaments were then preconditioned to 1% strain for 10 cycles. After preconditioning, ligaments were pulled to failure at a rate of 10% per second.

Tissue displacement was obtained using video dimensional analysis using equations (1) and (2) supra. The mechanical properties that were examined in this study were maximum force, ultimate stress, strain at failure, elastic modulus, and area. Statistical analysis was performed using paired ttests to compare each treated MCL to its contralateral control (alpha=0.05).

Tissue Histomorphology: Immediately following death, MCLs from three rats from each group were exposed and dissected in toto from the tibial and femoral insertions. Ligaments were immediately fixed in formalin fixative for three days at room temperature. Specimens were embedded in paraffin, sectioned (6 µm), mounted on slides, and stained with hematoxylin and eosin (H&E).

Results:

Surgical Outcomes: No abnormalities in movement, body weight, or behavior were observed in any treated group. Upon tissue harvest, no morphological differences were macroscopically observed between control and treated MCL tissues.

MCL Mechanics: The results from these experiments were similar to the results from those in Example 3, however neuropathic MCLs saw greater improvement than normal MCLs with neuropeptide supplementation. Mechanical testing showed SP supplemented MCLs had a greater ultimate stress (13.4±8.9 vs. 5.8±3.2 MPa; paired Student's t-test p=0.04) following two weeks of healing when compared to healing without SP. There was no change in the failure force in Substance P supplemented MCL.

MCLs supplemented with CGRP showed weakening in mechanical strength. Of the five MCLs that were supplemented, three failed to fully heal and could not heal. The remaining two were much weaker than unsupplemented controls. The failure force (4.0±5.8 vs. 7.9±3.7 N; paired Student's t-test p=0.04) and ultimate stress (1.8±2.5 vs. 5.4±1.6 MPa; Student's t-test p=0.005) of CGRP supplemented MCLs was weaker than unsupplemented contralateral controls.

VIP supplemented MCLs also had greater failure force (10.2±3.0 vs. 5.9±2.8 N; paired Student's t-test p=0.02) and ultimate stress (5.1±1.6 vs. 3.6±1.4 MPa; paired Student's t-test p=0.03) following two weeks of healing when compared to healing without VIP. NPY supplemented MCLs also had a greater failure force (7.7±1.1 vs. 5.4±1.2 N; paired Student's t-test p=0.004) and ultimate stress (5.6±2.2 vs. 3.6±1.2 MPa; paired Student's t-test p=0.05) following two weeks of healing. Again the effects of VIP were greater than the effects of NPY.

A combination of VIP and NPY also improved the mechanical strength of healing MCLs. The combination delivery group had an increase in failure force (7.7±3.0 vs. 4.9±2.5 N; paired Student's t-test p=0.005) and ultimate stress (6.9±2.9 vs. 3.5±2.2 MPa; paired Student's t-test p=0.007). Unlike the neuropathic case, this group did not show a significant reduction in the failure strain.

Histomorphology: As shown in Example 3, local delivery of peripheral neuropeptides influences ligament morphology. Consistent with neuropathic healing data, VIP and SP greatly improved tissue alignment in healing regions when compared to controls. Neuropeptide Y had less of an effect on tissue alignment. In addition, CGRP supplemented MCLs were highly disorganized with few spindle shaped cells within the healing region. To our knowledge, these are the first data to show that peripheral neuropeptide influence the ligament histomorphology of normally innervated healing MCLs.

Neuropeptides Improve Mechanical Strength of Healing MCLs: Three of the neuropeptides investigated improve the strength of healing MCLs: SP, VIP, and NPY. A combination of NPY and VIP also improved MCL healing. Substance P had the greatest effect on MCL healing. MCLs supplemented with SP healed to within 60% of intact MCL strength after only two weeks of healing. Two weeks of SP delivery results in strength that is as good as, and in some cases better than, the MCL healing following months growth factor augmentation.

Significance: The effect of SP, VIP, and NPY on MCL healing is impressive. Particularly, SP improved MCL healing to 60% of the intact strength of a normal MCL after only two weeks of healing. This result is as good, or better than, growth factor augmentation, over a much shorter healing period.

Example 8

Subcutaneous Neuropeptide Delivery Improves Cartilage Healing

Purpose-bred male Wistar rats, were used in this Example. Rats were acclimated to the animal care facility for seven days before use. All rats then undergo general anesthesia for surgical induction of cartilage injury. All rats underwent bilateral surgery. At the time of surgery, miniosmotic pumps were placed for NP treatment. All pumps remained in place throughout the experiment. At various time intervals after the surgery (2, 4 and 6 weeks), the rats were euthanized each joint was harvested for histological analysis.

Rats were observed twice daily for the first day after above treatments and daily thereafter throughout the protocol. Rats were weighed prior to treatment and at euthanasia.

General anesthesia was induced and maintained with isofluorane (0.5-3.0%) with an induction chamber and then a facemask. Premedication was by subcutaneous injection of glycopyrrolate (0.01-0.02 mg/kg) and butorphanol (0.5 mg/kg). An additional dose of butorphanol (0.5 mg/kg) was be given by subcutaneous injection four hours after initial dose only when necessary. Immediately after anesthesia, rats were maintained in a warmed environment and observed continuously until they had regained the ability to walk and then were returned to their normal cage environment.

Cartilage Injury: A 5-6 cm long incision was made over the patellar tendon and the tendon and surrounding tissue was exposed. A mini-arthrotomy was made and the patella was subluxed (dislocated) to expose the femoral condyles and trochlear groove. A drill was used to create a full thickness (3 mm deep) hole, 0.635 mm in diameter, in the trochlear groove. The patella was then repositioned and the muscle fascia and subcutaneous tissue was closed with a continuous suture pattern, and the skin apposed with skin staples.

Neuropeptide delivery: Substance P (75 pg/100 µl) was infused subcutaneously (0.25 µl/hr) via the implantation of mini-osmotic pumps (Alza Corp. Palo Alto, Calif.). In all rats, neuropeptide infused pumps were implanted in a subcutaneous pocket after induction of general anesthesia. A small PE-60 catheter was attached to the pump and run through a subcutaneous pocket from the pump to the joint space. The pump was secured within muscle tissue as the joint was closed (3-0 dexon suture). The catheter was secured to the hamstrings in two places (near the knee and hip joints) using sutures.

Euthanasia was performed by intraperitoneal injection of pentobarbitone (150 mg/kg). Death was confirmed by absence of a heart beat.

Following euthanasia joint tissue was dissected to remove all extracapsular structures (leaving ACL, PCL, cartilage, and meniscus). Remaining joint tissue was decalcified and sectioned for histological analysis. All joints were stained with hemotoxylin and eosin, Masson's trichrome staining, and safranin O.

Each specimen was blinded and graded using a published grading method (Sellers, 1997, JBJS(A) 79, 1452-63). Specimens were graded based on eight criteria:
1. Filling of the defect
2. Integration of repair tissue with normal cartilage
3. Matrix staining with safranin-O
4. Cellular morphology
5. Condition of the repaired cartilage
6. Architecture of the surface
7. Percentage of new subchondral bone
8. Complete formation of a tidemark Scores were given for each category and then totaled for the entire specimen. Grading could range from 0 (no damage) to 24 (indication of fibrosis and osteoarthritis within the joint). Each measurement was made by three independent and blinded observers. Total scores for each knee were made based on multiple observations of the same joint. Once scores were given for each specimen, the blinding was removed and scores were categorized by treatment with SP, no treatment, and control (no injury). Averages for each group were compared using ANOVA.

Figure 20A:
FIGS. 20A, 20B, and 20C are photomicrographs of full-thickness cartilage defects after two weeks of healing (see Example 8).
Figure 20B:
Figure 20C:

Results show that untreated cartilage defects did not heal well in the initial two week period. The average score for this group was 22.2 (out of a possible 24 points), indicating poor healing of both the cartilage and subchondral bone (see FIG. 20A). Treated defects showed improved healing in the initial two week period. The average score for this group was 11.9 (out of a possible 24 points) (see FIG. 20B). The improved score was due to both filling in of the cartilage defect and improved healing of the subchondral bone. The average for uninjured cartilage was 1.8, indicating little to no defects within the joint (see FIG. 20C).

Augmented cartilage and bone healing with neuropeptides represents a new paradigm for the treatment of cartilage and subchondral bone injuries. Cartilage injury at any age can lead to arthritis and the need for a joint replacement. Often times injured cartilage must undergo surgical repair or replacement in order to prevent deterioration of the joint. Even with such treatments, osteoarthritis can result. The treatment shown herein may lead to regeneration of injured cartilage and prevention of fibrosis within the joint. This treatment would also be less invasive than microfracture, drilling, and grafting procedures that are often used to treat such injuries.

Example 9

Neuropeptide Effects on Bovine Articular Chondrocytes

Bovine articular cartilage was harvested under sterile conditions from the condyles and patellar grooves of bovine knees and rinsed twice in Dulbecco's Modified Eagle's medium (DMEM) supplemented with antibiotics and 10% FBS. Cartilage chunks were then digested at 37° C. in DMEM containing 0.05% hyaluronidase for 30 minutes, followed by 0.05% collagenase digestion overnight. The digests were filtered through 40-micron nylon mesh and centrifuged at 600×g for 20 minutes. The cell pellets were then resuspended in DMEM and counted using a hemacytometer.

Cells were plated at $1 \times 10^5$ cells/well in 12-well plates (n=9) for proteoglycan assays and at $2 \times 10^4$ cells/well in 96-well plates (n=16) for proliferation assays. The culture volumes were 1 ml/well in 12-well plates and 100 µl/well in 96-well plates.

The plates were incubated at 37° C. in a humidified $CO_2$ incubator for 3 days to allow the cells to recover from the harvesting procedure.

The media were then changed to serum-free (i.e., 0.1% BSA) DMEM containing neuropeptides at the following concentrations: (a) control; (b) CGRP (100 pg/ml); (c) NPY 50 ng/ml; (d) SP (500 pg/ml); and (e) VIP (1 ng/ml).

On Day 3 of treatment, 20 µl of CellTiter 96® AQ$_{ueous}$ One Solution Cell Proliferation Assay (Promega Corporation, Madison, Wis.) was added to each well of the 96-well cultures for 60 minutes, and cells in the 12-well plates were digested with 0.125 units of papain/well overnight. After the 60-minute incubation, the absorbance of the color generated by the cells in the 96-well plates was measured at wavelength 490 nm. (The color, reflective of cell number, results from the conversion of the compound MTS to its formazan product by live cells.)

Following papain digestion of the cultures in 12-well plates, the amount of glycosaminoglycan (representative of proteoglycans) in each well was measured using the dimethylmethylene blue (DMMB) dye-binding assay. The results were statistically analyzed and plotted. The raw results are tabulated below and are presented graphically in FIGS. 21, 22, and 23.

TABLE 2

Effects of Neuropeptides on Bovine Chondrocytes -
Proliferation Assay (data indicate relative luminescence units)
Day 3

| control | CGRP (100 pg/ml) | NPY (50 ng/ml) | SP (500 pg/ml) | VIP (1 ng/ml) |
|---|---|---|---|---|
| 0.77 | 0.8647 | 0.7984 | 0.8791 | 0.9411 |
| 0.7704 | 1.0656 | 0.9075 | 0.9974 | 0.9155 |
| 0.8325 | 1.0864 | 0.999 | 0.9607 | 0.9361 |
| 0.8064 | 1.057 | 1.1014 | 0.9168 | 1.0329 |
| 0.8132 | 1.0238 | 0.9977 | 0.9856 | 1.0833 |
| 0.8675 | 0.9447 | 0.9972 | 0.9589 | 1.0366 |
| 0.8227 | 0.9197 | 0.9026 | 0.9525 | 0.9767 |
| 0.8423 | 0.8682 | 0.8507 | 0.8613 | 0.9508 |
| 0.7891 | 0.8188 | 0.8269 | 0.9651 | 0.9241 |
| 0.8573 | 0.9139 | 0.9273 | 0.9186 | 0.8811 |
| 0.9025 | 0.8672 | 0.9408 | 1.0591 | 0.9056 |
| 0.8729 | 0.9845 | 1.0525 | 0.955 | 0.9473 |
| 0.8572 | 0.9986 | 0.9922 | 1.0587 | 0.9829 |
| 0.8784 | 0.9699 | 1.0303 | 1.0581 | 1.0151 |
| 0.917 | 0.943 | 0.9485 | 0.8985 | 0.8347 |
| 0.9383 | 0.8546 | 0.8212 | 0.7951 | 0.789 |

TABLE 3

Effects of Neuropeptides on Bovine Chondrocytes -
Glycosaminoglycan Assay (data indicate µg/dish)

| control | CGRP (100 pg/ml) | NPY (50 ng/ml) | SP (500 pg/ml) | VIP (1 ng/ml) |
|---|---|---|---|---|
| 10.23566 | 7.510186 | 5.784055 | 7.237639 | 6.147451 |
| 10.5082 | 9.690563 | 7.873582 | 7.283064 | 6.510847 |
| 11.78009 | 9.690563 | 8.327827 | 8.009856 | 8.327827 |
| 11.96179 | 7.14679 | 7.782733 | 8.600374 | 7.419337 |
| 12.41603 | 8.872921 | 9.327167 | 9.100044 | 5.965753 |
| 12.23434 | 7.601035 | 6.2383 | 8.373252 | 6.874243 |
| 9.781412 | 6.783394 | 8.05528 | 7.010516 | 6.419998 |
| 9.781412 | 6.965092 | 7.964431 | 6.556271 | 6.965092 |
| 6.419998 | 5.511508 | 5.148111 | 7.192214 | 3.785376 |

Figure 21:
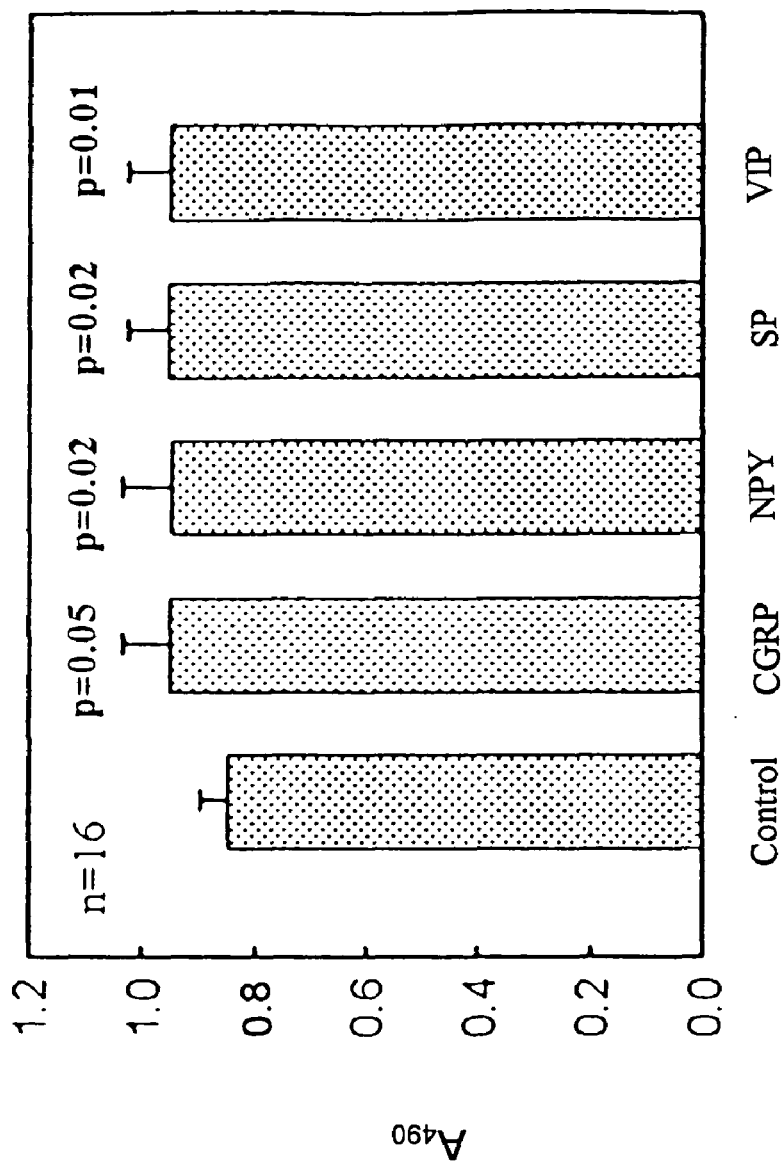
FIG. 21 is a graph depicting the results of the cell proliferation assay presented in Example 9.

FIG. 21 is a graph depicting the results of the cell proliferation assay. (FIG. 21 depicts in histogram form the raw data presented in Table 2). The increased proliferation in all of the treatment groups is significant (p<0.001) as compared to the untreated control. Multiple statistical comparisons versus the control group using the Holm-Sidak method also revealed that the results for all of the treatment groups are significant as compared to the control group. These results unequivocally show that neuropeptides administered at the levels noted herein increase the proliferation of articular chondrocytes. Thus, the present invention is also useful to encourage the healing of damaged bone.

Figure 22:
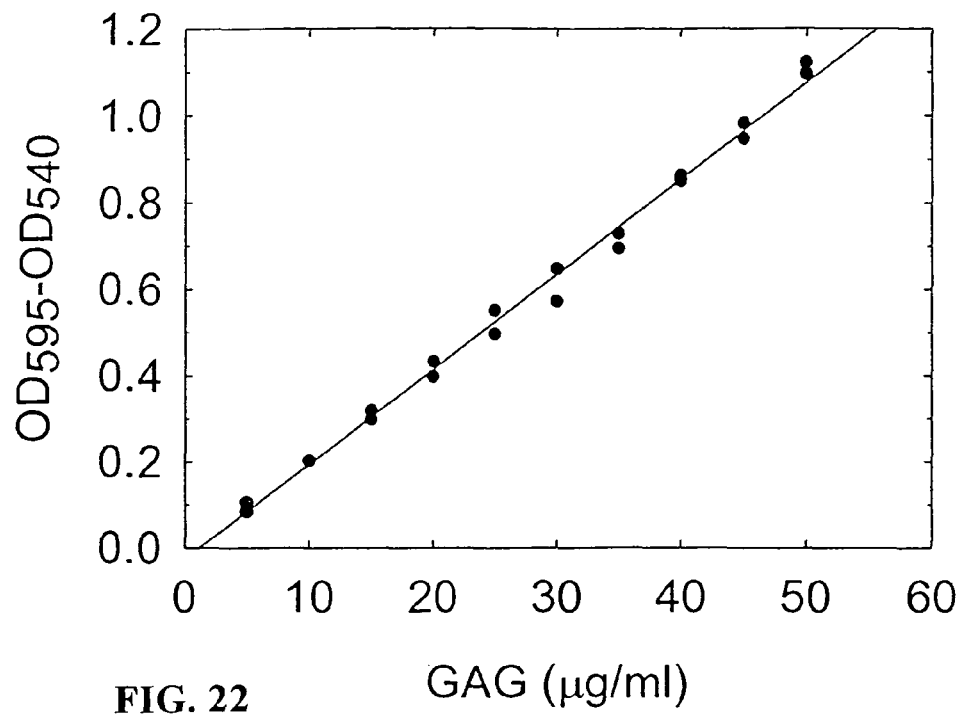
FIG. 22 is the standard curve for the glycosaminoglycan assay presented in Example 9.
Figure 23:
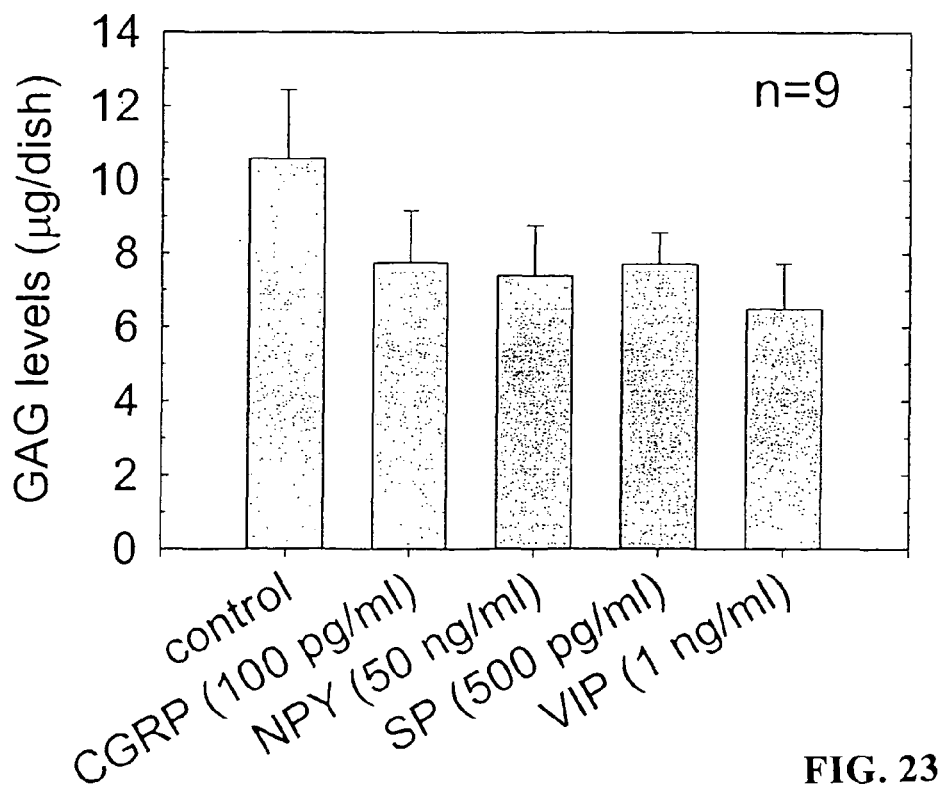
FIG. 23 is a graph depicting the results of the glycosaminoglycan assay presented in Example 9.

FIG. 22 is the standard curve for the glycosaminoglycan assay ("GAG Standard Curve"). FIG. 23 is a graph depicting the results of the glycosaminoglycan assay. (FIG. 23 depicts in histogram form the raw data presented in Table 3). This assay confirms the proliferation results presented in FIG. 21. In short, when cells are proliferating, the amount of glycosaminoglycan produced decreases (because the cells are committing their metabolic energy to cell division, rather than to protein production). The decreased glycosaminoglycan production in all of the treatment groups is significant (p<0.001) as compared to the untreated control. Multiple statistical comparisons versus the control group using the Holm-Sidak method also revealed that the results for all of the treatment groups are significant as compared to the control group. These results corroborate the results of the cell proliferation assay. These results further confirm that neuropeptides administered at the levels noted herein increase the proliferation of articular chondrocytes.

Example 10

Neuropeptide Effects on Bovine Articular Chondrocytes and Intervertebral Disc Cells Bovine calf spines and femoral condyles were obtained from a slaughterhouse and freshly transported to the laboratory. Nucleus pulposus tissue was carefully dissected, avoiding annular and endplate cartilage tissues, from each disc. Articular cartilage from femoral condyles was dissected in the same manner. Tissues were incubated in Dulbecco's modified Eagle's medium (DMEM) supplemented with fetal calf serum, antibiotics, and amino acids. Cells were harvested by overnight digestion with hyaluronidase and collagenase, followed by filtration. Cells were plated at a density of $1 \times 10^5$ cells/ml and incubated at 37° C. in 5% $CO_2$ and 95% air in the presence of each neuropeptide or media only (control). At various time points in growth, cells were collected for proliferation and glycosaminoglycan (GAG) production assays. Varying concentrations of NPs were examined.

Well established colorimetric and luminescent assays (CellTiter 96® AQueous Non-radioactive Cell Proliferation and CellTiter-Glo® Luminescent Cell Viability Assays, Promega, Madison, Wis.) were used to quantify the effect of each NP on cell proliferation. In addition, corresponding cell cultures during growth were digested with papain to release glycosaminoglycans (GAGs). Dimethyl methylene blue (DMMB) colorimetric assays were used to quantify the amount of GAGs in each culture.

Multiple samples for test and control groups were performed simultaneously. Statistical analyses using one way analysis of variance (ANOVA) with large degrees of freedom (n=12 for GAG assays; n=24 for proliferation assays) were performed to establish the significance of differences between test groups and control groups for each day of growth in culture.

The in vitro experiments with bovine articular cartilage chondrocytes are described in Example 9. In culture, CGRP, NPY, SP, and VIP stimulate proliferation of these chondrocytes compared to controls (FIG. 21). As expected, GAG production is also affected (data not shown). As chondrocyte cells are in a proliferative phase, GAG production initially decreases as cell metabolism is dedicated to proliferation. Confluent cell cultures have not yet been included in our experiments.

Figure 24:
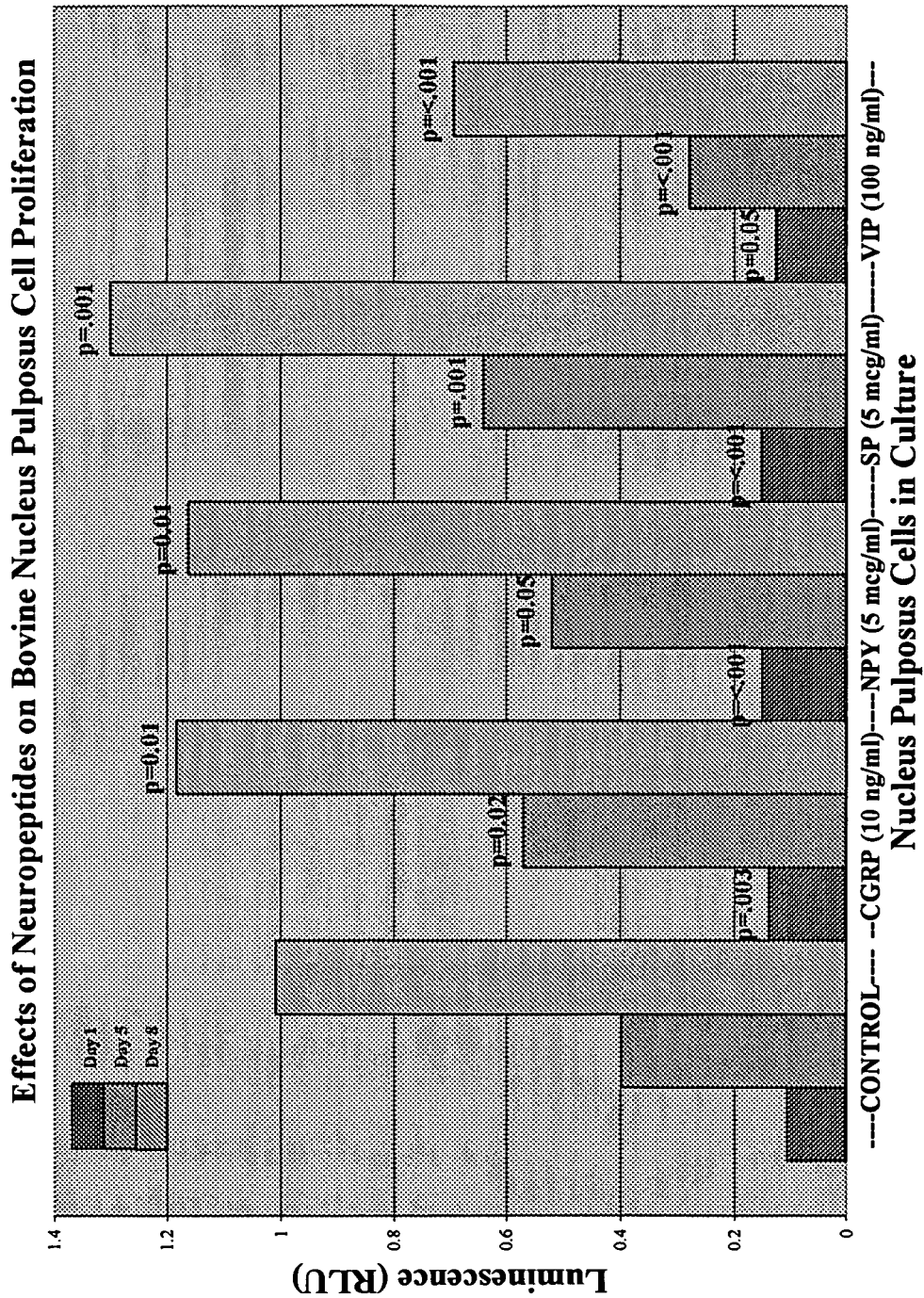
FIG. 24 is a graph depicting the effect of neuropeptides CRGP, NPY, SP, and VIP on the proliferation of bovine nucleus pulposus cells (see Example 10).

The effect of neuropeptides on intervertebral disc cell proliferation was examined in order to elucidate further the pathophysiology of degenerative disc disease. Bovine nucleus pulposus cells were incubated with the same neuropeptides. CGRP (10 ng/ml), NPY (mcg/ml, and SP (5 mcg/ml) stimulate disc cell proliferation compared to controls, while VIP (100 ng/ml) had a negative influence on disc cell viability. The results on day 1, day 2, and day 3 are presented in (FIG. 24). These results were statistically significant ($p<0.05$, $n=24$).

The results of this Example demonstrate that NPs affect articular chondrocytes and intervertebral disc cells. The data demonstrate the influence of neuropeptides on proliferation and GAG expression. These results not only identify agents of therapeutic value, they also help elucidate the pathophysiology of degenerative joint and disc disease and the emerging role of the peripheral nervous system in soft tissue healing and homeostasis.

Neuropeptides possess several advantages as an approach to therapy over growth factors such as OP-1. Because neuropepties are small peptides, they are less expensive (because they are easily synthesized) and they are easier to integrate into systems of targeted drug delivery.

REFERENCES

Ackermann P W, Ahmed M, Kreicbergs A (2002) Early nerve regeneration after Achilles tendon rupture-a prerequisite for healing? A study on the rat. J Orthop Res 20:849-856.

Ackermann P W, Li J, Lundeberg T, Kreicbergs A (2003) Neuronal plasticity in relation to nociception and healing of rat achilles tendon. Journal of Orthopaedic Research 21:432-441.

Association A D (2000) Type I diabetes—Neuropathy. In.

Carter R B (1991) Topical capsiacin in the treatment of cutaneous disorders. Drug Development and Research 22:109-123.

Dray A (1992) Neuropharmacological mechanisms of capsaicin and related substances. Biochemical Pharmacology 44:611-615.

Dunnick C A, Gibran N S, Heimbach D M (1996) Substance P has a role in neurogenic mediation of human burn wound healing. Journal of Burn Care & Rehabilitation 17:390-396.

Dwyer K W, Provenzano P, Jensen K T, Vanderby Jr. R (2003) Inhibition of Peripheral Nervous System Alters Ligament Healing. Proc of the ASME Bioengr Meeting, Key Biscayne, Fla.

Field J, Atkins R M (1993) Effect of guanethidine on the natural history of post-traumatic algodystrophy. Annals of the Rheumatic Diseases 52:467-469.

Gado K, Emery P (1996) Intra-articular guanethidine injection for resistant shoulder pain: a preliminary double blind study of a novel approach. Annals of the Rheumatic Diseases 55:199-201.

Jessell T M, Iversen L L, Cuello A C (1978) Capsaicin-induced depletion of substance P from primary sensory neurones. Brain Research 152:183-188.

Kirschenbaum H L, Rosenberg J M (1984) What to look out for with guanethidine and reserpine. RN 47:31-33.

Promotion NCfCDPaH (2000) The prevention and treatment of complications of diabetes mellitus: A guide for primary care prationers. In: (Program CD, ed).

Santoni G, Perfumi M, Bressan A M, Piccoli M (1996) Capsaicin-induced inhibition of mitogen and interleukin-2-stimulated T cell proliferation: its reversal by in vivo substance P administration. Journal of Neuroimmunology 68:131-138.

Schaffer M, Beiter T, Becker H D, Hunt T K (1998) Neuropeptides: Mediators of inflammation and tissue repair? Archives of Surgery 133:1107-1116.

Sekul E A (2001) Femoral Neuropathy. In: (Shah A K, Talayera F, Buris N A, Baker M J, Lorenzo N, eds).

Stroke NIoNDa (2001a) Guillain-Barre syndrome fact sheet. In.

Stroke NIoNDa (2001b) Pain—Hope through research.

Stroke NIoNDa (2001c) Reflex sympathetic dystrophy/complex regional pain syndrome.

Stroke NIoNDa (2001d) NINDS Diabetic Neuropathy Information Page.

Surh Y J, Lee S S (1996) Capsaicin in hot chili pepper: carcinogen, co-carcinogen or anticarcinogen? Food & Chemical Toxicology 34:313-316.

Wahren L K, Gordh T, Jr., Torebjork E (1995) Effects of regional intravenous guanethidine in patients with neuralgia in the hand; a follow-up study over a decade. Pain 62:379-385.

What is claimed is:

1. A method of treating traumatic cartilage injury, the method comprising administering to the subject an amount of a neuropeptide selected from the group consisting of calcitonin gene-related peptide (CGRP), eholecystokinin (CCK), dynorphin, enkephalin, galanin, neuropeptide Y (NPY), neurotensin, somatostatin, substance P (SP), thyrotropin-releasing hormone (TRH), vasoactive intestinal peptide (VIP), and combinations thereof, the amount being effective to stimulate repair of the injured cartilage.

2. The method of claim 1, wherein the neuropeptide is administered in combination with a pharmaceutically suitable carrier.

3. The method according to any one of claims 1 or 2, wherein the neuropeptide is administered to a mammal.

4. The method according to any one of claims 1 or 2, wherein the neuropeptide is administered to a human.

* * * * *